(12) United States Patent
Ainsworth et al.

(10) Patent No.: US 8,038,680 B2
(45) Date of Patent: Oct. 18, 2011

(54) DRIVERS FOR INSERTS TO BONE ANCHORS

(75) Inventors: Stephen D. Ainsworth, Wilmington, NC (US); Brandon B. Arthurs, Wilmington, NC (US); Robert L. Assell, Wilmington, NC (US); Eugene A. Dickhudt, Lino Lakes, MN (US); Bradley J. Wessman, Wilmington, NC (US)

(73) Assignee: TranS1 Inc., Wilmington, NC (US)

( * ) Notice: Subject to any disclaimer, the term of this patent is extended or adjusted under 35 U.S.C. 154(b) by 1353 days.

(21) Appl. No.: 11/586,486

(22) Filed: Oct. 24, 2006

(65) Prior Publication Data

US 2007/0167951 A1 Jul. 19, 2007

Related U.S. Application Data

(63) Continuation-in-part of application No. 11/256,810, filed on Oct. 24, 2005, now Pat. No. 7,601,171, application No. 11/586,486, which is a continuation-in-part of application No. 11/259,614, filed on Oct. 25, 2005, and a continuation-in-part of application No. 10/972,184, filed on Oct. 22, 2004, now Pat. No. 7,717,958, application No. 11/586,486, which is a continuation-in-part of application No. 10/972,039, filed on Oct. 22, 2004, now Pat. No. 7,491,236, application No. 11/586,486, which is a continuation-in-part of application No. 10/972,040, filed on Oct. 22, 2004, now Pat. No. 7,662,173, application No. 11/586,486, which is a continuation-in-part of application No. 10/972,176, filed on Oct. 22, 2004, now Pat. No. 7,547,324, said application No. 11/256,810 is a continuation-in-part of application No. 11/199,541, filed on Aug. 8, 2005.

(60) Provisional application No. 60/621,148, filed on Oct. 22, 2004, provisional application No. 60/621,730, filed on Oct. 25, 2004, provisional application No. 60/558,069, filed on Mar. 31, 2004, provisional application No. 60/513,899, filed on Oct. 23, 2003, provisional application No. 60/599,989, filed on Aug. 9, 2004.

(51) Int. Cl.
*A61B 17/70* (2006.01)

(52) U.S. Cl. .................................. 606/86 A; 606/99

(58) Field of Classification Search ............... 606/86 A, 606/99, 104
See application file for complete search history.

(56) References Cited

U.S. PATENT DOCUMENTS 640,661 A 1/1900 Johnstone .................. 411/380
(Continued)

FOREIGN PATENT DOCUMENTS
WO WO 9100713 A1 1/1991

*Primary Examiner* — Nicholas Woodall
(74) *Attorney, Agent, or Firm* — The Eclipse Group LLP; Kevin E. Flynn

(57) ABSTRACT

A driver for delivering an insert to a bone anchor, the bone anchor having an internal cavity with a set of internal threads, the driver adapted to rotate with respect to a bone anchor that is anchored in a vertebral body in order to engage external threads on the insert with the set of internal threads in the bone anchor and axially advance the threadedly engaged insert within the bone anchor while simultaneously preventing the bone anchor from rotating with respect to the vertebral body the driver having: 1) a threaded retention rod for engaging a bore in the insert; 2) a driver head to engage with the insert to apply torque to the insert and rotate the insert; and 3) an anchor stabilizer to engage with a proximal face of the bone anchor to prevent the bone anchor from rotating with respect to the vertebral body.

4 Claims, 40 Drawing Sheets

U.S. PATENT DOCUMENTS

| | | | |
|---|---|---|---|
| 1,007,107 A * | 10/1911 | Hulsmann | 81/447 |
| 1,029,104 A | 6/1912 | Clark | 411/379 |
| 1,079,224 A | 11/1913 | Dodds | 411/380 |
| 1,086,144 A | 2/1914 | Dodds | 411/379 |
| 1,111,691 A | 9/1914 | Flannery | 411/380 |
| 2,586,556 A | 2/1952 | Mullikin | |
| 3,272,541 A | 9/1966 | Latzen | 403/138 |
| 3,367,326 A | 2/1968 | Frazier | 606/86 A |
| 3,837,347 A | 9/1974 | Tower | |
| 4,175,555 A | 11/1979 | Herbert | 606/304 |
| 4,276,874 A | 7/1981 | Wolvek et al. | |
| 4,297,047 A | 10/1981 | Farrant | 403/138 |
| 4,309,777 A | 1/1982 | Patil | |
| 4,636,217 A | 1/1987 | Ogilvie et al. | |
| 4,854,797 A | 8/1989 | Gourd | |
| 4,858,601 A | 8/1989 | Glisson | |
| 4,875,794 A | 10/1989 | Kern, Jr. | 403/132 |
| 4,932,925 A | 6/1990 | Roinestad et al. | 474/206 |
| 4,932,975 A | 6/1990 | Main et al. | 623/17.12 |
| 4,936,848 A * | 6/1990 | Bagby | 623/17.16 |
| 5,002,576 A | 3/1991 | Fuhrmann et al. | |
| 5,059,193 A | 10/1991 | Kuslich | |
| 5,061,137 A | 10/1991 | Gourd | |
| 5,102,276 A | 4/1992 | Gourd | |
| 5,108,430 A | 4/1992 | Ravo | |
| 5,139,499 A * | 8/1992 | Small et al. | 606/301 |
| 5,246,458 A | 9/1993 | Graham | |
| 5,338,297 A | 8/1994 | Kocur et al. | |
| 5,360,430 A | 11/1994 | Lin | 606/247 |
| 5,433,739 A | 7/1995 | Sluijter et al. | 607/99 |
| 5,480,401 A | 1/1996 | Navas | 616/256 |
| 5,562,737 A | 10/1996 | Graf | 623/17.14 |
| 5,649,931 A * | 7/1997 | Bryant et al. | 606/104 |
| 5,702,453 A | 12/1997 | Rabbe et al. | |
| 5,733,284 A | 3/1998 | Martin | |
| 5,743,912 A | 4/1998 | Lehille et al. | |
| 5,827,285 A | 10/1998 | Bramlet | |
| 6,056,749 A | 5/2000 | Kuslich | 606/86 A |
| 6,063,121 A | 5/2000 | Xavier et al. | 623/17.15 |
| 6,077,267 A * | 6/2000 | Huene | 606/916 |
| 6,086,589 A | 7/2000 | Kuslich et al. | 606/247 |
| 6,093,205 A | 7/2000 | McLeod et al. | |
| 6,187,048 B1 | 2/2001 | Milner et al. | |
| 6,190,413 B1 | 2/2001 | Sutcliffe | 623/17.11 |
| 6,235,043 B1 | 5/2001 | Reiley et al. | |
| 6,258,090 B1 | 7/2001 | Jackson | 606/61 |
| 6,428,576 B1 | 8/2002 | Haldimann | 623/17.16 |
| 6,440,168 B1 | 8/2002 | Cauthen | |
| 6,506,194 B1 | 1/2003 | Hajianpour | |
| 6,558,390 B2 | 5/2003 | Cragg | 606/80 |
| 6,582,466 B1 | 6/2003 | Gauchet | |
| 6,582,468 B1 | 6/2003 | Gauchet | |
| 6,626,943 B2 | 9/2003 | Eberlein et al. | |
| 6,656,184 B1 | 12/2003 | White et al. | |
| 6,682,561 B2 | 1/2004 | Songer et al. | |
| 6,692,495 B1 | 2/2004 | Zacouto | |
| 6,730,088 B2 | 5/2004 | Yeh | 606/61 |
| 6,733,532 B1 | 5/2004 | Gauchet et al. | |
| 6,764,489 B2 | 7/2004 | Feree | |
| 6,821,277 B2 | 11/2004 | Teitelbaum | |
| 6,899,716 B2 | 5/2005 | Cragg | 606/86 R |
| 6,899,719 B2 | 5/2005 | Reiley et al. | 606/192 |
| 6,964,665 B2 | 11/2005 | Thomas et al. | |
| 7,048,717 B1 | 5/2006 | Frassica | |
| 7,077,865 B2 | 7/2006 | Bao et al. | |
| 7,156,877 B2 | 1/2007 | Lotz et al. | |
| 7,291,150 B2 | 11/2007 | Graf | |
| 7,361,192 B2 | 4/2008 | Doty | 623/17.12 |
| 7,419,505 B2 | 9/2008 | Fleischmann et al. | 623/17.11 |
| 7,491,236 B2 | 2/2009 | Cragg et al. | 623/17.11 |
| 7,547,324 B2 | 6/2009 | Cragg et al. | |
| 7,766,917 B2 * | 8/2010 | Kugler et al. | 606/86 R |
| 2001/0021852 A1 | 9/2001 | Chappius | |
| 2002/0035400 A1 | 3/2002 | Bryan et al. | |
| 2002/0068975 A1 | 6/2002 | Teitelbaum et al. | |
| 2002/0198527 A1 | 12/2002 | Muckter | |
| 2003/0028193 A1 | 2/2003 | Weil et al. | |
| 2003/0055427 A1 | 3/2003 | Graf | 606/61 |
| 2003/0114930 A1 | 6/2003 | Lim et al. | 623/17.11 |
| 2003/0204261 A1 | 10/2003 | Eisermann et al. | |
| 2004/0083002 A1 | 4/2004 | Belef et al. | |
| 2004/0210227 A1 | 10/2004 | Trail et al. | 606/73 |
| 2004/0230309 A1 | 11/2004 | DiMauro et al. | |
| 2005/0043796 A1 | 2/2005 | Grant et al. | |
| 2005/0113919 A1 | 5/2005 | Cragg et al. | |
| 2005/0113929 A1 | 5/2005 | Cragg et al. | |
| 2005/0149191 A1 | 7/2005 | Cragg et al. | |
| 2005/0177167 A1 | 8/2005 | Muckter | |
| 2005/0277940 A1 | 12/2005 | Neff | |
| 2006/0084983 A1 | 4/2006 | Kim | |
| 2006/0085073 A1 | 4/2006 | Raiszadeh | |
| 2006/0229609 A1 | 10/2006 | Wang | 606/61 |
| 2007/0168042 A1 | 7/2007 | Hudgins et al. | |
| 2007/0282443 A1 | 12/2007 | Globerman et al. | |

* cited by examiner

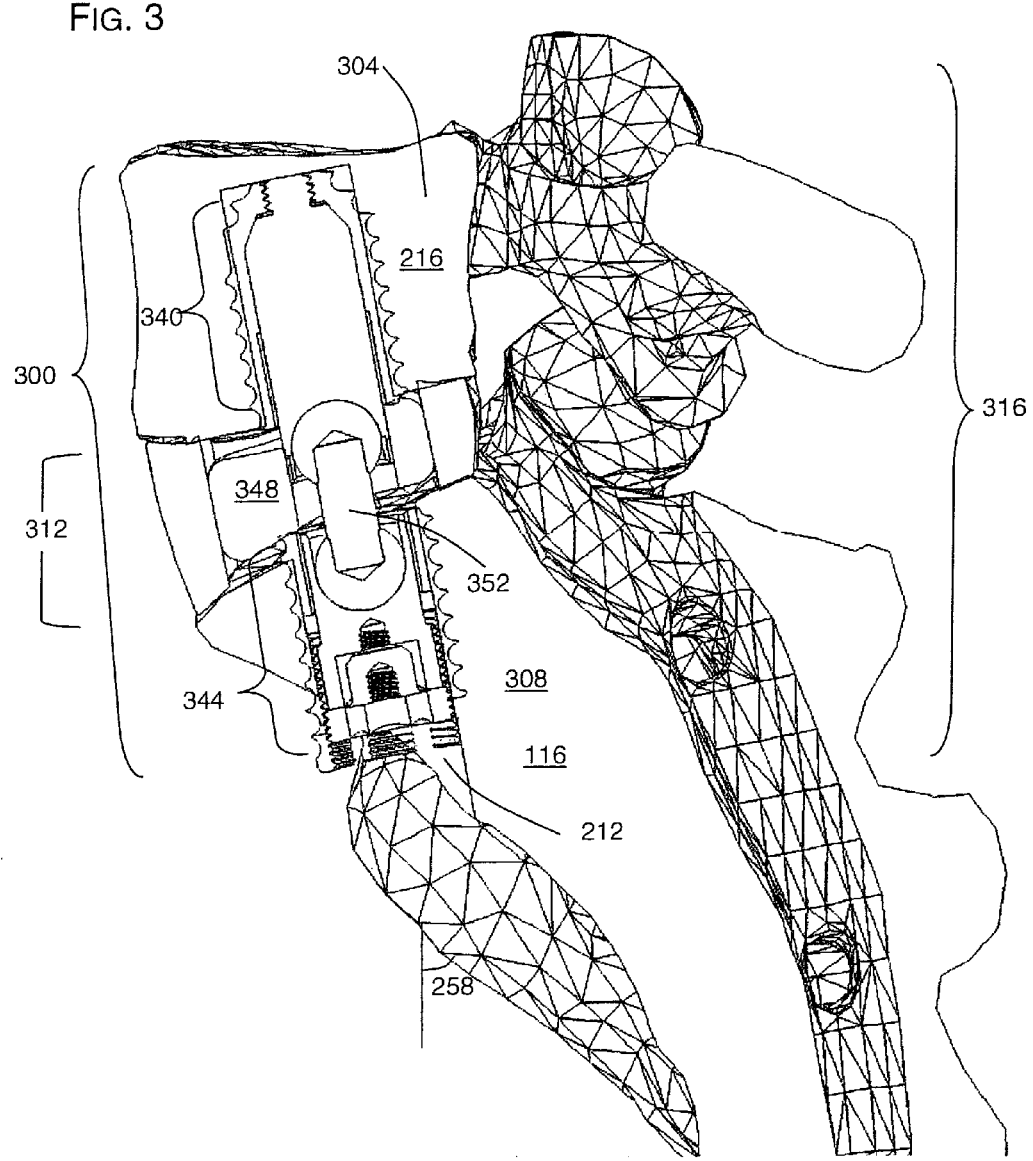

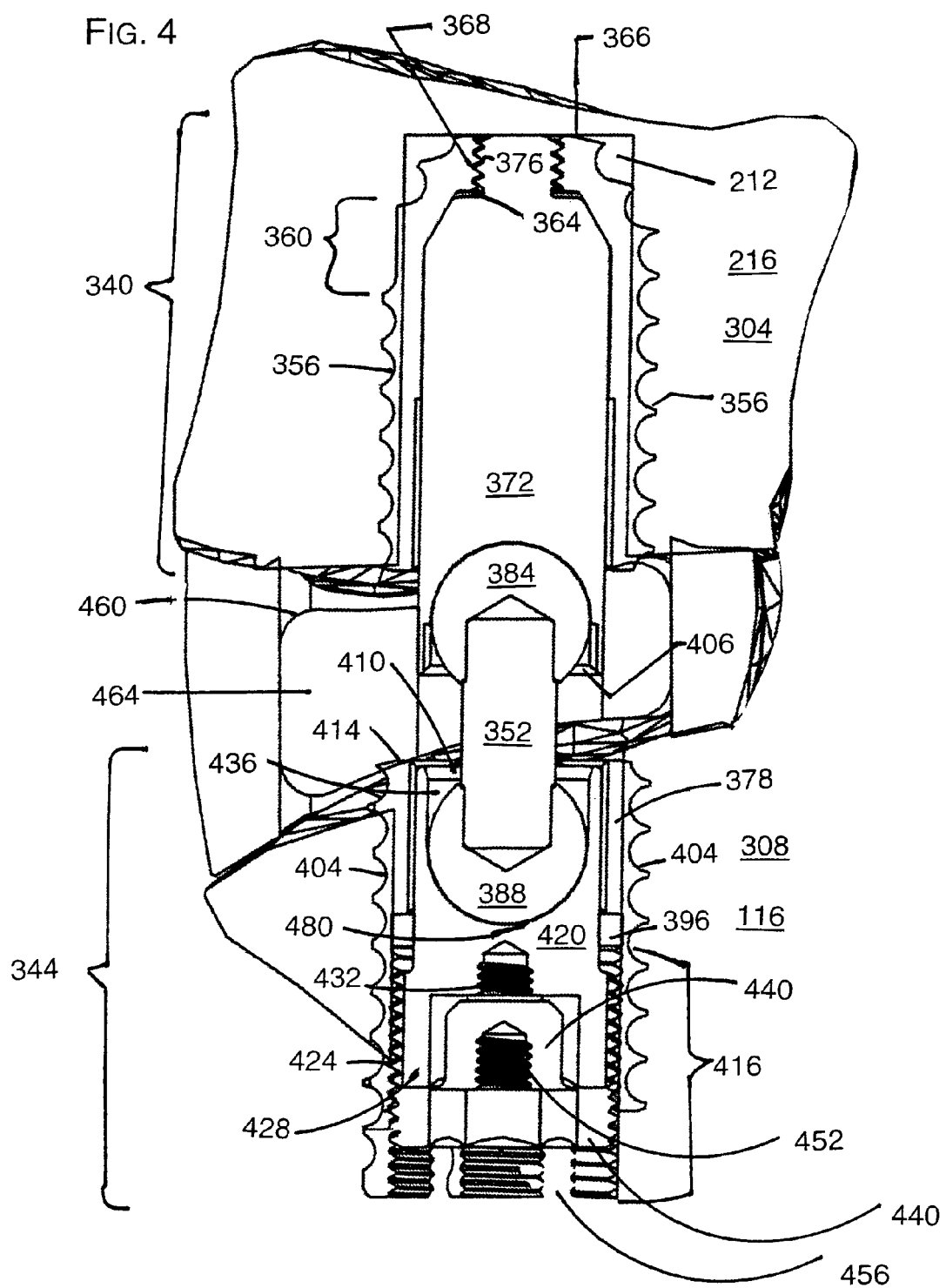

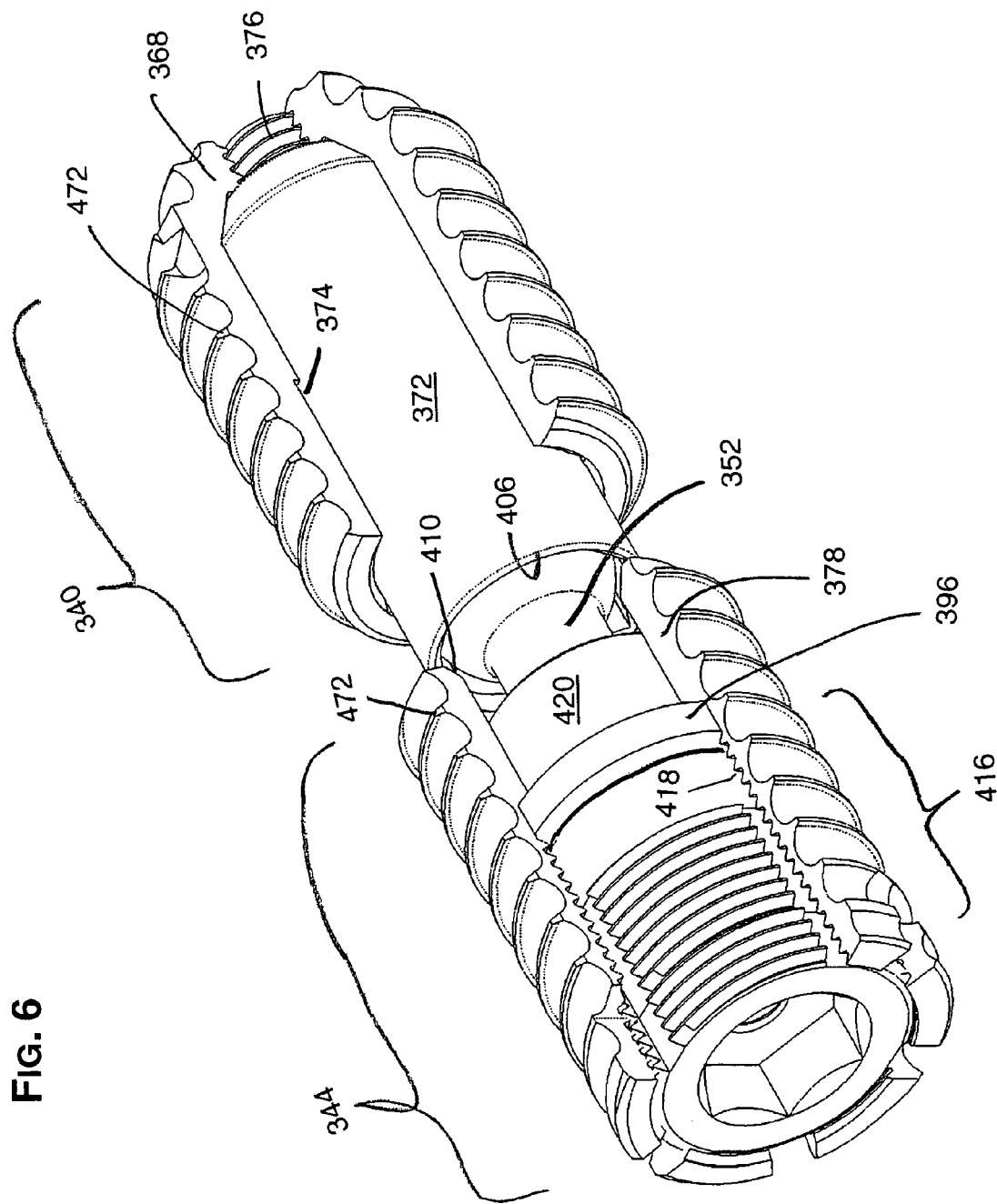

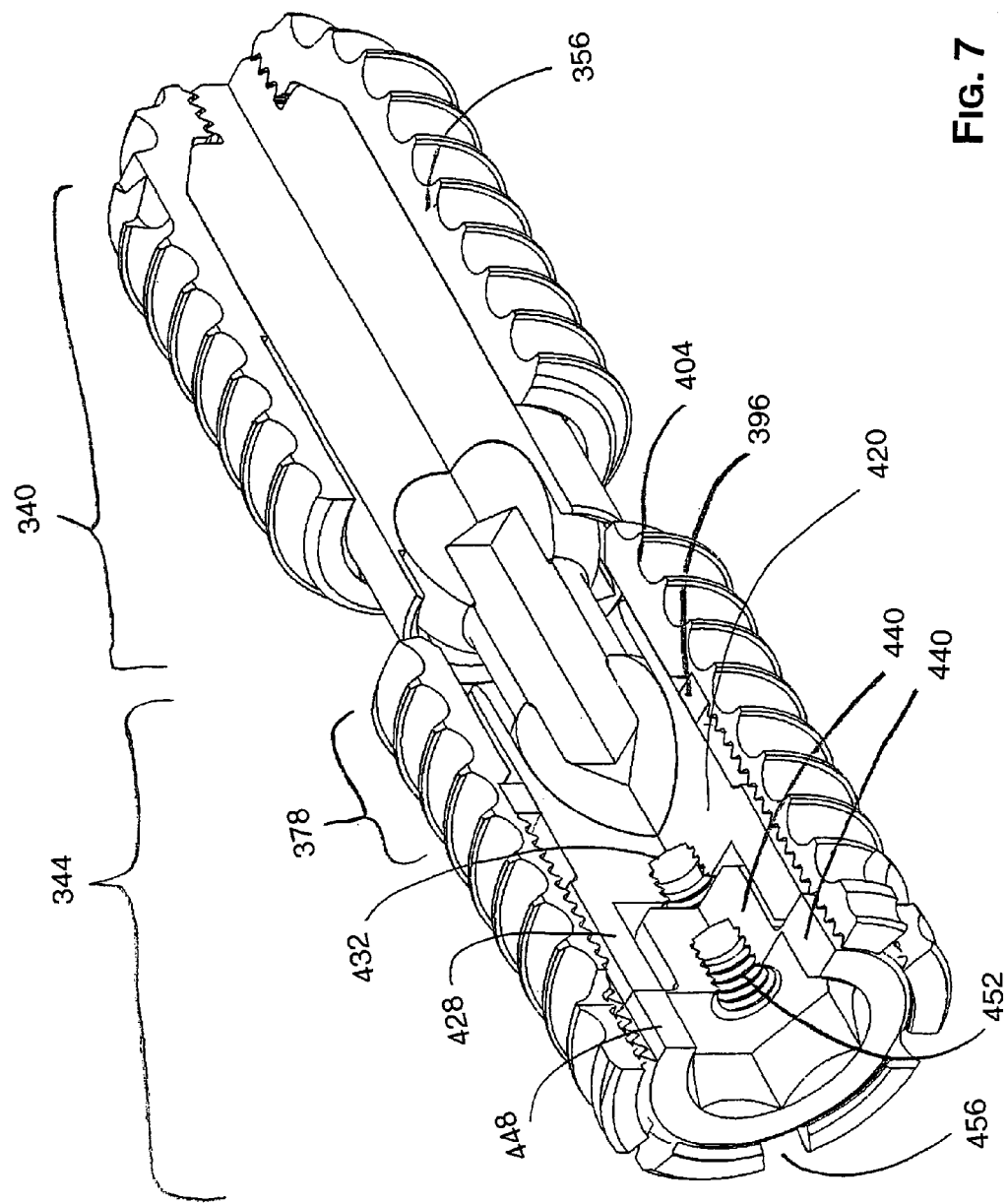

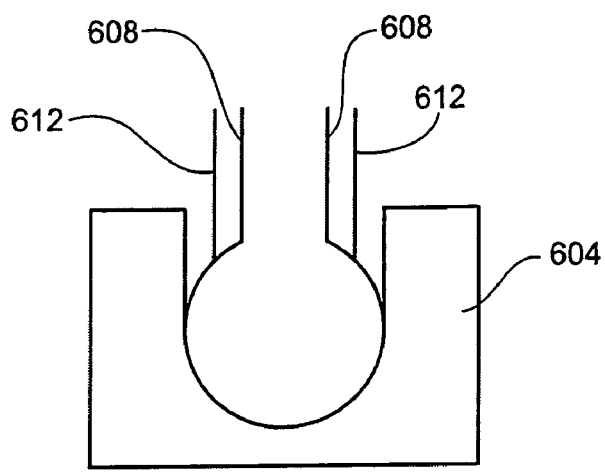
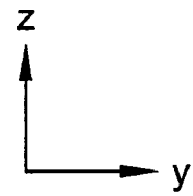
FIG. 8A
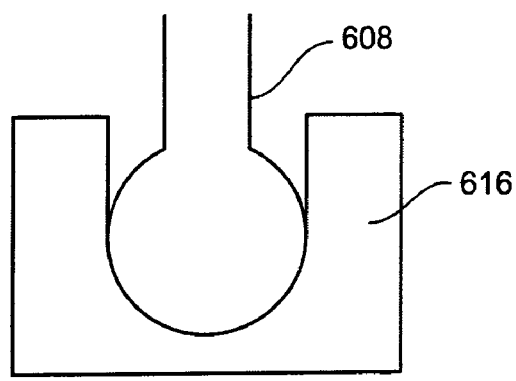
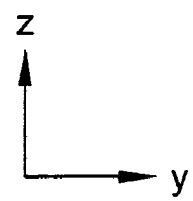
FIG. 8B
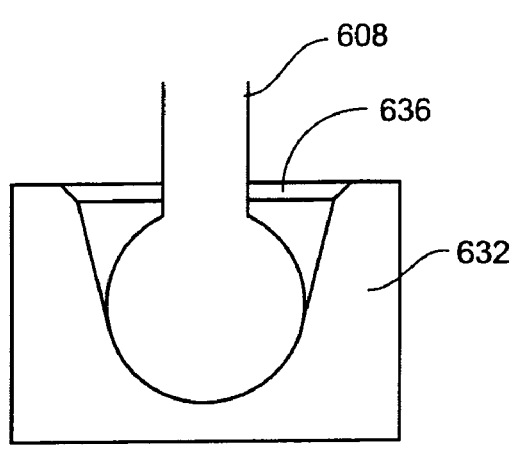
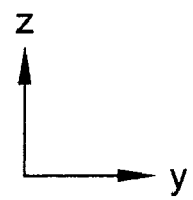
FIG. 8C

| FIG. 13A |
|---|
| FIG. 13B |
| FIG. 13C |
| FIG. 13D |

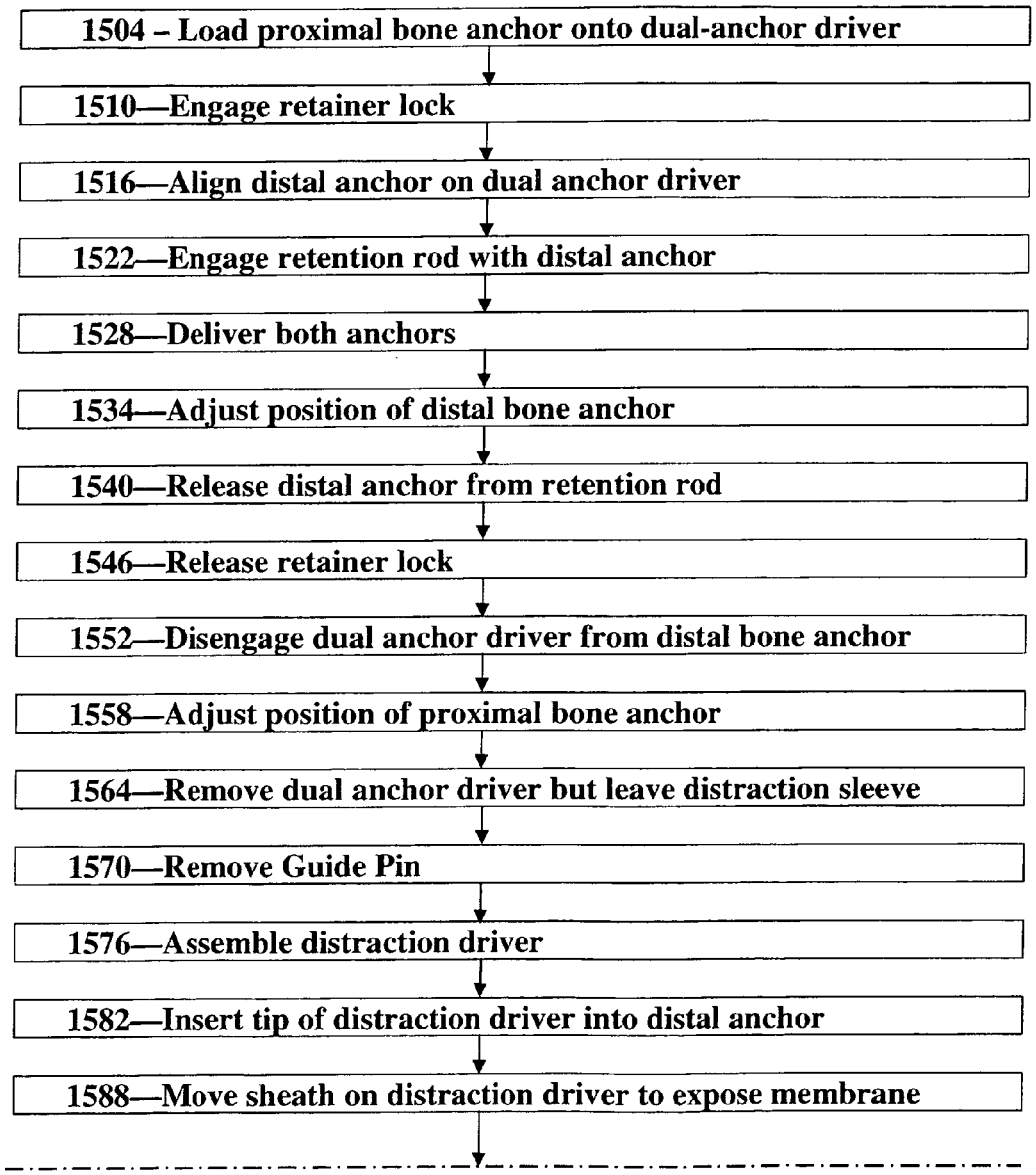

1504 – Load proximal bone anchor onto dual-anchor driver
1510 — Engage retainer lock
1516 — Align distal anchor on dual anchor driver
1522 — Engage retention rod with distal anchor
1528 — Deliver both anchors
1534 — Adjust position of distal bone anchor
1540 — Release distal anchor from retention rod
1546 — Release retainer lock
1552 — Disengage dual anchor driver from distal bone anchor
1558 — Adjust position of proximal bone anchor
1564 — Remove dual anchor driver but leave distraction sleeve
1570 — Remove Guide Pin
1576 — Assemble distraction driver
1582 — Insert tip of distraction driver into distal anchor
1588 — Move sheath on distraction driver to expose membrane

FIG. 14B

- 1594—Use distraction driver to impose distraction
- 1600—Assemble Delivery tools for Prosthetic Nucleus Material
- 1606—Inject material
- 1612—Allow prosthetic nucleus material to cure
- 1618—Disengage Distraction Sleeve
- 1624—Pull Distraction Driver to separate from Prosthetic Nucleus
- 1630—Load Distal Cup on Driver
- 1636—Insert Distal Cup
- 1642—Release Distal Cup from Driver
- 1648—Remove Distal Cup Driver
- 1654—Load Support Member into Driver
- 1660—Insert Driver into Proximal Bone Anchor
- 1666—Insert Support Member into Distal Cup
- 1672—Remove Support Member Driver
- 1678—Insert Dual Anchor Driver to Engage Proximal Anchor
- 1684—Remove Distraction Sleeve
- 1690—Place Proximal Anchor Stabilizer on Dual Use Driver

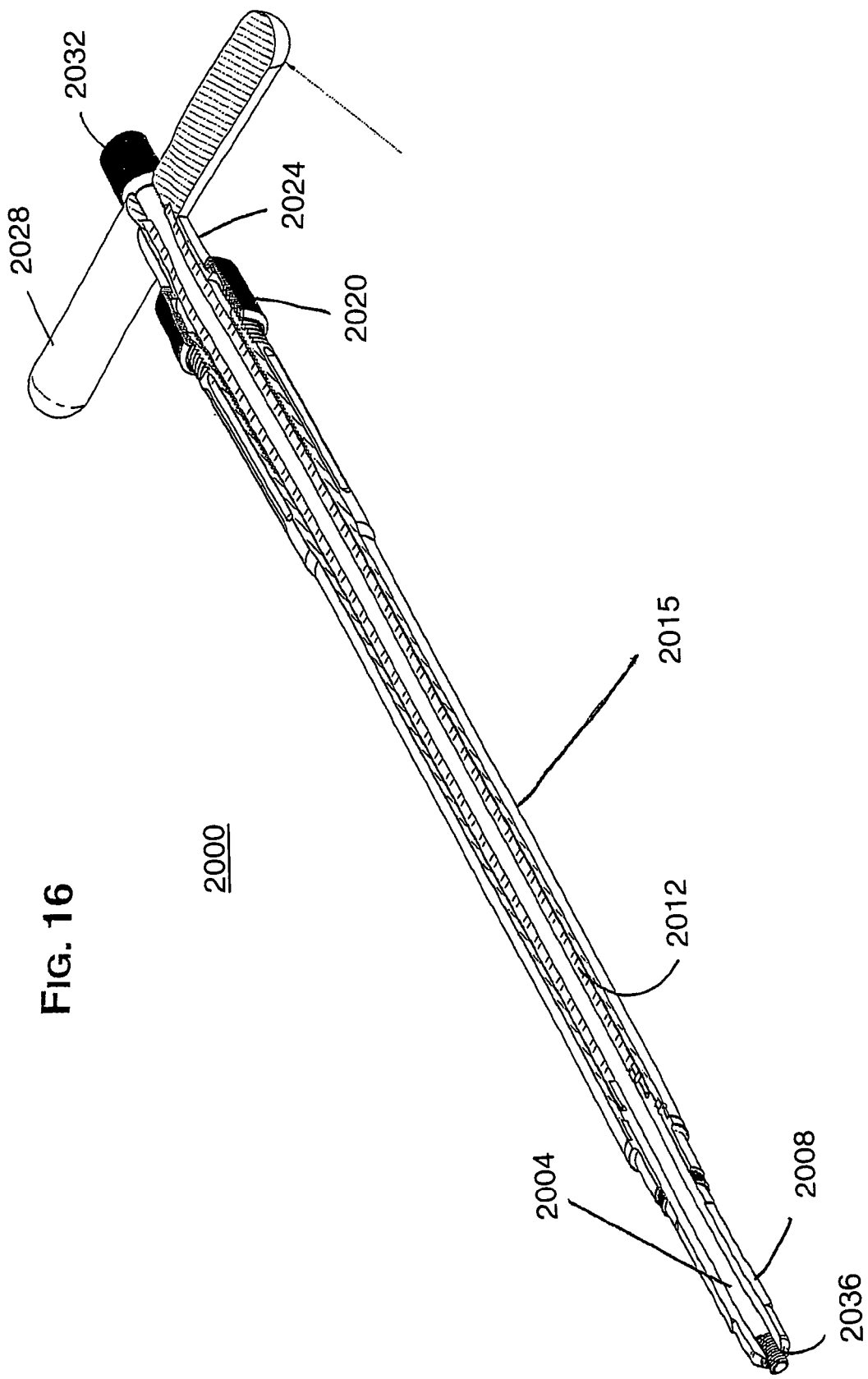

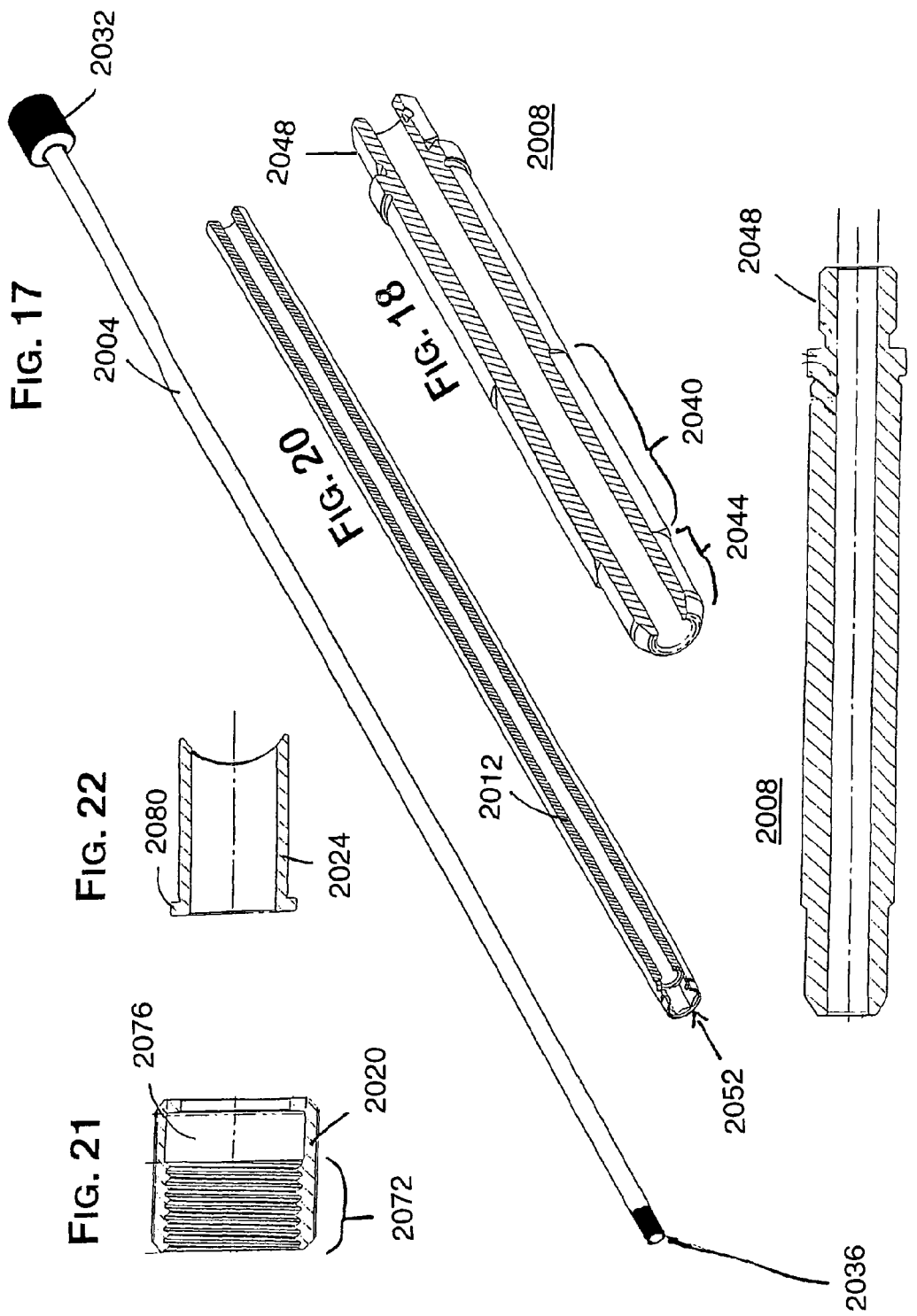

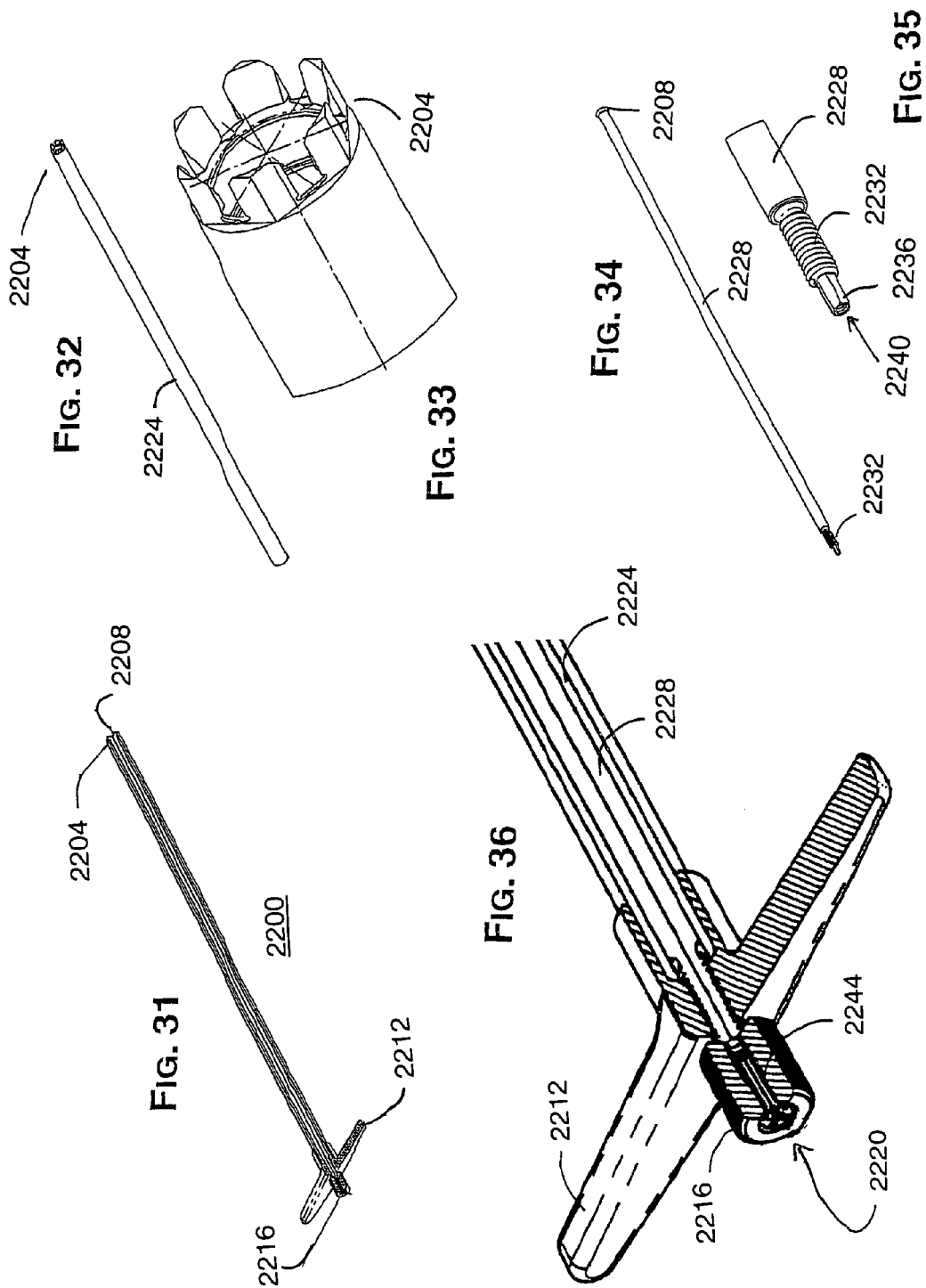

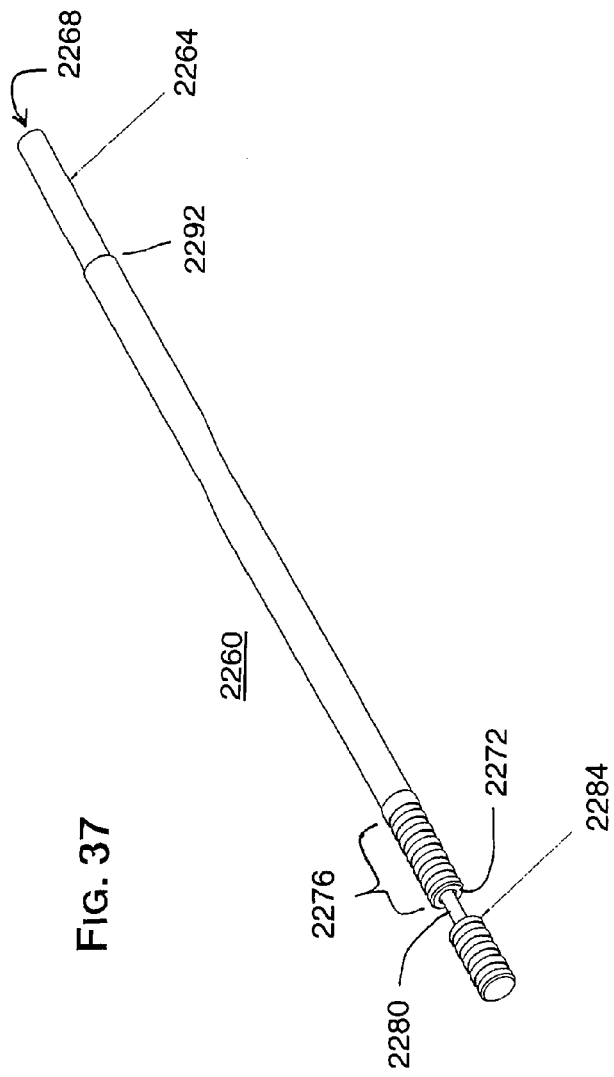
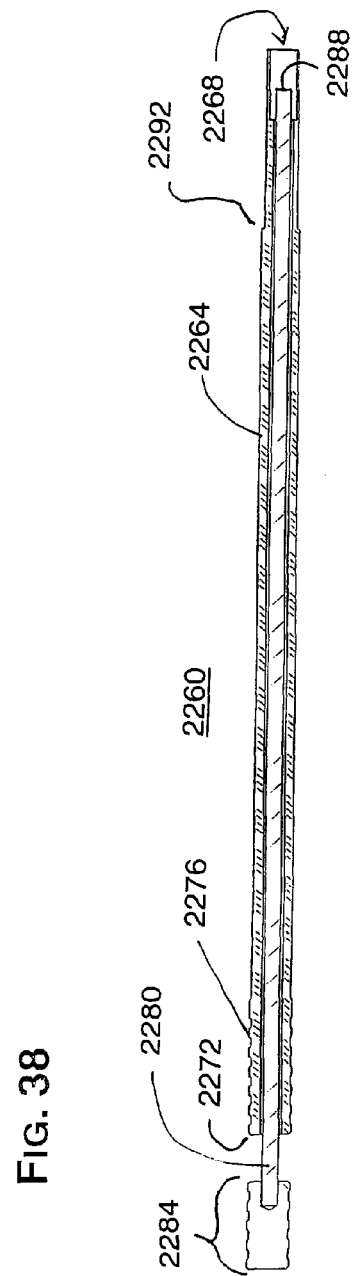
FIG. 37
FIG. 38

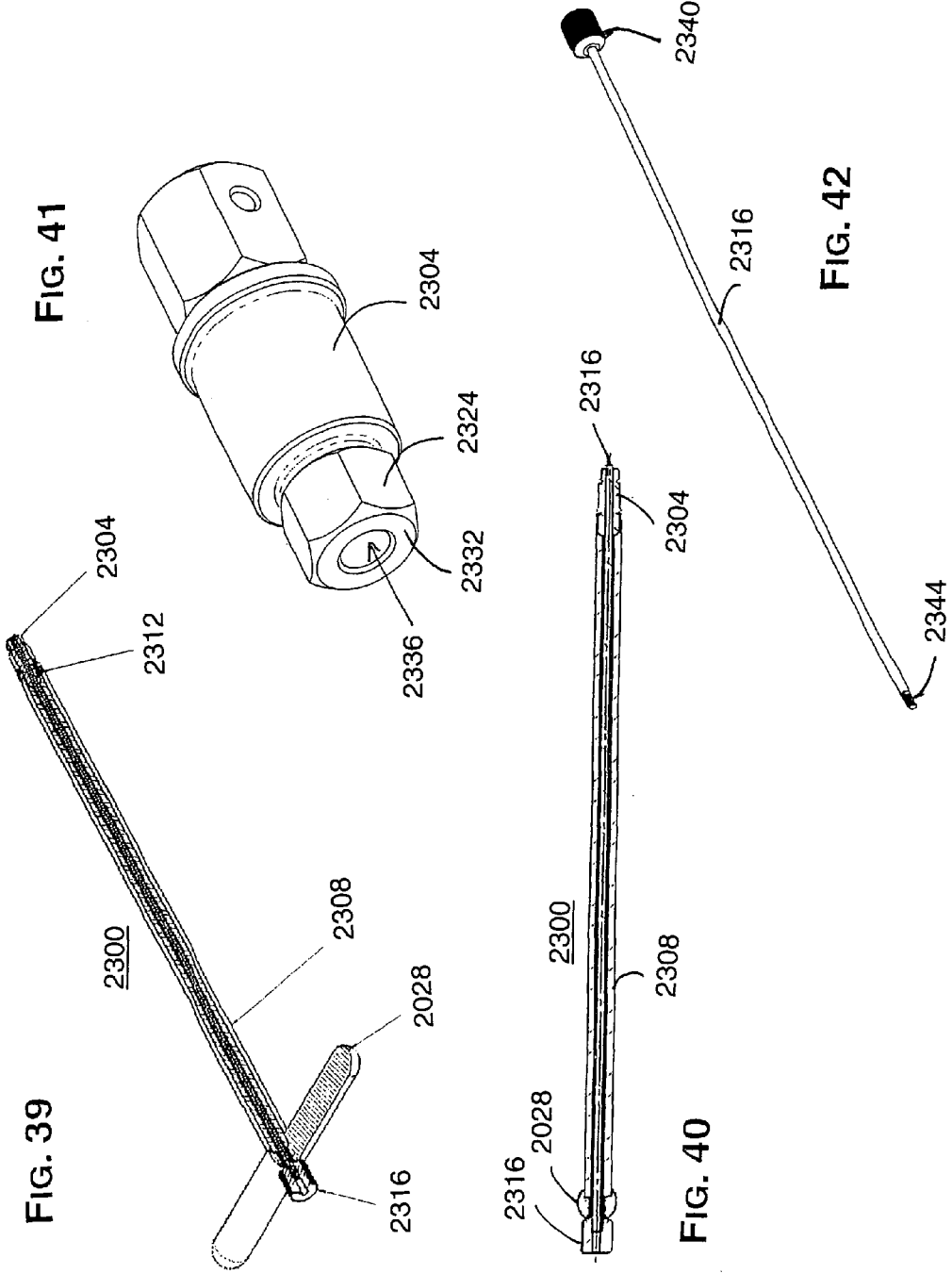

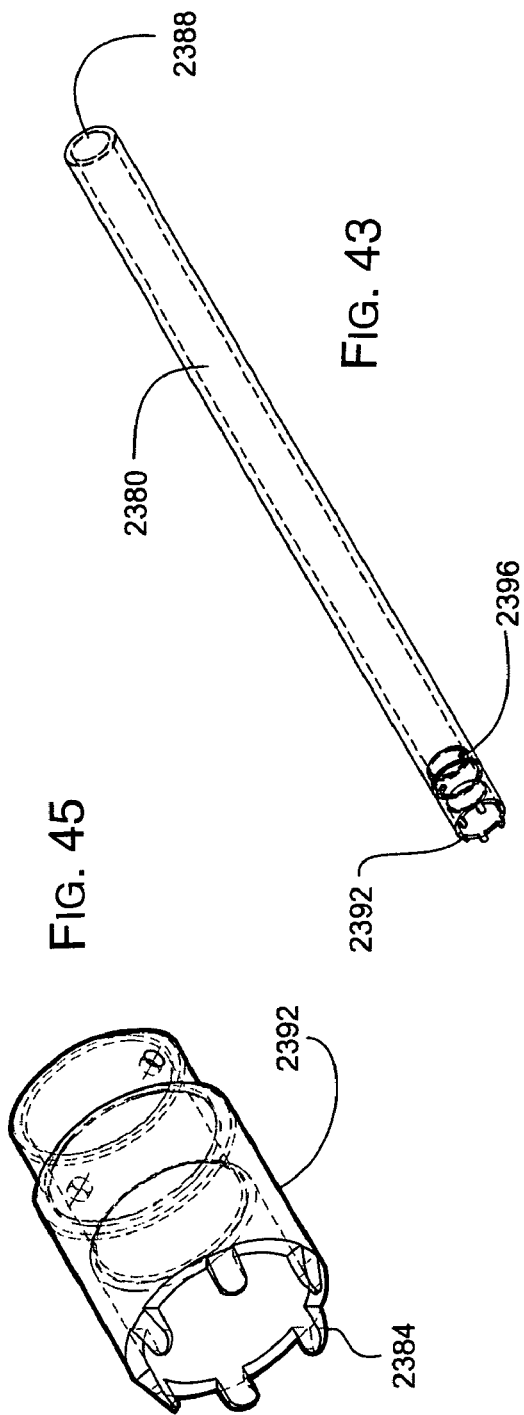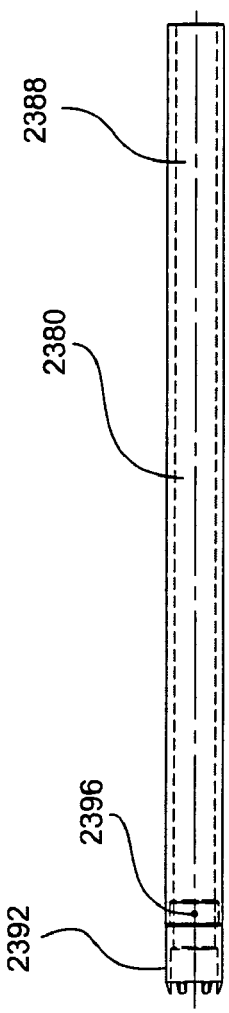

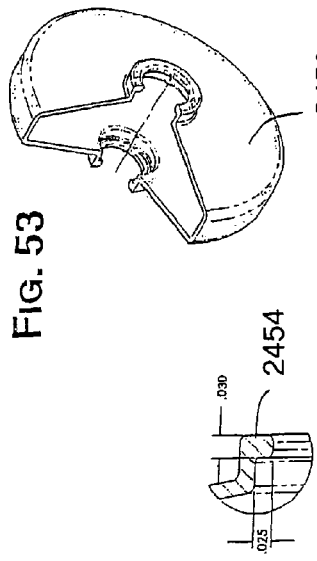
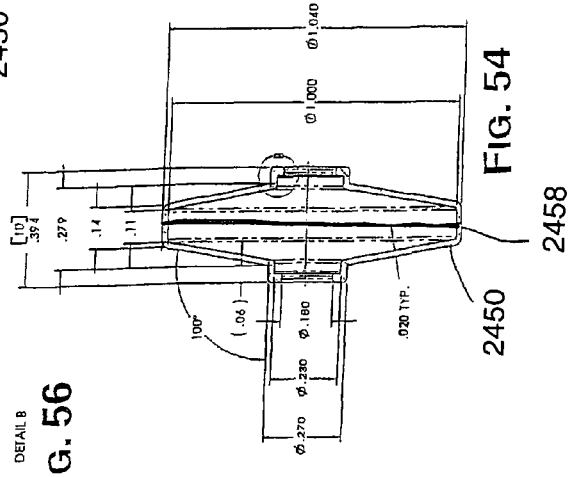
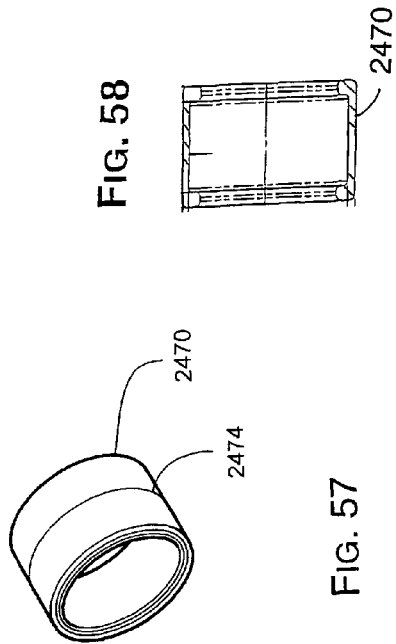
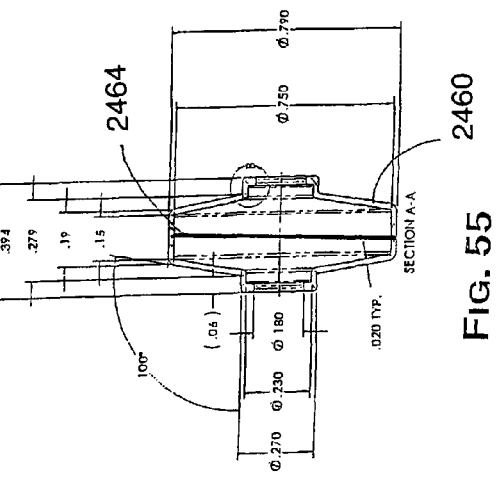

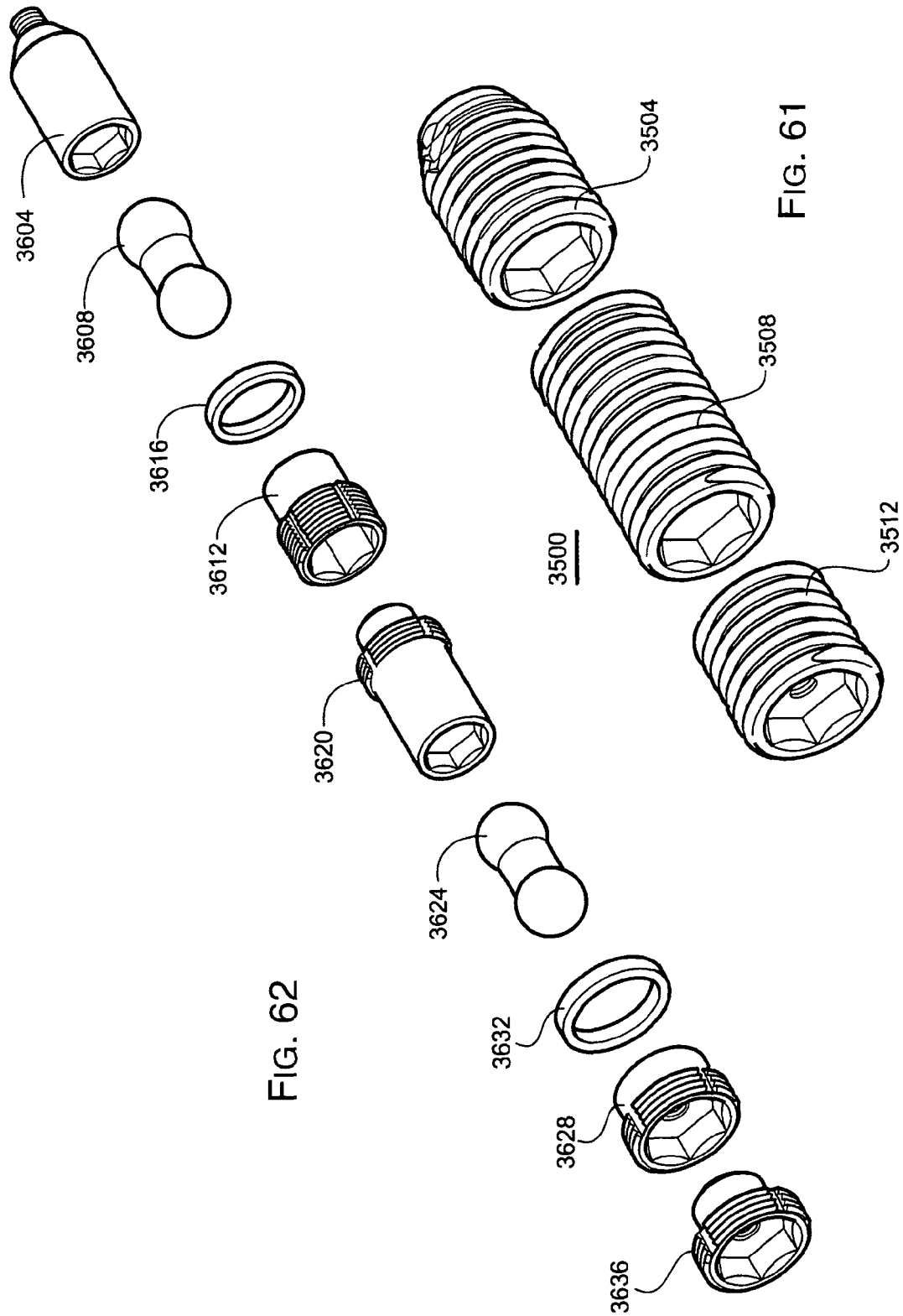

DRIVERS FOR INSERTS TO BONE ANCHORS

BACKGROUND OF THE INVENTION

This application builds upon a series of applications filed on behalf of assignee. In particular this application extends the innovative work in the area of spinal motion preservation assemblies described in and commonly assigned U.S. patent application Ser. No. 11/256,810 for Spinal Motion Preservation Assemblies and U.S. patent application Ser. No. 11/259,614 Driver Assembly for Simultaneous Axial Delivery of Spinal Implants. This application claims priority and incorporates by reference both the '810 application and the '614 application. This application claims priority and incorporates by reference two provisional applications claimed as priority documents by the '810 application specifically, U.S. Provisional Application No. 60/621,148 filed Oct. 22, 2004 for Spinal Mobility Preservation Assemblies and U.S. Provisional Application No. 60/621,730 filed Oct. 25, 2004 for Multi-Part Assembly for Introducing Axial Implants into the Spine. This application claims priority and incorporates by reference four co-pending and commonly assigned U.S. patent application Ser. Nos. 10/972,184, 10/972,039, 10/972,040, and 10/972,176 all filed on Oct. 22, 2004. These four applications claim priority to two United States Provisional Applications: Application No. 60/558,069 filed Mar. 31, 2004 and Application No. 60/513,899 filed Oct. 23, 2003. Priority to these two provisionals is claimed through the four co-pending applications and the provisionals are incorporated by reference. This application also claims priority through the '810 application to U.S. patent application Ser. No. 11/199,541 filed Aug. 8, 2005 and U.S. Provisional Application No. 60/599,989 filed Aug. 9, 2004 which is claimed as a priority document for the '541 application. Both of these applications are incorporated by reference.

This application incorporates by reference a set of United States applications, provisional applications, and issued patents including: 60/182,748 filed Feb. 16, 2000; Ser. No. 09/640,222 filed Aug. 16, 2000 (now issued as U.S. Pat. No. 6,575,979); Ser. No. 10/459,149 filed Jun. 11, 2003; Ser. No. 09/684,820 filed Oct. 10, 2000 (now issued as U.S. Pat. No. 6,558,386); Ser. No. 10/430,751 filed May 6, 2003; 60/182,748 filed Feb. 16, 2000; Ser. No. 09/782,583 filed Feb. 13, 2001 (issued as U.S. Pat. No. 6,558,390); Ser. No. 09/848,556 filed May 3, 2001 (now issued as U.S. Pat. No. 7,014,633); Ser. No. 10/125,771 filed Apr. 18, 2002 (issued as U.S. Pat. No. 6,899,716); Ser. No. 10/990,705 filed Nov. 17, 2004; Ser. No. 10/430,841 filed May 6, 2003; Ser. No. 09/710,369 filed Nov. 10, 2000 (issued as U.S. Pat. No. 6,740,090); Ser. No. 10/853,476 filed May 25, 2004; Ser. No. 09/709,105 filed Nov. 10, 2000 (issued as U.S. Pat. No. 6,790,210); Ser. No. 09/782,534 filed Feb. 13, 2001; application Ser. Nos. 10/971,779, 10/971,781, 10/971,731, 10/972,077, 10/971,765, 10/972,065, 10/971,775, 10/971,299, 10/971,780, all filed Oct. 22, 2004; 60/706,704 filed Aug. 9, 2005; Ser. No. 11/189,943 filed Jul. 26, 2005, Ser. No. 10/309,416 now U.S. Pat. No. 6,921,403 filed Dec. 3, 2002. While these applications have been incorporated by reference to provide additional detail it should be noted that these other applications (including those that have subsequently issued as patents) were written at an earlier time and had a different focus from the present application. Thus, to the extent that the teachings or use of terminology differ in any of these incorporated applications from the present application, the present application controls.

FIELD OF THE INVENTION

The present invention relates generally to implantable device assemblies, instrumentation systems, and methods for accessing and treating a spinal motion segment via various access routes including a minimally-invasive trans-sacral approach (as described in U.S. Pat. No. 6,558,390 which is incorporated herein by reference) and procedures for the deployment of implantable components and assemblies that are anchored in bone that can be used to distract, decompress, and stabilize while preserving motion in vertebral motion segments in the human spine to relieve lower back pain, restore physiological function of the lumbar spine, and prevent progression or transition of degenerative disease. More specifically, the present disclosure generally relates to spinal motion preservation assemblies (MPA) including assemblies adapted to be introduced percutaneously through tissue to an access point on the spine in a minimally invasive, low trauma manner, to provide therapy to the spine.

BACKGROUND OF THE INVENTION

Overview

The present invention is an extension of work in a series of patent applications (some now issued patents) with a common assignee. Much of the work is described in great detail in the many applications referenced above and incorporated by reference into this application. Accordingly, the background of the invention provided here does not repeat all of the detail provided in the earlier applications, but instead highlights how the present invention adds to this body of work.

The spinal column is a complex system of bone segments (vertebral bodies and other bone segments) which are in most cases separated from one another by discs in the intervertebral spaces (sacral vertebrae are an exception). FIG. 1 shows the various segments of a human spinal column as viewed from the side. In the context of the present disclosure, a "motion segment" includes adjacent vertebrae, i.e., an inferior and a superior vertebral body, and the intervertebral disc space separating said two vertebral bodies, whether denucleated space or with intact or damaged spinal discs. Unless previously fused, each motion segment contributes to the overall flexibility of the spine to flex to provide support for the movement of the trunk and head.

The vertebrae of the spinal cord are conventionally subdivided into several sections. Moving from the head to the tailbone, the sections are cervical 104, thoracic 108, lumbar 112, sacral 116, and coccygeal 120. The individual vertebral bodies within the sections are identified by number starting at the vertebral body closest to the head. The trans-sacral approach is well suited for access to vertebral bodies in the lumbar section and the sacral section. As the various vertebral bodies in the sacral section are usually fused together in adults, it is sufficient and perhaps more descriptive to merely refer to the sacrum rather than the individual sacral components.

It is useful to set forth some of the standard medical vocabulary before getting into a more detailed discussion of the background of the present invention. In the context of the this discussion: anterior refers to in front of the spinal column; (ventral) and posterior refers to behind the column (dorsal); cephalad means towards the patient's head (sometimes "superior"); caudal (sometimes "inferior") refers to the direction or location that is closer to the feet. As the present application contemplates accessing the various vertebral bodies and intervertebral spaces through a preferred approach that comes in from the sacrum and moves towards the head, proximal and distal are defined in context of this channel of approach. Consequently, proximal is closer to the beginning of the channel and thus towards the feet or the surgeon, distal is further from the beginning of the channel and thus towards the head, or more distant from the surgeon. When referencing delivery tools, distal would be the end intended for insertion into the access channel and proximal refers to the other end, generally the end closer to the handle for the delivery tool.

The individual motion segments within the spinal column allow movement within constrained limits and provide protection for the spinal cord. The discs are important to cushion and distribute the large forces that pass through the spinal column as a person walks, bends, lifts, or otherwise moves. Unfortunately, for a number of reasons referenced below, for some people, one or more discs in the spinal column will not operate as intended. The reasons for disc problems range from a congenital defect, disease, injury, or degeneration attributable to aging. Often when the discs are not operating properly, the gap between adjacent vertebral bodies is reduced and this causes additional problems including pain.

It has been estimated that in 2004 there were over 700,000 surgical procedures performed annually to treat lower back pain in the U.S. It is conservatively estimated that in 2004 there were more than 200,000 lumbar fusions performed in the U.S., and more than 300,000 worldwide, representing approximately a $1B endeavor in an attempt to alleviate patients' pain. Approximately 60% of spinal surgery takes place in the lumbar spine, and of that portion approximately 80% involves the lower lumbar vertebrae designated as the fourth lumbar vertebra ("L4"), the fifth lumbar vertebra ("L5"), and the first sacral vertebra ("S1"). Persistent low back pain is often attributable to degeneration of the disc between L5 and S1. (See edge between the lumbar region 112 and the sacrum 116 in FIG. 1).

A range of therapies have been developed to alleviate the pain associated with disc problems. One class of solutions is to remove the failed disc and then fuse the two adjacent vertebral bodies together with a permanent but inflexible spacing, also referred to as static stabilization. As mentioned above, an estimated 300,000 fusion operations take place each year. Fusing one section together ends the ability to flex in that motion segment. While the loss of the normal physiologic disc function for a motion segment through fusion of a motion segment may be better than continuing to suffer from the pain, it would be better to alleviate the pain and yet retain all or much of the normal performance of a healthy motion segment.

Another class of therapies attempts to repair the disc so that it resumes operation with the intended intervertebral spacing and mechanical properties. One type of repair is the replacement of the original damaged disc with a prosthetic disc. This type of therapy is called by different names such as dynamic stabilization or spinal motion preservation.

The Operation of the Spine

The bodies of successive lumbar, thoracic and cervical vertebrae articulate with one another and are separated by the intervertebral spinal discs. Each spinal disc includes a fibrous cartilage shell enclosing a central mass, the "nucleus pulposus" (or "nucleus" herein) that provides for cushioning and dampening of compressive forces to the spinal column. The shell enclosing the nucleus includes cartilaginous endplates adhered to the opposed cortical bone endplates of the cephalad and caudal vertebral bodies and the "annulus fibrosus" (or "annulus" herein) includes multiple layers of opposing collagen fibers running circumferentially around the nucleus pulposus and connecting the cartilaginous endplates. The natural, physiological nucleus includes hydrophilic (water attracting) mucopolysacharides and fibrous strands (protein polymers). The nucleus is relatively inelastic, but the annulus can bulge outward slightly to accommodate loads axially applied to the spinal motion segment.

The intervertebral discs are anterior to the spinal canal and located between the opposed end faces or endplates of a cephalad and a caudal vertebral body. The inferior articular processes articulate with the superior articular processes of the next succeeding vertebra in the caudal (i.e., towards the feet or inferior) direction. Several ligaments (supraspinous, interspinous, anterior and posterior longitudinal, and the ligamenta flava) hold the vertebrae in position yet permit a limited degree of movement. The assembly of two vertebral bodies, the interposed, intervertebral, spinal disc and the attached ligaments, muscles and facet joints is referred to as a "spinal motion segment".

The relatively large vertebral bodies located in the anterior portion of the spine and the intervertebral discs provide the majority of the weight bearing support of the vertebral column. Each vertebral body has relatively strong, cortical bone layer forming the exposed outside surface of the body, including the endplates, and weaker, cancellous bone in the center of the vertebral body.

The nucleus pulposus that forms the center portion of the intervertebral disc consists of 80% water that is absorbed by the proteoglycans in a healthy adult spine. With aging, the nucleus becomes less fluid and more viscous and sometimes even dehydrates and contracts (sometimes referred to as "isolated disc resorption") causing severe pain in many instances. The spinal discs serve as "dampeners" between each vertebral body that minimize the impact of movement on the spinal column, and disc degeneration, marked by a decrease in water content within the nucleus, renders discs ineffective in transferring loads to the annulus layers. In addition, the annulus tends to thicken, desiccate, and become more rigid, lessening its ability to elastically deform under load and making it susceptible to fracturing or fissuring, and one form of degeneration of the disc thus occurs when the annulus fissures or is torn. The fissure may or may not be accompanied by extrusion of nucleus material into and beyond the annulus. The fissure itself may be the sole morphological change, above and beyond generalized degenerative changes in the connective tissue of the disc, and disc fissures can nevertheless be painful and debilitating. Biochemicals contained within the nucleus are enabled to escape through the fissure and irritate nearby structures.

A fissure also may be associated with a herniation or rupture of the annulus causing the nucleus to bulge outward or extrude out through the fissure and impinge upon the spinal column or nerves (a "ruptured" or "slipped" disc). With a contained disc herniation, the nucleus may work its way partly through the annulus but is still contained within the annulus or beneath the posterior longitudinal ligament, and there are no free nucleus fragments in the spinal canal. Nevertheless, even a contained disc herniation is problematic because the outward protrusion can press on the spinal cord or on spinal nerves causing sciatica.

Another disc problem occurs when the disc bulges outward circumferentially in all directions and not just in one location. This occurs when, over time, the disc weakens bulges outward and takes on a "roll" shape. Mechanical stiffness of the joint is reduced and the spinal motion segment may become unstable, shortening the spinal cord segment. As the disc "roll" extends beyond the normal circumference, the disc height may be compromised, and foramina with nerve roots are compressed causing pain. Current treatment methods other than spinal fusion for symptomatic disc rolls and herniated discs include "laminectomy" which involves the surgical exposure of the annulus and surgical excision of the symptomatic portion of the herniated disc followed by a relatively lengthy recuperation period. In addition, osteophytes may form on the outer surface of the disc roll and further encroach on the spinal canal and foramina through which nerves pass. The cephalad vertebra may eventually settle on top of the caudal vertebra. This condition is called "lumbar spondylosis".

Various other surgical treatments that attempt to preserve the intervertebral spinal disc and to simply relieve pain include a "discectomy" or "disc decompression" to remove some or most of the interior nucleus thereby decompressing and decreasing outward pressure on the annulus. In less invasive microsurgical procedures known as "microlumbar discectomy" and "automated percutaneous lumbar discectomy", the nucleus is removed by suction through a needle laterally extended through the annulus. Although these procedures are less invasive than open surgery, they nevertheless suffer the possibility of injury to the nerve root and dural sac, perineural scar formation, re-herniation of the site of the surgery, and instability due to excess bone removal. In addition, they generally involve the perforation of the annulus.

Although damaged discs and vertebral bodies can be identified with sophisticated diagnostic imaging, existing surgical interventions and clinical outcomes are not consistently satisfactory. Furthermore, patients undergoing such fusion surgery experience significant complications and uncomfortable, prolonged convalescence. Surgical complications include disc space infection; nerve root injury; hematoma formation; instability of adjacent vertebrae, and disruption of muscle, tendons, and ligaments, for example.

Several companies are pursuing the development of prosthesis for the human spine, intended to completely replace a physiological disc, i.e., an artificial disc. In individuals where the degree of degeneration has not progressed to destruction of the annulus, rather than a total artificial disc replacement, a preferred treatment option may be to replace or augment the nucleus pulposus, involving the deployment of a prosthetic disc nucleus. As noted previously, the normal nucleus is contained within the space bounded by the bony vertebrae above and below it and the annulus fibrosus, which circumferentially surrounds it. In this way the nucleus is completely encapsulated and sealed with the only communication to the body being a fluid exchange that takes place through the bone interface with the vertebrae, known as the endplates.

The hydroscopic material found in the physiological nucleus has an affinity for water (and swells in volume) which is sufficiently powerful to distract (i.e., elevate or "inflate") the intervertebral disc space, despite the significant physiological loads that are carried across the disc in normal activities. These forces, which range from about 0.4× to about 1.8× body weight, generate local pressure well above normal blood pressure, and the nucleus and inner annulus tissue are, in fact, effectively avascular.

The existence of the nucleus as a cushion (e.g., the nucleus is the "air" in the "tire" known as a spinal disc), and the annulus, as a flexible member, contributes to the range of motion in the normal disc. Range of motion is described in terms of degrees of freedom (i.e., translation and rotation about three orthogonal planes relative to a reference point, the instantaneous center of rotation around the vertical axis of the spine). The advantages of spinal motion preservation assemblies of the present disclosure in preserving, restoring, and/or managing mobility in terms of flexion, extension, compression, left/right (L/R) rotation, L/R lateral bending, and distraction will become more apparent from the description of the relationship between movement and anatomical structures of the spine, and the consequences and impact of injury (e.g., trauma/mechanical injury or aging) noted below.

Flexion and Extension

Flexion and extension of the spine combine forward sliding and rotation of the vertebrae. The facet joints and the annulus resist the forward sliding. Rotation is resisted by the annulus; capsules of the facet joints; action of the back muscles, and passive tension generated by the thoracolumbar fascia. Extension is resisted by the facet joints, and secondarily by the annulus.

The spine is resistant to injury if the force is only in pure flexion, as the combination of the facet joints and disc are intrinsically stable in this plane. While the spinal muscles can be injured during forceful flexion since they are important in controlling this motion, ensuing pain is not typically chronic.

Extension is impaired by impaction of the facet joints and eventually the inferior articular process against the lamina. This can result in a cartilage injury of the facet joint, disruption of the facet capsule and facet joint, or pars interarticularis fracture.

Compression

Compression of the spine is due to body weight and loads applied to the spine. Body weight is a minor compressive load. The major compressive load on the spine is produced by the back muscles. As a person bends forward, the body weight plus an external load must be balanced by the force generated by the back muscles. That is, muscle loads balance gravitational loads so that the spine is in equilibrium to help keep us from falling over. The gravitational load to be offset may be calculated by multiplying the load times the perpendicular distance of the load from the spine. The greater the distance from the spine, the larger the load is. Since the back muscles act close to the spine, they must exert large forces to balance the load. The force generated by the back muscles results in compression of spinal structures.

Most of the compressive loads (~80%) are sustained by the anterior column (disc and vertebral body). The disc is a hydrostatic system. The nucleus acts as a confined fluid within the annulus. It distributes compressive forces from the vertebral end plates (axial loads) into tension on the annulus fibers.

Compression injuries occur by two main mechanisms; axial loading by gravity or by muscle action. Gravitational injuries result from a fall onto the buttocks while muscular injuries result from severe exertion during pulling or lifting. A serious potential consequence of the injury is a fracture of the vertebral end plate. Since the end plate is critical to disc nutrition, an injury can change the biochemical and metabolic state of the disc. If the end plate heals, the disc may suffer no long-term consequences. However, if the end plate does not heal, the nucleus can undergo harmful changes. The nucleus may lose its proteoglycans and thus its water-binding capacity. The hydrostatic properties of the nucleus may be compromised. Instead of sharing the load between the nucleus and the annulus, more of the load is transferred to the annulus. The annulus fibers may then fail. In addition to annular tears, the layers of the annulus may separate (delaminate). The disc may collapse or it may maintain its height with progressive annular tearing. If the annulus is significantly weakened, there may be a rupture of the disc whereby the nuclear material migrates into the annulus or into the spinal canal causing nerve root compression.

Rotation

Rotation of the spine is accomplished by the contraction of the abdominal muscles acting through the thorax and the thoracolumbar fascia. There are no primary muscles responsible for lumbar rotation. The facet joints and the collagen fibers of the annulus resist this rotation. In rotation, only 50% of the collagen fibers are in tension at any time, which renders the annulus susceptible to injury.

The spine is particularly susceptible to injury in a loading combination of rotation and flexion. Flexion pre-stresses the annular fibers. As the spine rotates, compression occurs on the facet joint surfaces of the joint opposite the rotation. Distraction occurs on the facet joint on the same side of the rotation. The center of rotation of the motion segment shifts from the back of the disc to the facet joint in compression. The disc shifts sideways and shear forces on the annular fibers are significant. Since the annular fibers are weak in this direction, they can tear. If the rotation continues, the facet joints can sustain cartilage injury, fracture, and capsular tears while the annulus can tear in several different ways. Any of these injuries can be a source of pain.

Lateral Bending

Bending is a combination of lateral flexion and rotation through the annulus and facet joints.

Distraction

Pure distraction rarely occurs and is usually a combination of tension and compression on the spinal joints depending on the direction of applied force. An example of a distraction force is therapeutic spinal traction to "unload" the spine.

In the context of the present disclosure, as used herein the term distraction refers procedurally to an elevation in height that increases the intervertebral disc space resulting from introduction of the motion preservation assembly or prosthetic nucleus device ("PND"), which may be achieved either in the axial deployment of the device itself, or assisted by means of a temporary distraction during the implantation procedure. Temporary distraction refers to elevation of disc height by means, such as a distraction device, which is subsequently removed but wherein the elevation is retained intra-operatively, while the patient remains prone. Thus, the device may be inserted into an elevated disc space first created by other distraction means, and thereafter physical presence and dimensionality of the inserted device is key to preserving that height space, to decompress the disc and alleviate pain caused by nerve impingement.

Thus, if one takes a reference point at the top face of a vertebral body, the motion segment includes that vertebral body, the next most cephalad vertebral body, and the intervertebral disc between those two vertebral bodies has six degrees of freedom. If the X axis is aligned with the anterior/posterior direction, and the Y axis is aligned with the right and left side, and the Z axis aligned with the cephalad/caudal direction (sometimes called the cephalad/caudal axis) then the six degrees of freedom are as follows:

| Translation along | X axis | Movement of upper vertebral body in anterior/posterior direction |
|---|---|---|
| Translation along | Y axis | Movement of upper vertebral body to right or to left |
| Translation along | Z axis | Movement of upper vertebral body away from lower vertebral body (distraction) or towards lower vertebral body compression |
| Rotation in plane defined by | X and Y | Rotation of spine clockwise or counterclockwise |
| Rotation in plane defined by | X and Z | Rotation of spine to flex or extend the spine |
| Rotation in plane defined by | Y and Z | Rotation of spine to move laterally to right or left |

To date, drawbacks of currently contemplated or deployed prosthetic nucleus devices include subsidence; their tendency to extrude or migrate; to erode the bone; to degrade with time, or to fail to provide sufficient biomechanical load distribution and support. Some of these drawbacks relate to the fact that their deployment typically involves a virtually complete discectomy of the disc achieved by instruments introduced laterally through the patient's body to the disc site and manipulated to cut away or drill lateral holes through the disc and adjoining cortical bone. The endplates of the vertebral bodies, which include very hard cortical bone and help to give the vertebral bodies needed strength, are usually weakened or destroyed during the drilling. The vertebral endplates are special cartilage structures that surround the top and bottom of each vertebra and are in direct contact with the disc. They are important to the nutrition of the disc because they allow the passage of nutrients and water into the disc. If these structures are injured, it can lead to deterioration of the disc and altered disc function. Not only do the large laterally drilled hole or holes compromise the integrity of the vertebral bodies, but the spinal cord can be injured if they are drilled too posterior.

Alternatively, current devices are sometimes deployed through a surgically created or enlarged hole in the annulus. The annulus fibrosus consists of tough, thick collagen fibers. The collagen fibers which are found in the annulus fibrosus are arranged in concentric, alternating layers. Intra-layer orientation of these fibers is parallel, however, each alternating (i.e., interlayer) layers' collagen fibers are oriented obliquely (~120). This oblique orientation allows the annulus to resist forces in both vertical and horizontal directions. Axial compression of a disc results in increased pressure in the disc space. This pressure is transferred to the annulus in the form of loads (stresses) perpendicular to the wall of the annulus. With applied stress, these fibrous layers are put in tension and the angle from horizontal decreases to better resist the load, i.e., the annulus works to resist these perpendicular stresses by transferring the loads around the circumference of the annulus (Hoop Stress). Vertical tension resists bending and distraction (flexion and extension). Horizontal tension resists rotation and sliding (i.e., twisting). While the vertical components of the annulus' layers enable the disc to withstand forward and backward bending well, only half of the horizontal fibers of the annulus are engaged during a rotational movement. In general, the disc is more susceptible to injury during a twisting motion, deriving its primary protection during rotation from the posterior facet joints; however, this risk is even greater if and when the annulus is compromised.

Moreover, annulus disruption will remain post-operatively, and present a pathway for device extrusion and migration in addition to compromising the physiological biomechanics of the disc structure. Other devices, in an attempt to provide sufficient mechanical integrity to withstand the stresses to which they will be subjected, are configured to be so firm, stiff, and inflexible that they tend to erode the bone or become imbedded over time in the vertebral bodies, a phenomenon known as "subsidence", sometimes also termed "telescoping". The result of subsidence is that the effective length of the vertebral column is shortened, which can subsequently cause damage to the nerve root and nerves that pass between the two adjacent vertebrae.

SUMMARY OF THE DISCLOSURE

Spinal mobility preservation assemblies are disclosed which are configured to include at least one and often a plurality of pivots or pivot-like components including combinations of components that serve to allow motion in more than one plane, that function in conjunction with one or more elastomeric (e.g., semi-compliant materials capable of elastic deformation) or spring component (including non-helical springs such as the relatively flat Belleville disc), that are particularly effective in preserving motion in any plane relative to the longitudinal axis of the spine.

In the context of the present disclosure, "planes" are defined relative to X,Y,Z orthogonal axes, where Z is the longitudinal axis of the spine. More specifically, rotation about X,Y,Z and motion about X,Y are enabled by use of at least one unconstrained pivot points, and the elastomeric component enables motion in the Z direction and serves to dampen axial compression.

While the term pivot is often used in mechanics in reference to a pointed shaft forming the center and fulcrum on which something turns balances or oscillates, here the term is more like the use of the term in pivot joint (trochoid) in anatomy but is meant to be an even broader concept as unlike classic pivots, many of the pivots of the present disclosure are able to move with respect with a bearing surface to allow a more complex form of motion. Thus the center of rotation is mobile. Additionally, the cup containing the bearing surface may be free to undergo a limited amount of translation relative to the bone anchor associated with that cup. Examples are given with respect to the Z axis but the cup could have a limited ability to move in the X or Y axis. Further, the selective use of a plurality of pivot/bearing surface combinations associated with a single bone anchor allow for more complex pivot motions. The use of asymmetric components to allow more translation or rotation in some directions than other directions adds to the ability to support complex pivot movement. The term pivot is also meant to include more complicated combinations of components that provide an emulation of the same functionality as the pivots disclosed here.

While the range of motion permitted by a healthy spinal motion segment varies from individual to individual, there are typical expected minimum ranges of motion for each type of motion for each for each spinal motion segment. The range of motion for each spinal motion segment is limited not just by the disc but also by the actions of other protrusions of bone on the vertebrae and other biological structures. There is no real advantage to providing a spinal motion preservation assembly that provides a range of motion that far exceeds other biological limits on the ability of the spinal motion segment to move. However, it is desirable to minimize or eliminate limitations on the motion of a spinal motion segment attributable to the implanted spinal motion preservation assembly.

As used herein, the term "unconstrained" refers to the fact that pivots are not fixed, and refers to motion that meets or exceeds the normal range of motion in all six degrees of freedom. Thus, with respect to the lumbar spine, whereas the normal full range of motion typically allows for about 12 degrees of flexion, about 8 degrees of extension, about 9 degrees of left or right lateral bend, and about 2 degrees of clockwise or counterclockwise motion, the mobility preservation assemblies in accordance with a preferred aspect of the present disclosure (e.g., with unconstrained dual-pivots in conjunction with an elastomeric or a spring component) which have been configured for the lumbar spine generally will permit at least about 4 degrees, often at least about 8 degrees and preferably no more than about 20 degrees of flexion (bending forwards). For an axis-symmetric device, the device would be capable of the same degree of movement in flexion, extension (bending backwards), lateral motion to either side, or motion that is a combination of lateral and extension or lateral and flexion. Rotation is completely unconstrained, with no limitation.

With respect to the spine generally, a motion preservation assembly in accordance with the present disclosure generally will often provide at least substantially the normal full range of motion for any particular motion segment being treated and may provide more than 100% of the normal full range of motion. A motion preservation assembly created without an elastically compressible component may provide substantially the normal range of motion with the exception of the limited amount of compression available in the cephalad/caudal axis.

While it is known in the art to implant certain other human joints (e.g., fingers and knees) with devices meant to preserve translation, the spine is the only articulating human joint with six degrees of freedom with respect to motion, as described above. The spinal implant assemblies of the present disclosure are able to preserve motion (including translation) in all six degrees of freedom. The six degrees of freedom when applied to a motion segment can be thought of as the ability of one vertebral body to move relative to the other vertebral body in that motion segment. The spinal implant assemblies of the present disclosure are able to preserve motion in all six degrees of freedom because these assemblies are configured with at least one pivot points preferably in conjunction with an elastomeric or otherwise elastically deformable component (such as some form of spring), so as not to impede the motion (translation), in any plane, of natural structures which bear physiologic loads, and their deployment in an orientation in approximately the line of principal compressive stress, i.e., placement at approximately the center of rotation vis à vis a human vertebral motion segment which includes two adjacent vertebral bodies and the intervening intervertebral disc.

The assemblies may be inserted axially within the spine, following either partial or complete nucleectomy and through a cannula that is docked against the sacrum, into a surgically de-nucleated disc space, from said access point across a treatment zone. In one aspect of the disclosure, prosthetic or augmentation materials are introduced, through at least one vertebral body or into at least one disc space. The introduction of the spinal motion preservation assembly of the present disclosure is accomplished without the need to surgically create or deleteriously enlarge an existing hole in the annulus fibrosus of the disc, and their deployment therapeutically preserves the physiological function of natural disc structures.

In one aspect of the disclosure, risks associated with implant expulsion, migration, or subsidence (that are inherently less for the spinal motion preservation assembly of the present disclosure) may be even further mitigated by retention means, e.g., by external, self-tapping threads configured to distribute stress evenly over a large surface area, that engage the vertebral body and secure (i.e., anchor) the implant assemblies therein.

The screw threads are typical of "cancellous" type bone threads known in the art. The threads are typically cut with generally flat faces on the flights of the thread with the most flat of the faces oriented in the direction of the applied load. In one embodiment, the thread profile generally consists of deep flights with an asymmetric thread form, which provides the advantage of improved weight bearing and load distribution. Threads are formed on root portions and extend as continuous threads from the trailing end to the leading end of the respective threaded sections. The screw threads include multiple revolutions that are spaced apart along the roots by inter-thread spacings. Installation is simplified by delivery of the two bone anchors via timed delivery of threaded components as described in more detail below and thus typically, the proximal component and distal component threads are like-handed (i.e. the threads turn in the same direction) so that both screw threads are right-handed or so that both are left-handed.

In the context of the present disclosure, "dynamic" refers to non-static devices with an inherent ability to allow mobility by enabling or facilitating force or load bearing that assist or substitute for physiological structures that are otherwise compromised, weakened or absent. The spinal motion preservation assemblies (MPA) of the present disclosure provide dynamic stabilization (DS) across a progression-of-treatment interventions for treating symptomatic discogenic pain, ranging from treatment in patients where little degeneration or collapse is evident radio-graphically, to those for whom prosthetic nucleus devices or total disc replacements are indicated. For example, a prosthetic nucleus (PN) would be indicated in patients with a greater degree of degeneration and loss of disc height but not to the stage where advanced annular break-down is present. A prosthetic nucleus would go beyond dynamic stabilization by including an aggressive nucleectomy and subsequent filling of the de-nucleated space with an appropriate material. Here, the goal is to restore disc height and motion. Total disc replacement (TDR) is generally indicated with more advanced disease than with a prosthetic nucleus but where some annular function remains. Many of the motion preservation assemblies of the present disclosure serve as prosthetic disc replacements (PDR) that are much less invasive (in terms of deployment by trans-sacral access) than traditional total disc replacements, and are configured so as to augment, preserve, restore, and/or manage the physiological function according to the intervention indicated. In general, the axial motion preservation assemblies of the present disclosure disclosed herein are preferably configured as devices with an aspect ratio of greater than one, i.e., the device dimension in the axial vertebral direction is greater than the device dimension in any orthogonal direction to that axial direction in close proximity to the physiological instantaneous center of axial rotation, and are deployed in an orientation in approximately the line of principal compressive stress, and placed at approximately the center of rotation vis à vis a human disc motion segment.

BRIEF DESCRIPTION OF THE FIGURES

FIG. 3 illustrates an implanted motion preservation assembly 300 in a spinal motion segment.

FIG. 4 is an exploded diagram that provides an enlarged view of the components described in FIG. 3.

FIG. 6 is a view with a partial quarter round section removed from the distal bone anchor 340 and the proximal bone anchor 344 to reveal the components within an assembled set of components.

FIG. 7 is a view of the same motion preservation assembly 300 but with a quarter round of the entire assembly removed.

FIG. 8A illustrates the effect of using two different pivot body widths.

FIG. 8B illustrates the effect of changing the depth of the pivot end cup.

FIG. 8C illustrates the use of a cavity bevel 636.

FIG. 16 is a perspective view of the dual anchor driver 2000 with a quarter round removed to better show the components.

FIG. 17 is a perspective view of retention rod 2004 and shows the retention rod knob 2032 and the threaded distal tip 2036.

FIG. 18 is a perspective view of an insertion tip 2008 with a quarter round removed.

FIG. 19 is a cross section of the insertion tip 2008 shown in FIG. 18.

FIG. 20 is a cross section of a driver shaft 2012 and a female hexagonal distal end 2052.

FIG. 21 is a cross section view of retainer lock 2020.

FIG. 22 is a cross section of lock stop 2024.

FIG. 31 is a perspective view with quarter round removed of a distal cup driver 2200.

FIG. 32 is a perspective view of a mandrel shaft 2224 component of a distal cup driver 2200.

FIG. 33 is an enlarged perspective view of the expanding mandrel 2204 component of a distal cup driver 2200.

FIG. 34 is a perspective view of a plug shaft 2228 component of a distal cup driver 2200.

FIG. 35 is an enlarged portion of a perspective view of a portion of a plug shaft 2228 component of a distal cup driver 2200.

FIG. 36 is an enlarged portion of a perspective view of the proximal end of a distal cup driver 2200.

FIG. 37 is a perspective view of a support member driver 2260.

FIG. 38 is a cross section of a support member driver 2260.

FIG. 39 is a perspective view with a quarter round removed of a dual use driver 2300.

FIG. 40 is a cross section of the dual use driver 2300.

FIG. 41 shows an enlarged perspective view of insertion tip 2304 with the distal end in the foreground, and also shows one of the two pin engagement holes 2328 used for engagement with a retaining pin 2312.

FIG. 42 shows a perspective view of a retention rod 2316 including a knob 2340 and threaded tip 2344.

FIG. 43 is a perspective view of the proximal anchor stabilizer 2380.

FIG. 44 is a side view of the proximal anchor stabilizer 2380.

FIG. 45 is an enlarged perspective view of a stabilizer tip 2392.

FIG. 53 shows a perspective view with a quarter round removed of a preformed membrane 2450 with a one inch diameter (as measured inside the preformed membrane before adding silicone material).

FIG. 54 shows a cross section of the preformed membrane 2450 of FIG. 53.

FIG. 55 shows a cross section of a ¾ inch preformed membrane 2460 that could be delivered by the same delivery device and membrane tip but may be preferred by a surgeon working with a disc that has a smaller diameter.

FIG. 56 shows a detail applicable to both FIGS. 54 and 55, the membrane channel engagement section 2454 of one side of a membrane.

FIG. 57 is a perspective view of an alternative flat membrane 2470.

FIG. 58 is a cross section of the flat membrane 2470 of FIG. 57.

FIG. 61 is a perspective view of a two level spinal motion preservation assembly 3500 with the membranes hidden to allow a better view of the components.

FIG. 62 is an exploded view of the various components beyond the three bone anchors and two membranes (membranes not shown) that are in the two level spinal motion preservation assembly 3500.

DETAILED DESCRIPTION

Because of the many advantages associated with a minimally invasive, low trauma trans-sacral axial approach, the present disclosure contemplates the use of the trans-sacral axial access to the lumbo-sacral spine. The trans-sacral axial approach (described and disclosed in commonly assigned U.S. Pat. Nos. 6,558,386; 6,558,390; 6,575,979; 6,921,403; 7,014,633, and 7,087,058) has a number of advantages over other routes for delivery of therapeutic devices to motion segments but there are logistical challenges to the delivery and installation of advanced spinal assemblies via an axial access channel. The process of addressing these challenges impacts certain aspects of the implanted device and obviously impacts the design of the insertion tools.

Trans-Sacral Axial Access

The trans-sacral axial access method illustrated in FIG. 2, eliminates the need for muscular dissection and other invasive steps associated with traditional spinal surgery while allowing for the design and deployment of new and improved instruments and therapeutic interventions, including stabilization, motion preservation, and fixation devices/fusion systems across a progression-of-treatment in intervention.

Figure 1:
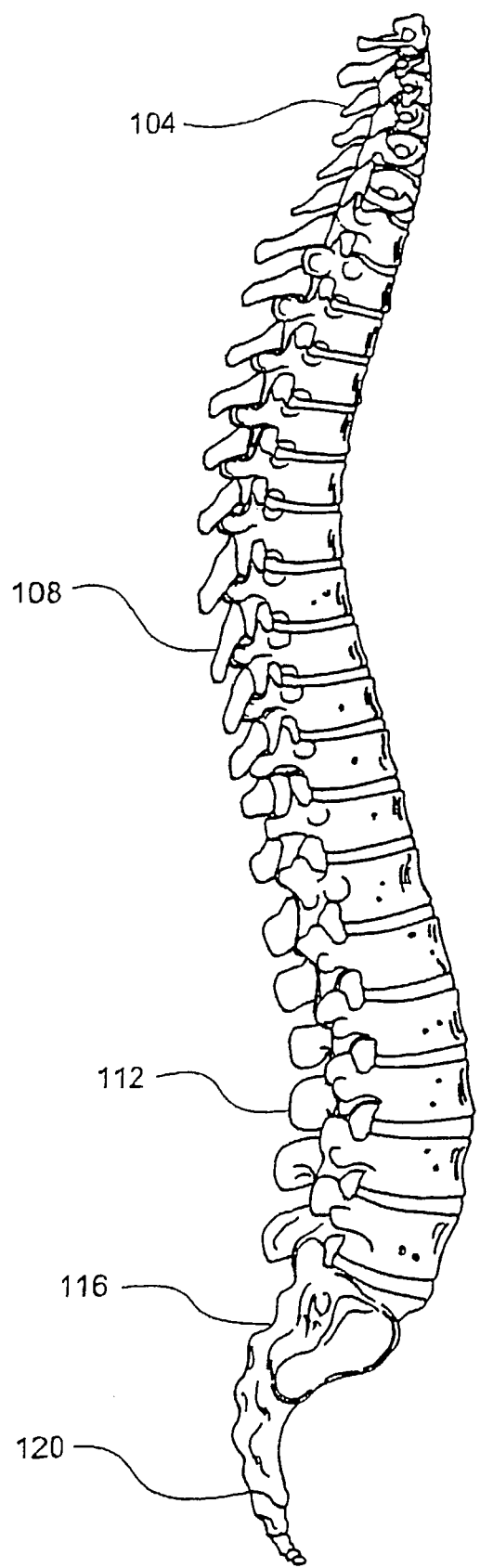
FIG. 1 identifies the sections of a human spine.
Figure 2A:
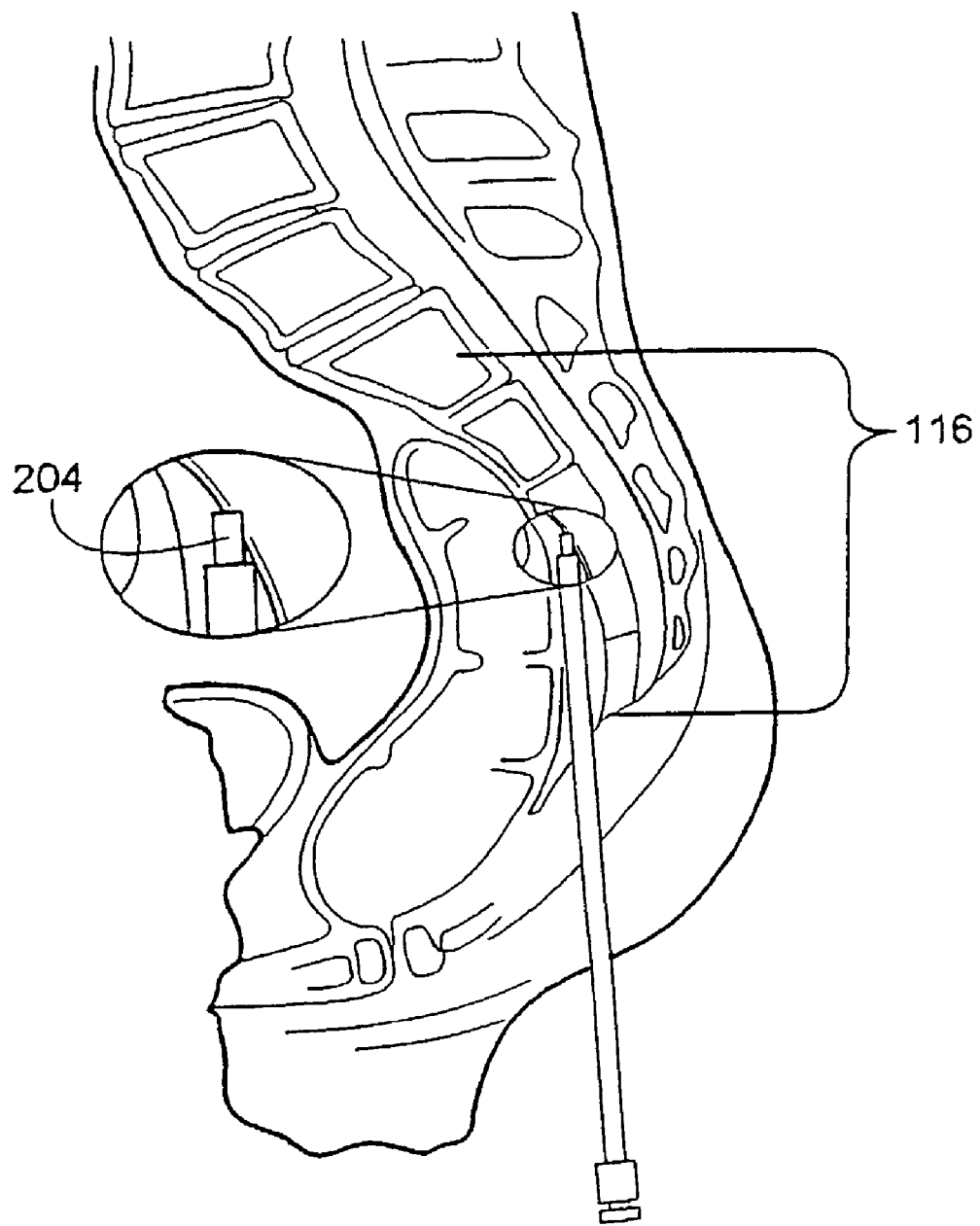
FIGS. 2(*a*)-(*c*) illustrate an anterior trans-sacral axial access method of creating an axial channel in the spine which can be used to prepare an axial channel in the spine for use with the present disclosure
Figure 2B:
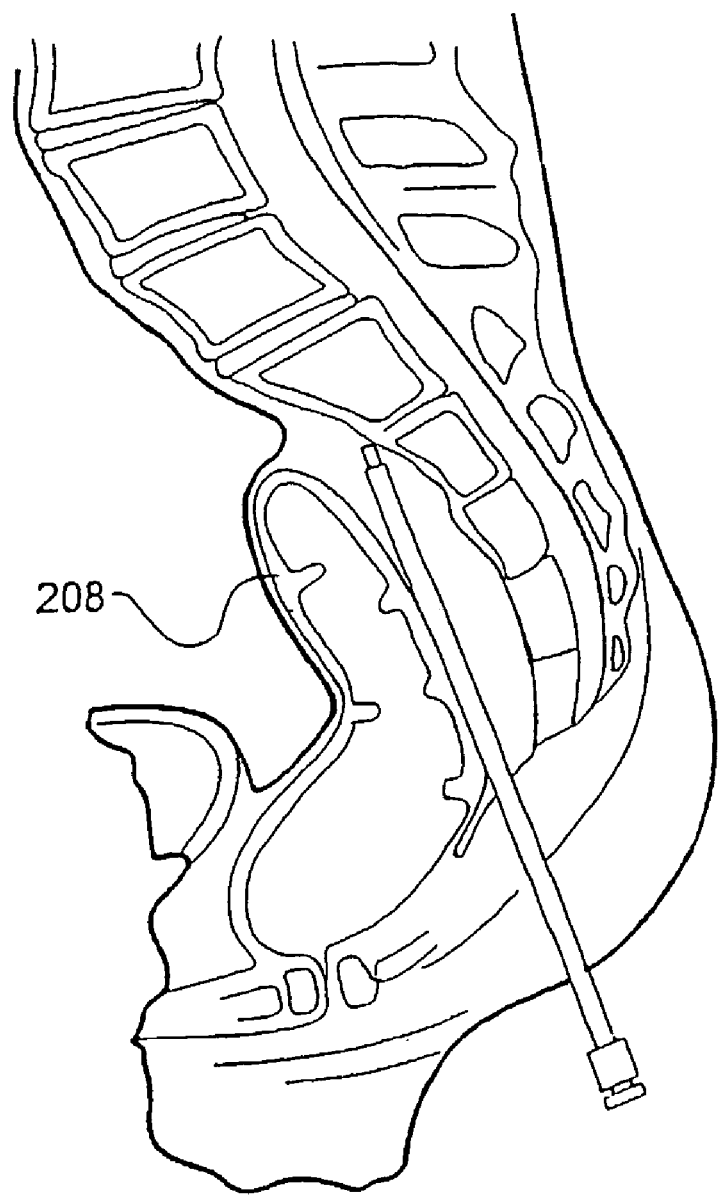
Figure 2C:
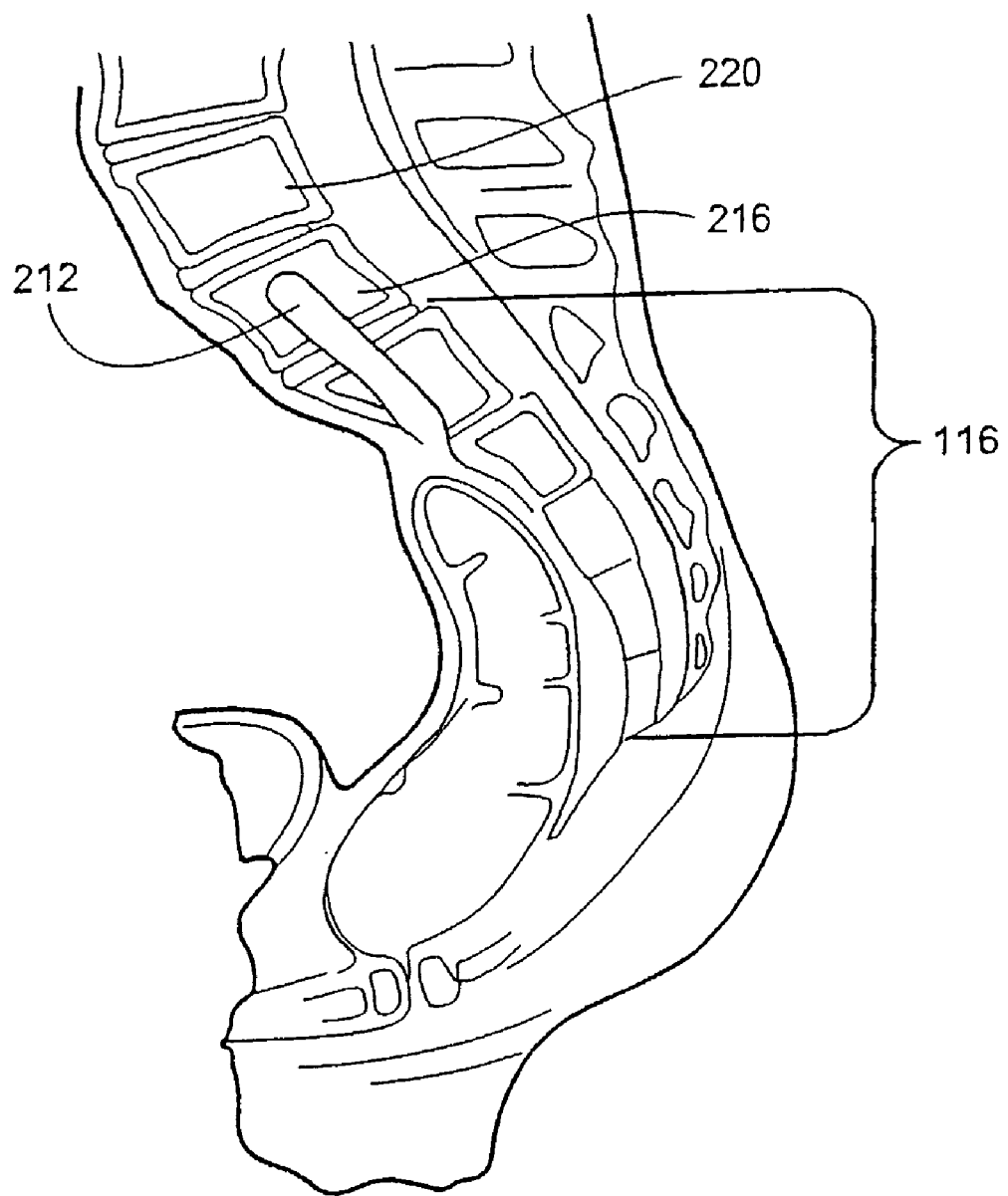

FIG. 2 provides an introductory overview of the process with FIGS. 2(a) and 2(b) showing the process of "walking" a blunt tip stylet 204 up the anterior face of the sacrum 116 to the desired position on the sacrum 116 while monitoring one or more fluoroscopes (not shown). This process moves the rectum 208 out of the way so that a straight path is established for the subsequent steps. FIG. 2(c) illustrates a representative trans-sacral axial channel 212 established through the sacrum 116, the L5/sacrum intervertebral space, and into the L5 vertebra 216. If therapy is being provided to the L4/L5 motion segment then the channel would continue through the L5 vertebra 216 through the L4/L5 intervertebral space, and into the L4 vertebra 220.

The discussion of FIG. 2 provides context for the present disclosure. Previous applications (some now issued as United States patents) assigned to TranS1, Inc. have included a description of an alternative access method that is a posterior trans-sacral axial spinal approach rather than an anterior trans-sacral axial spinal approach. (See e.g. U.S. Pat. No. 6,558,386 for Axial Spinal Implant and Method and Apparatus for Implanting an Axial Spinal Implant Within the Vertebrae of the Spine as this patent describes the anterior trans-sacral axial approach illustrated in FIG. 2 and is incorporated by reference in its entirety.) Many of the teachings of the present disclosure, and in particular devices as shown in FIGS. 3-7, can be utilized with a trans-sacral axial access method.

A brief overview of this method of accessing the spinal region to receive therapy is useful to provide context for the present disclosure. As shown in FIG. 2A, a pre-sacral approach through percutaneous anterior track towards sacral target, through which trans-sacral axial bore will be made and channel extended distally for subsequent advancement of a spinal motion preservation assembly. An anterior, pre-sacral, percutaneous tract extends through the pre-sacral space and ends on the anterior face of the sacrum. The pre-sacral, percutaneous tract is preferably used to introduce instrumentation to access and prepare (e.g., by drilling a bore in the distal/cephalad direction through one or more lumbar vertebral bodies and intervening discs). "Percutaneous" in this context simply means through the skin from a paracoccygeal access point on the patient and to the posterior or anterior target point, as in transcutaneous or transdermal, without implying any particular procedure from other medical arts. However, percutaneous is distinct from a surgical access, and the percutaneous opening in the skin is preferably minimized so that it is less than 4 cm across, preferably less than 2 cm. The percutaneous pathway is generally axially aligned with the bore extending from the respective anterior or posterior target point through at least one sacral vertebral body and one or more lumbar vertebral bodies in the cephalad direction as visualized by radiographic or fluoroscopic equipment. Additional details regarding the process of preparing an axial access channel may be found in co-pending and commonly assigned U.S. Pat. application Ser. Nos. 10/972,065, 10/971,779; 10/971,781; 10/971,731; 10/972,077; 10/971,765; 10/971,775; 10/972,299; and 10/971,780, all of which were filed on Oct. 22, 2004, and commonly assigned U.S. Provisional Patent Application 60/706,704, filed Aug. 9, 2005, and all of which are incorporated by reference herein in their entirety.

First Example

The present disclosure will now be described more fully hereinafter with reference to accompanying drawings in order to disclose selected illustrative implementations of the present disclosure. The teachings of the present disclosure may, however, be embodied in many different forms and should not be construed as limited to the particular implementations set forth herein; rather these implementations are provided so that the disclosure can be thorough and complete, and as part of the effort to convey the scope of the disclosure to those skilled in the art. Like numbers refer to like elements throughout.

In order to avoid the imprecision that can sometimes be introduced into a patent application while discussing many different alternative configurations at once, FIGS. 3-7 start with one very specific embodiment of the present disclosure. In order to provide an overview of the components and their placement with respect to a spinal motion segment, the explanation will start with an overview of an implanted device. Subsequent drawings will provide detail on the delivery and assembly of the device.

Figure 5:
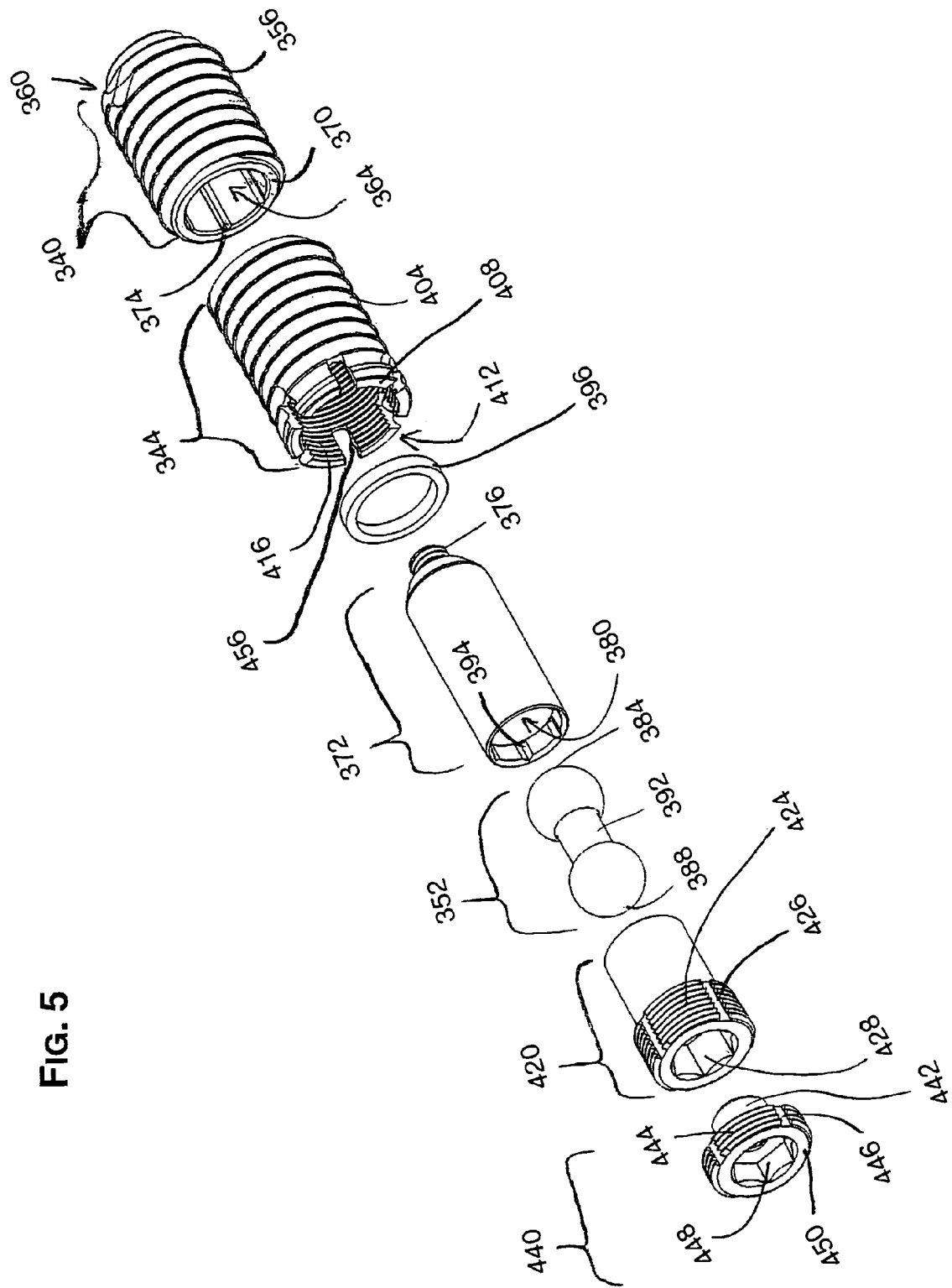
FIG. 5 is an exploded diagram that provides another view of the components described in FIGS. 3 and 4.

FIG. 3 illustrates an implanted motion preservation assembly 300. FIG. 4 provides an enlarged view of the implanted motion preservation assembly 300 in order to allow more room for reference numbers. FIG. 5 provides an exploded diagram that provides another view of the components described in FIGS. 3 and 4. In order to avoid undue clutter from having too many reference numbers and lead lines on a particular drawing, some components will be introduced via one drawing and not explicitly identified in every subsequent drawing that contains that component.

This motion preservation assembly 300 is implanted into a distal vertebral body 304 and a proximal vertebral body 308. As shown in FIG. 3 by way of example, the distal vertebral body is the L5 vertebra 216 and the proximal vertebral body is the sacrum 116. The installed motion preservation assembly 300 extends across an intervertebral disc space 312. The motion preservation assembly 300 would be placed in a previously prepared axial channel 212. The trans-sacral axial approach left intact the axial walls of the annulus fibrosus 254. Collectively, the distal vertebral body 304, the proximal vertebral body 308, and the intervertebral disc space 312 form a motion segment 316 (as the proximal body in FIG. 3 is the sacrum, only the upper portion of the sacrum is shown within bracketed area 316). The drawings of the vertebral bodies in this Figure are not intended to convey anatomical details of the spinal components but to illustrate the placement of the assembled motion preservation assembly 300. In a like manner, other Figures in this disclosure are used to disclose specific concepts rather than to convey details of human anatomy. While the example pair of adjacent vertebral bodies used in FIGS. 3 and 4 are L5 and the sacrum (or to be more specific S1), other motion segments can receive a spinal motion preservation assembly using a trans-sacral axial approach. It is believed that the second most common location for installation of a spinal motion preservation assembly via an axial trans-sacral approach will be between the L4 and L5 vertebrae 220 and 216 (See FIG. 2), but other motion segments may benefit from such devices.

The major components of the motion preservation assembly 300 include the distal component 340 (anchored in the superior, or distal vertebral body, herein also sometimes referred to as distal bone anchor), proximal component 344 (anchored in the inferior, or proximal vertebral body, herein also sometimes referred to as proximal bone anchor), prosthetic nucleus 348 (generally including outer membrane 460), and a support member 352. An optional seal ring 396 (shown most clearly in FIG. 5) will be discussed in connection with the assembly of the device.

The distal bone anchor 340 shown in FIG. 4 has a set of external threads 356. Advantageously, the set of external threads 356 can include a chip breaker section 360 (FIG. 5) at the distal end of the distal bone anchor to facilitate the starting of cutting a thread path into the distal vertebral body 304. A chip breaker is a discontinuity in the thread that allows chips to break off as the thread path is cut. The axial channel 212 is created into the distal vertebral body 304, with the diameter of the axial channel 212 at the distal vertebral body 304 approximately equal, or slightly less than, the minor diameter of the set of external threads 356.

The distal bone anchor 340 has a cavity 364 (best seen in FIG. 5) running from the distal face 366 of the distal bone anchor 340 to the proximal face 370 (FIG. 5) of the distal bone anchor 340. In this context, a face is the three dimensional surface of the part as viewed from that side, akin to the six three dimensional faces of die from a pair of dice. The cavity 364 is not of uniform cross section and serves several purposes. The distal end of the cavity 364 extends to the distal face 366 of the distal bone anchor 340 such that the cavity can be used to allow the distal bone anchor 340 to be deployed over a guide wire (not shown). The cavity 364 includes an internal threaded section 368 which can be engaged by a retention rod (See 2004 in FIGS. 16 and 17) as described below. As shown in FIG. 4, the internal threaded section 368 is engaged with external threads 376 on a distal cup 372. The distal bone anchor 340 is adapted to be driven by a polygonal driver received in the proximal end of the cavity 364 in the distal bone anchor 340. In this implementation, the female hex is little more than a set of hex ridges 374.

The cavity 364 in the distal bone anchor 340 shown in FIG. 4 is substantially filled with the distal portion of the distal cup 372. The distal cup 372 extends beyond the proximal face 370 of the distal bone anchor 340 into the intervertebral disc space 312. If the proximal face 370 of the distal bone anchor 340 is positioned to be roughly coplanar with the proximal face of the distal vertebral body 304, the distal end of the support member 352 is in that portion of the bore that is in the vicinity of what used to be the endplate for that piece of the distal vertebral body 304. Thus, the spinal motion preservation assembly has a pivot point close to the pivot point of a healthy motion segment.

The distal cup 372 in turn has a cavity 380 (best seen in FIG. 5) which serves as a bearing surface for the distal end 384 of the support member 352.

The support member 352 shown in FIGS. 3-5 has the distal end 384 (referenced above) and a proximal end 388 which in this embodiment are configured as substantially spherical components integral with the body 392. While the distal end 384 in FIG. 5 is interchangeable with the proximal end 388, other implementations may have differences between the two ends.

The proximal bone anchor 344 has a set of external threads 404. The proximal bone anchor 344 has a cavity 412 (best seen in FIG. 5) that runs from the proximal face 408 (best seen in FIG. 5) of the proximal bone anchor 344 to the distal face 414 (best seen in FIG. 4) of the proximal bone anchor 344. The cavity 412 is not uniform in cross section. A portion of the cavity 412 has a set of internal threads 416. The pitch of the set of internal thread 416 will be relatively fine (perhaps 16 threads per inch up to 64 threads per inch). For example a thread pitch of 32 threads per inch may be acceptable for some uses.

In the implementation shown in FIGS. 3-5, the proximal bone anchor cavity 412 contains a proximal cup 420 that has a set of external threads 424 that engage with the set of internal threads 416 to allow torque from a driver imparted to a driver engagement section 428 (best seen in FIG. 5) to rotate the proximal cup 420 relative to the proximal bone anchor 344 to axially advance the proximal cup 420. Axial thread grooves 426 in the external threads 424 make the external threads 424 less susceptible from problems arising from small amounts of prosthetic nucleus material (such as silicone) which may get into the internal threads 416 in the proximal bone anchor 344.

One can appreciate that axially advancing the proximal cup 420 will cause the proximal cup 420 to contact the support member 352 and cause the support member 352 to in turn contact the distal cup 372. After these components are in contact, further axial advancement of the proximal cup 420 will cause the axial movement of the distal bone anchor 340 as it contains distal cup 372 (and the distal vertebral body 304 engaged with the distal bone anchor 340). This axial movement of the distal bone anchor 340 will be relative to the proximal bone anchor 344 (and the proximal vertebral body 308 engaged with the proximal bone anchor 344). This movement of one vertebral body away from another vertebral body results in distraction, that is an increase of the intervertebral disc space between the two vertebral bodies.

Note that the distraction that can be achieved by rotation of the proximal cup 420 is preferably used as an adjustment to alter the distribution of loading between the support member and the prosthetic nucleus component of the spinal motion preservation assembly. The primary means for achieving distraction is by use of the distraction driver 2100 as will be described below.

Returning to FIGS. 3-5, the driver engagement section 428 could be configured among any one of many types of ways to impart torque with a driver. A female hex socket is a suitable choice. The proximal cup 420 includes a threaded cavity 432 (best seen in FIG. 4) which can be engaged with a driver or extraction tool. The proximal cup 420 includes a distal cavity 436 that serves as a bearing surface for the proximal end 388 of the support member 352.

The cavity 412 in the proximal bone anchor 344 may also include a jam nut 440 with a distal end 442 and a proximal end 450. The jam nut 440 has a set of external threads 444 adapted to engage with the set of internal threads 416. As with the external threads 424 on the proximal cup 420, the external threads 444 on the jam nut 440 have a set of axial thread grooves 446 to make the external threads 444 less susceptible to problems from prosthetic nucleus material (such as silicone) that becomes present in the internal threads 416 of proximal bone anchor 344 as the thread grooves 446 allow the jam nut 440 to be axially advanced through the threaded engagement despite the presence of some amount of silicone. The jam nut 440 also has a driver engagement section 448 that is adapted to receive torque imparted by a corresponding driver such as a male hex driver. The torque input can cause the jam nut 440 to axially (distally) advance until it makes contact with the proximal cup 420. The jam nut 440 shown in FIG. 3 also includes a threaded cavity 452 (best seen in FIG. 4) which can be used by a driver or extraction tool.

The proximal bone anchor 344 also includes a set of slots 456 on the proximal end of the proximal bone anchor 344. Note that the external threads 404 continue into the portion of the proximal bone anchor 344 that has the set of slots 456.

(Note the cross section seen in FIGS. 3 and 4 passes through a slot 456 on the right side of the proximal anchor which makes it look like the external threads end prematurely on that side). As described in more detail below, these slots 456 may be engaged by a corresponding set of fingers (See 2384 in FIG. 45) on a tool so that the axial position of the proximal bone anchor may 344 be maintained by preventing rotation of the proximal bone anchor 344 while torque is applied to either the proximal cup 420 or a jam nut 440.

The prosthetic nucleus 348 includes an outer membrane 460 and prosthetic nucleus material 464. In one implementation, as outer membrane 460 is filled with prosthetic nucleus material 464, the outer membrane 460 expands to conformably contact the inferior endplate of the distal vertebral body 304, the superior endplate of the proximal vertebral body 308, and the inner wall of the annulus fibrosus 254 which collectively define the boundaries of an intervertebral disc space.

As FIG. 5 shows the various components before insertion into the body with the exception of the outer membrane 460 which is delivered mounted on a special delivery device described below in connection with comments about the process to delivery the components of the spinal motion preservation assembly.

FIGS. 6 and 7 provide additional views of motion preservation assembly 300 previously discussed in connection with FIGS. 3-5. FIG. 6 provides a view with a partial quarter round section removed from the distal bone anchor 340 and the proximal bone anchor 344 to reveal the components within an assembled set of components. FIG. 7 is a view of the same motion preservation assembly 300 but with a quarter round of the entire assembly removed.

FIG. 6 shows the internal threaded section 368 of the distal bone anchor 340 and the external threads 376 on the distal cup 372. The seal ring 396 is visible at the end of the internal threads 416 of the proximal bone anchor 344. In FIG. 6, unused threads 418 of the set of internal threads 416 are visible as the proximal cup 420 could be axially advanced relative to the proximal bone anchor 344. A cross section of one of the shallow hex ridges 374 is visible in FIG. 6. FIG. 7 shows the upper portion of a jam nut 440 within but not contacting the driver engagement section 428 on the proximal cup 420.

Alignment marks 472 are visible in FIG. 6. The quarter round cross section in FIGS. 6 and 7 and the cross section in FIGS. 3 and 4 are taken through a set of cuts in the outer thread in the distal anchor 340 and proximal bone anchor 344. These alignment marks 472 are one way of marking the anchors so that they can be loaded on a driver for timed delivery.

A timed delivery of the two bone anchors 340 and 344 allows for control over the rotational position of the two sets of threads. The purpose of this controlled delivery is to avoid cross threading. More specifically, when electing to use the same thread pitch for the external threads 356 on the distal bone anchor 340 and on the external threads 404 on the proximal bone anchor 344, the distal bone anchor 340 can be made with as large a cross section (rod diameter) as the proximal bone anchor 344. Having a large cross section is desirable as it makes it easier to design a distal bone anchor with adequate strength and maximum engagement between the threads and the bone of the distal vertebral body 304.

If the minor diameters and the major diameters of the threaded portions of distal bone anchor 340 and the proximal bone anchor 344 are the same, then the bores through the proximal vertebral body 308 and the distal vertebral body 304 created during the process of creating the axial channel 212 could be the same size. As the distal bone anchor 340 is moved towards the bore in the distal vertebral body 304, the distal bone anchor 340 is first axially advanced by rotating it through the bore in the proximal vertebral body 308. As the distal bone anchor 340 is rotatably advanced through the proximal vertebral body 308, the external threads 356 cut a helical thread path into the bone around the bore in the proximal vertebral body 308 as the bore is approximately the size of the minor diameter of the external threads 356 (the bore may be slightly smaller than the minor diameter) and the major diameter of the external threads 356 extends beyond the bore into the bone. Without timing or keyed delivery, the subsequent axial advancement of the proximal bone anchor 344 would tend to cut a new helix into the bone around the bore in the proximal vertebral body 308. This second helix would meet added resistance as the bone has just received a newly cut thread helix, and the strength of the connection between the external threads 404 on the proximal bone anchor 344 is compromised by previously cut and now unused thread path through the bone. In contrast, timed delivery allows the leading edge of the helical thread on the exterior of the proximal bone anchor 344 to enter into the helical thread path left by the external threads 356 on the distal bone anchor 340. An alternative to timed delivery is to size the major diameter of the external threads on the distal bone anchor to be less than the diameter of the bore in the proximal vertebral body and then prepare a bore in the distal vertebral body that is approximately the size of the minor diameter of the external threads on the distal bone anchor. A variation of this alternative is to have the major diameter of the external threads on the distal bone anchor to be just slightly larger than the bore in the proximal vertebral body so that the distal bone anchor may be rotated to axially advance through the proximal vertebral body, but the resulting helical thread path is not very deep and does not prevent the subsequent proximal bone anchor with a larger major diameter from cutting a deeper helical thread path to firmly anchor the proximal anchor. The minor diameter of the proximal bone anchor may slightly exceed the bore in the proximal vertebral body.

Returning now to FIG. 4, it is preferred that the bulk prosthetic nucleus materials (PNM) (element 464 in FIG. 4) include elastomeric solids and/or viscoelastic gels, i.e., materials whose viscoelastic properties (e.g., rheology) alone or in conjunction with the biomechanical properties of outer expandable membrane 460, enable them to perform in a functional manner which is substantially equivalent to the physiologic disc nucleus. Preferred prosthetic nucleus materials and systems may use biomedical grade silicone elastomer e.g., silicone rubber, such as that obtained from Nusil Silicone Technology located in Carpeneria, California or hydrogels or blends thereof (e.g., hydrogel/hydrogel, or hydrogel/elastomer). Cross-linked hyaluronic acid, such as is available from Fidia Corporation in Italy, is an example of a suitable material, however, many natural and man-made hydrogels or blends thereof may be configured to achieve similar properties without inflammatory response, such as those disclosed and described in co-pending and commonly assigned United States Patent Applications referenced above, and in detail in particular in U.S. Provisional Patent Applications 60/599,989 filed Aug. 9, 2004, and 60/558,069 filed Mar. 31, 2004, each of which are incorporated in their entirety into this disclosure by reference. Priority is also claimed to co-pending and commonly assigned U.S. Patent Application 11/199,541 filed Aug. 8, 2005 for "Prosthetic Nucleus Apparatus and Methods" and the provisional 60/599,989 filed Aug. 9, 2004 claimed as a priority document in the '541 application. Both of these applications are incorporated in their entirety into this disclosure by reference.

While other prosthetic nucleus membranes will be described as alternatives in a subsequent portion of this document, one combination that is of interest is a silicon membrane filled with silicon as the silicon used to fill the membrane effectively becomes functionally indistinguishable post cure with the silicone membrane.

Degrees of Freedom and Limitations

As FIGS. 3 through 7 are static and the desired attributes of a motion preservation assembly are dynamic stabilization, it is appropriate to dwell on how the motion segment can move with an implanted spinal motion preservation assembly.

Looking at FIG. 4, if one looks at pivot point 480 located just above the threaded cavity 432 in the proximal cup, one can start to count the ways that the distal bone anchor 340 and corresponding distal vertebral body 304 can move relative to the pivot point 480. The first type of movement is axial rotation (clockwise or counterclockwise) around the Z axis. Nothing in this particular spinal motion preservation assembly places a limit on the amount of clockwise or counterclockwise motions. As discussed above, a system that allows about two degrees of rotation about this Z axis would support the normal range of motion on this axis.

As the normal full range of motion typically allows for about 12 degrees of flexion, about 8 degrees of extension, about 9 degrees of left or right lateral bend, in order to avoid constraining the normal range of motion, an installed spinal motion preservation assembly would need to allow at least these amounts of rotation in the relevant planes. The precise range and degree of motion for a motion segment varies along the motion segments of the spine. For example the range and degree of motion in the L4-L5 motion segment will not be exactly the same as for the L5-S1 motion segment.

The device shown in FIG. 4 is radially symmetric around the Z axis so it does not need to be positioned in a particular orientation in order to provide the maximum capacity for rotation in a particular direction (for example flexion versus extension or lateral bending). The rotation of the implanted distal bone anchor with respect to the proximal bone anchor can be achieved through a combination of the action of the proximal end 388 of support member 352 moving with respect to the proximal cup 420 and the action of the distal end 384 of support member 352 moving with respect to the distal cup 372.

Support member 352 discussed above, has a pair of pivots. One can change the maximum pivot angle of a pivot with respect to the corresponding cup by varying two parameters, the depth of the cavity in the cup and the width of the pivot body (compare with support member body 392 in FIG. 5) with respect to the pivot cavity. FIG. 8A and FIG. 8B illustrate these concepts. FIG. 8A illustrates two different pivot body widths. If a pivot body was changed from width 608 to width 612, then the wider pivot body 612 would hit the pivot end cup 604 after a smaller amount of rotation than if the pivot body remained with width 608.

FIG. 8B uses the pivot body of FIG. 8A but places it in a pivot end cup 616 that is not as deep so that the pivot can rotate with respect to the pivot end cup more in FIG. 8B than in FIG. 8A. Comparing FIG. 8C to FIG. 8B shows another way to increase the range of motion for a pivot. Pivot end cup 632 is much like pivot end cup 616, except that pivot end cup 632 has a cavity bevel 636. In some cases the use of a cavity bevel will allow a pivot the ability to move further before coming in contact with the pivot end cup. The spinal motion preservation assembly shown in FIGS. 3-7 includes a cavity bevel 410 in the proximal bone anchor 344 (as best seen in FIGS. 4 and 6). As the proximal cup 420 is recessed relative to the distal face of the proximal bone anchor 344, it is appropriate to place the bevel on the anchor rather than the cup. The particular distal pivot cup shown in FIG. 5 has about a 45 degree bevel 406.

The use of two pivots allows for translation of one implanted bone anchor relative to the other in the X axis (anterior/posterior), Y axis (lateral) or a combination of the two. In order to appreciate the advantage of using two pivots, it is useful to look at the movement when there is one pivot. In FIG. 9(a), a single pivot 650 is engaged with a bearing surface in proximal bone anchor 654 and fixed to distal bone anchor 658. When the pivot 650 rotates in the X-Z plane away from the Z axis as shown in FIG. 9(b), the distal bone anchor 658 moves in rotation with respect to the proximal bone anchor 654 to change the relative orientation of the one bone anchor to the other.

Figure 9:
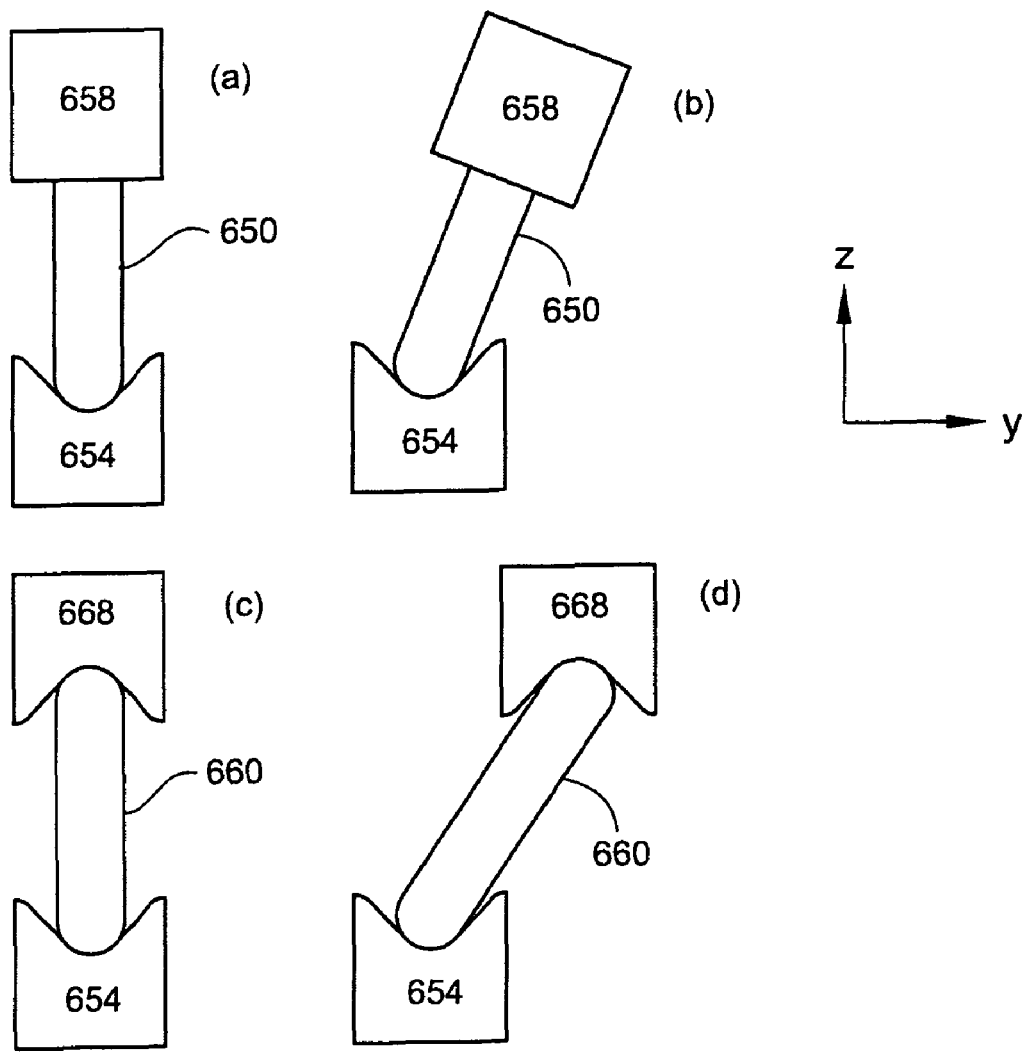
FIG. 9 illustrates the advantage of a dual pivot over a single pivot.

In contrast, in FIG. 9(c), the pivot 660 is a dual pivot and thus can pivot with respect to proximal bone anchor 654 or distal bone anchor 668. Now the distal bone anchor 668 can move in substantially pure translation along the X axis with respect to the proximal bone anchor 654. The relative orientations of the bone anchors are preserved as the movement did not impose a rotation on the distal bone anchor 668. The term substantially pure translation was used as the elevation of the distal bone anchor 668 changed slightly during the movement from the state shown in FIG. 9(c) to the state shown in FIG. 9(d) which would not happen in pure X axis translation. While this example showed translation in the X axis, the same type of movement as shown in FIG. 9 would happen in the Y axis or in a mix of X and Y components unless the pivots were restrained in some way.

While the example of the spinal motion preservation assembly shown in FIGS. 3-7, provides significant capacity for X or Y translation, additional translation could be allowed by expanding the cavities in the cups to exceed the maximum diameter of the pivot end sphere by 5 millimeters. This added cavity size will provide some additional capacity for translation.

Figure 10:
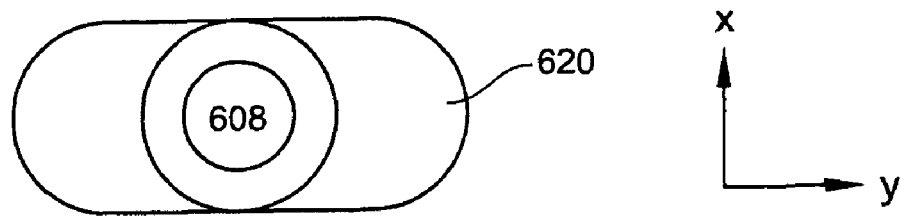
FIG. 10 illustrates a non-symmetric cavity (raceway 620) which serves as the constrained area for the pivot 608 to move within to allow for a greater amount of additional allowed translation in one direction as compared with another direction.

The example shown in FIGS. 3-7 uses radially symmetric pivot ends and cup cavities. Using a non-symmetric cavity in the cup could allow for a greater amount of additional allowed translation in one direction as compared with another direction. FIG. 10 shows an example of this concept. Looking down on a pivot 608, the wall of the pivot body and the maximum dimension of the spherical head of the pivot are both shown. Also shown is raceway 620 which serves as the constrained area for the pivot 608 to move within. Note that additional translation in the X direction is extremely limited but a much greater amount of additional translation is possible in the Y (lateral) direction. When using such an asymmetric raceway, the insertion technique would need to control the orientation of the bone anchor so that the elongated direction of the raceway was aligned in the proper direction. One method is to insert the components in a particular orientation with respect to the driver. The driver would have a marker on it so that the driver marker could be monitored to ensure placement of the components in proper orientation with the anterior/posterior and lateral axes. Orientation of cups within inserted bone anchors could be controlled by having a key and slot engagement between the cup and bore within the anchor.

Figure 11:
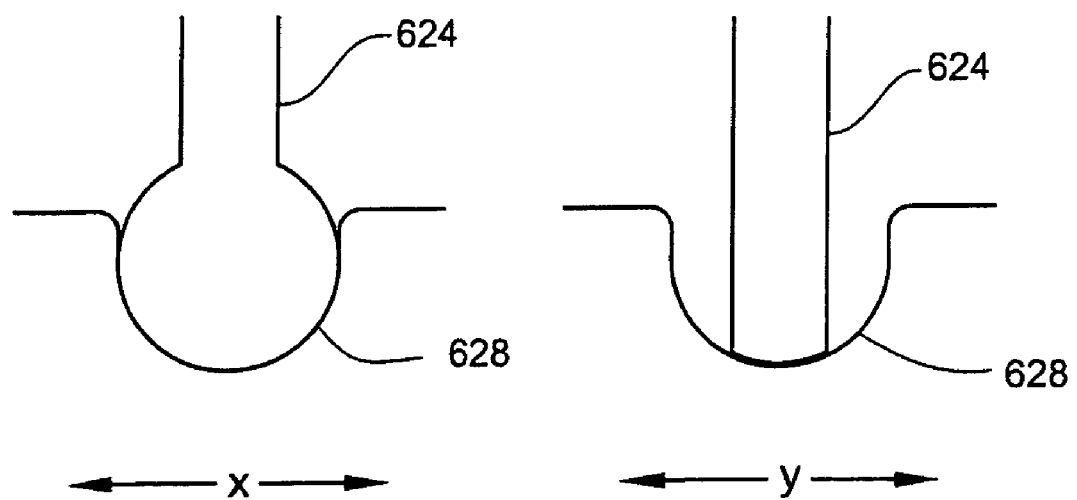
FIG. 11 illustrates an asymmetric pivot.

Another way to allow more bending in one direction than in the other is to have an asymmetric pivot. FIG. 11 illustrates an asymmetric pivot 624 (only one end of the pivot is shown) in a cup 628. This asymmetric pivot provides more limitation on the movement in the X direction (anterior/posterior) than in the Y direction (lateral left/lateral right). When using an asymmetric component, it is important that the installation procedure place the asymmetric component in the proper starting position. Note, that although the device supports unlimited rotation along the Z axis, the positioning of the asymmetric pivot will remain relatively constant as the range of axial rotation for an individual motion segment is only approximately two degrees clockwise and approximately two degrees counterclockwise.

In order to provide the $6^{th}$ degree of freedom, translation in the Z axis, the motion preservation assembly would need to allow the distal bone anchor to move in the Z axis relative to the proximal bone anchor. (A careful observer will note that the translation in the X or Y axis achieved through the use of dual pivot points will incidentally provide for a change in the Z axis but a force purely along the Z axis would not cause this sort of translation.) Adding a degree of freedom for Z translation can be achieved in theory by a device that elongates in tension. However, tensile loads that impart a distraction on a motion segment are rare. The most common being the therapeutic application of traction to extend the spine.

Thus, the more useful capacity for translation in the z-axis is the ability of the spinal motion preservation assembly to compress. There are many motion segments in a spine so it is not surprising that the amount of compression for an individual motion segment is not a large distance. A healthy motion segment in a spine may be capable of about 0.9 millimeters of compression with approximately 0.5 millimeters of compression attributed to the nucleus and approximately 0.2 millimeters of compression attributed to each vertebral body as the endplates on either side of the nucleus move relative to their respective vertebral bodies. Thus, under an appropriate compressive load, the distance from a midpoint in one vertebral body to the midpoint of an adjacent vertebral body can be reduced by about 0.9 millimeters. As with most statements about motion segments, one caveat is that there is variation in expectations for motion segments in different parts of the spinal column and as with many things anatomical, there can be substantial variation between people especially when the very young and the very old are considered.

It may be advantageous to add to a spinal mobility preservation assembly the ability to compress along the Z axis. Ideally, the compression would be reversible and repeatable so that the assembly could undergo many cycles of compression and recovery. Thus, the deformation from the compression would need to be elastic. Elasticity is the property whereby a solid material changes its shape and size under force but recovers its original configuration when the forces are removed. For many people, elastic deformation brings to mind a rubber ball that can be deformed and then resumes its original shape. Bladders can undergo elastic deformation (examples include pneumatic tires and the bladders in soccer balls). Elastic deformation can be achieved through use of springs including disc springs of various types such as a Belleville disc spring or comparable spring.

Addition of an elastically deformable component in the motion preservation assembly would allow this motion segment to contribute to the spinal column's ability to compress under a heavy compressive force such as landing on feet after jumping or falling onto the buttocks. As the set of motion segments are in a stack, the lack of ability of one motion segment to elastically compress may be tolerable as it is tolerated for the people who have a fused motion segment. Having some ability to elastically compress in the Z direction is thought to be desirable especially for spinal motion preservation assemblies with prosthetic nuclei as these ideally mimic the behavior of a natural motion segment.

Elastic deformation of the spinal motion preservation assembly to allow the endplates of the distal vertebral body and the proximal vertebral body to move closer together would apply a compressive force on the prosthetic nucleus that assumed a conforming fit shape that contacts the endplates of these vertebral bodies. For at least some choices for prosthetic nucleus, compression of the prosthetic nucleus in the Z direction causes it to expand radially outward to maintain the overall volume of the prosthetic nucleus as the material in the prosthetic nucleus may be for all practical purposes incompressible (unless there was a substantial amount of gas in the prosthetic nucleus, the amount of compression may be so small as to negligible). As the prosthetic nucleus expands radially outward, it transfers forces to the various layers of the annulus fibrosus, thus mimicking the natural transfer and dissipation of physiologic loads.

Having a spinal motion preservation assembly with the ability to undergo elastic (recoverable) deformation in the Z axis and the ability to promote radial distribution of loads to the annulus fibrosus to mimic normal physiological load sharing is apt to reduce the risk of subsidence or transition syndrome. The discussion of various options for the introduction of elastically deformable components to allow for elastic deformation along the Z axis of the spinal motion preservation assemblies will be discussed in detail below with the discussion of alternative implementations of spinal motion preservation assemblies. The use of one or more elastically deformable components may allow compression of substantially up to the about 0.9 millimeters of compression that is possible in some healthy motion segments.

Process to Deliver a Spinal Motion Preservation Assembly

The process to deliver the spinal motion preservation assembly shown in FIGS. 3-7 will be set forth with some level of detail such that the interaction of the assembly components with the various drivers can be understood sufficiently so that one of ordinary skill in the art will be able to recognize and implement the necessary modifications to the drivers to deliver one of the alternative implementations of the device as discussed below, or certain variations of the illustrative implementations. A co-pending application for Driver Assembly for Simultaneous Deliver of Spinal Implants U.S. patent application Ser. No. 11/259,614 discusses in detail drivers for a different spinal motion preservation assembly. The '614 application has been incorporated by reference and augments the teachings of this application with respect to the use of drivers to deliver spinal motion preservation assemblies.

The process to deliver the spinal motion preservation assembly may be described in the context of flow charts and in an examination of drivers that can be used. With respect to the flow chart, it may be useful to view the process at a summary level in one flow chart and then in a more detailed level in a subsequent flow chart. Even at the more detailed level, the flow chart is conveying process steps to one of ordinary skill in the art and not every movement or sub-step needs to be conveyed.

Figure 12:
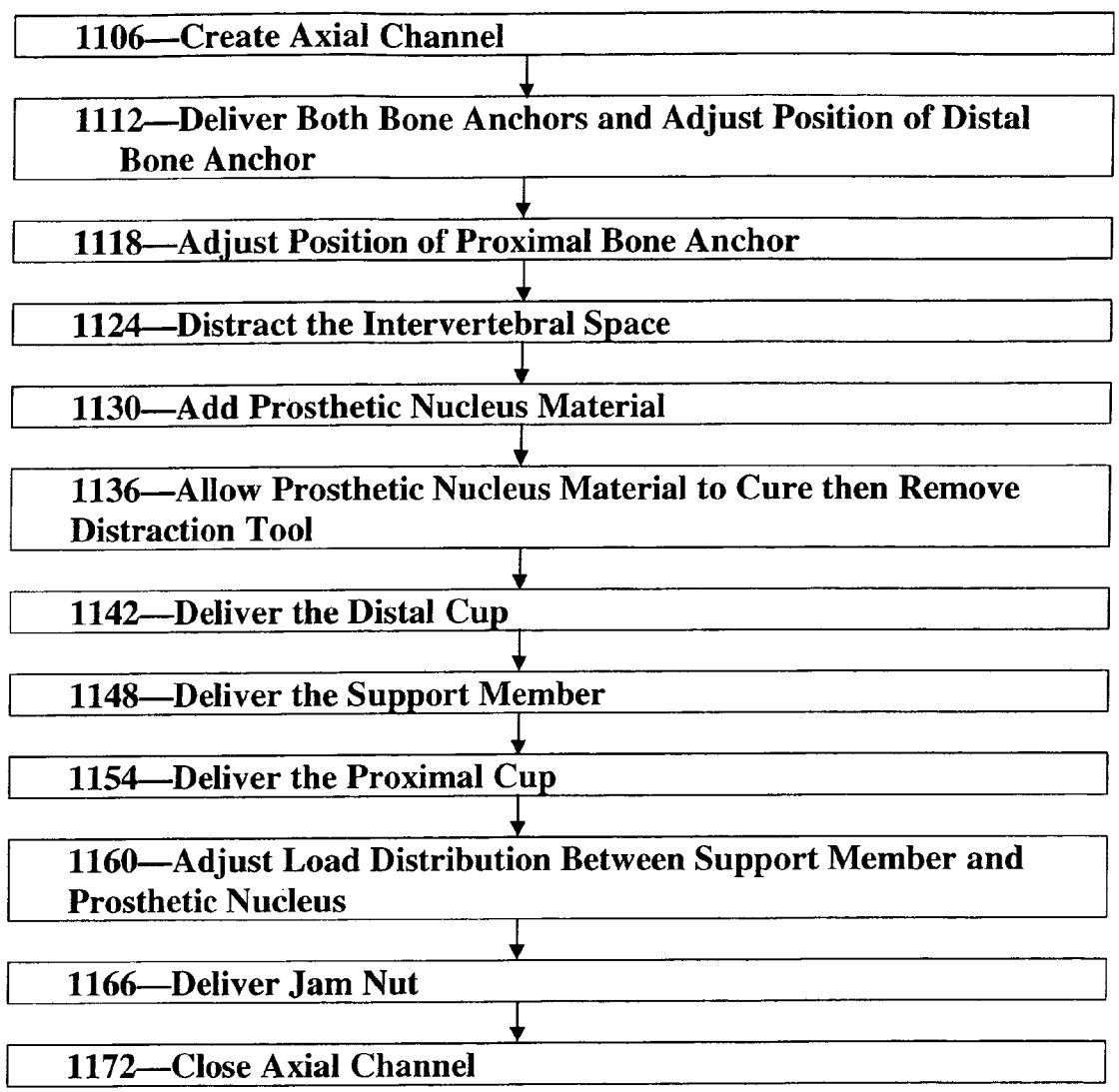
FIG. 12 is high level flow chart that is useful to introduce the overall sequence of events for delivery of a spinal motion preservation assembly of the type illustrated in FIGS. 3-7
Figures 13, 13A:
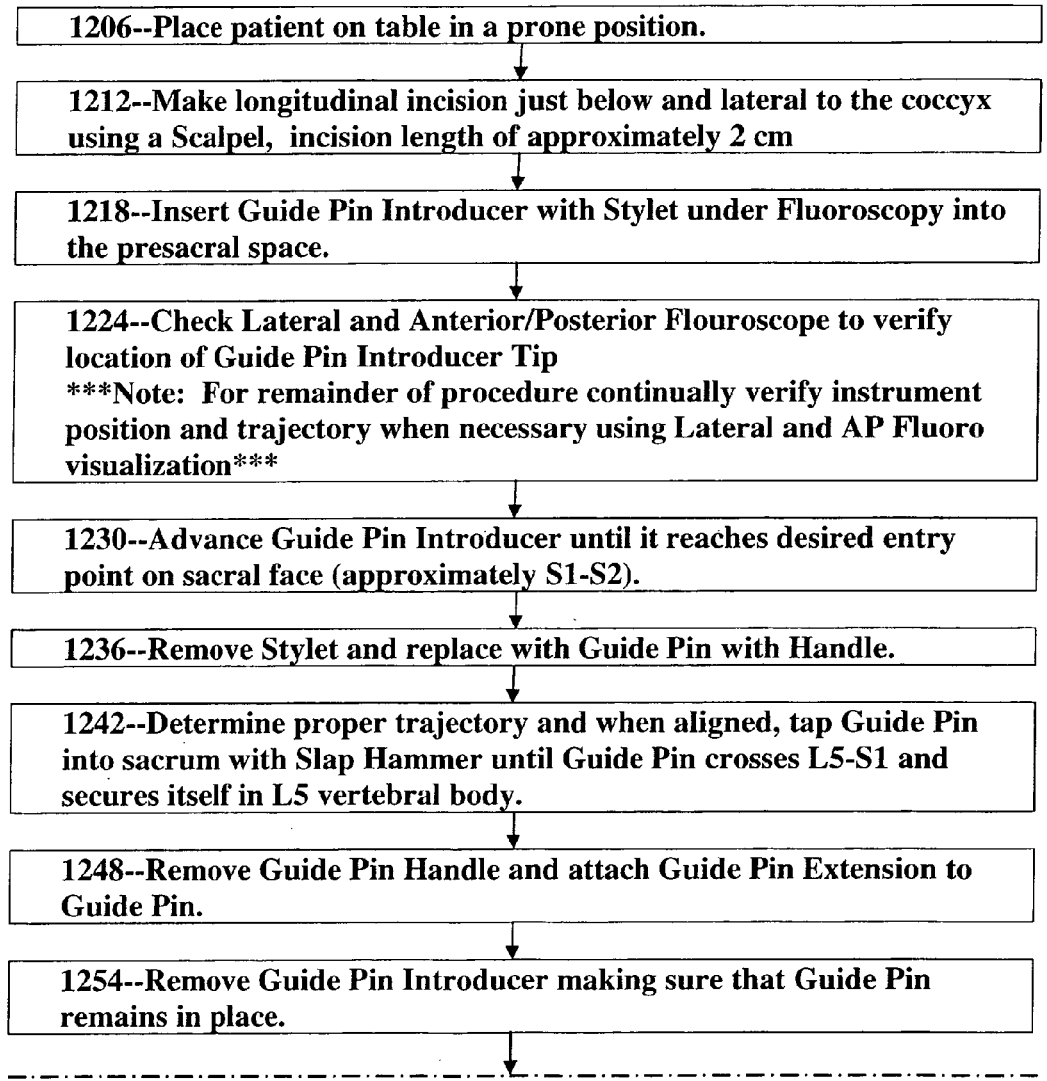
FIG. 13 is a flow chart containing one set of steps that could be used to prepare an axial channel via an anterior trans-sacral axial approach for use with distal and proximal anchors having the same major diameter.
Figure 13B:
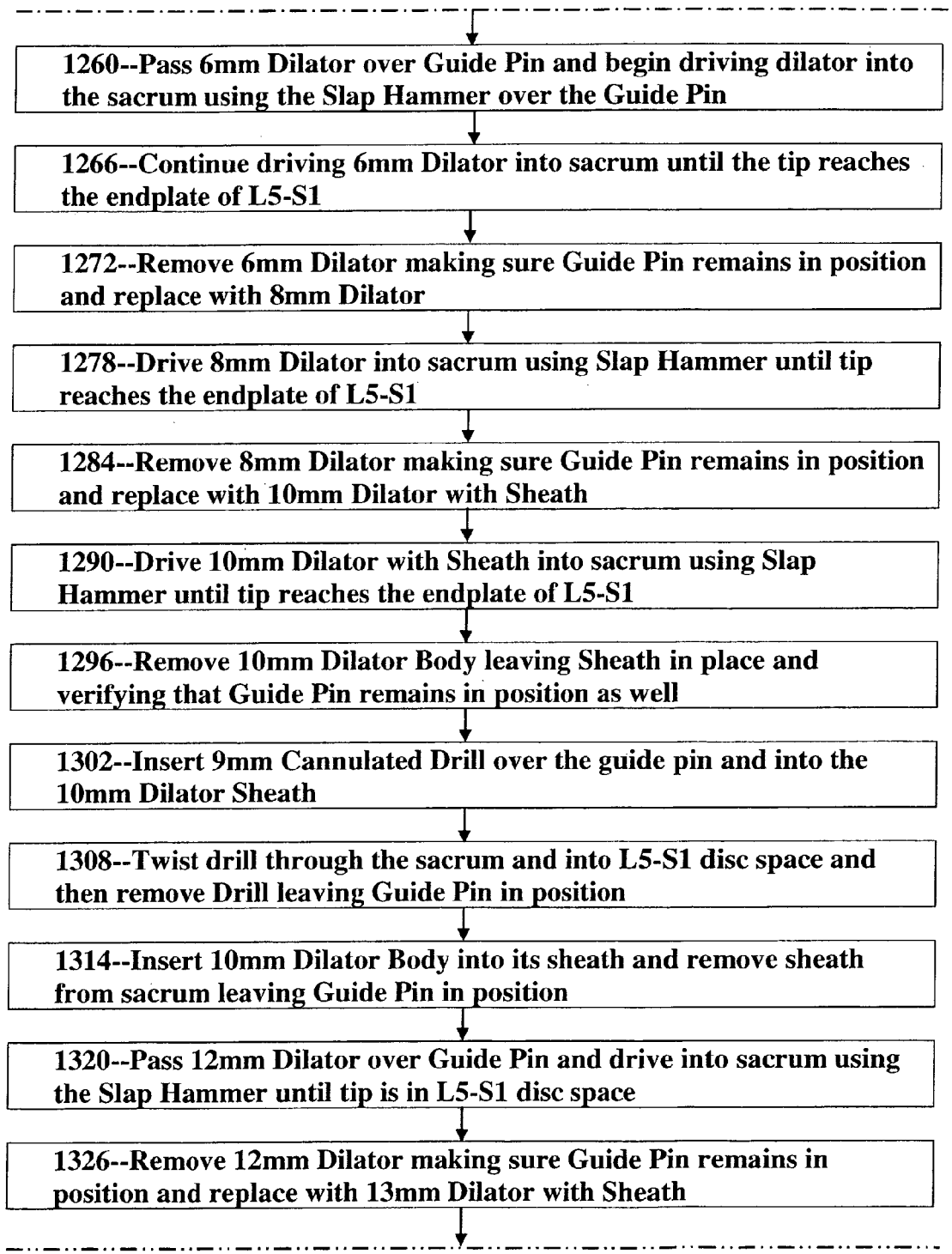
Figure 13C:
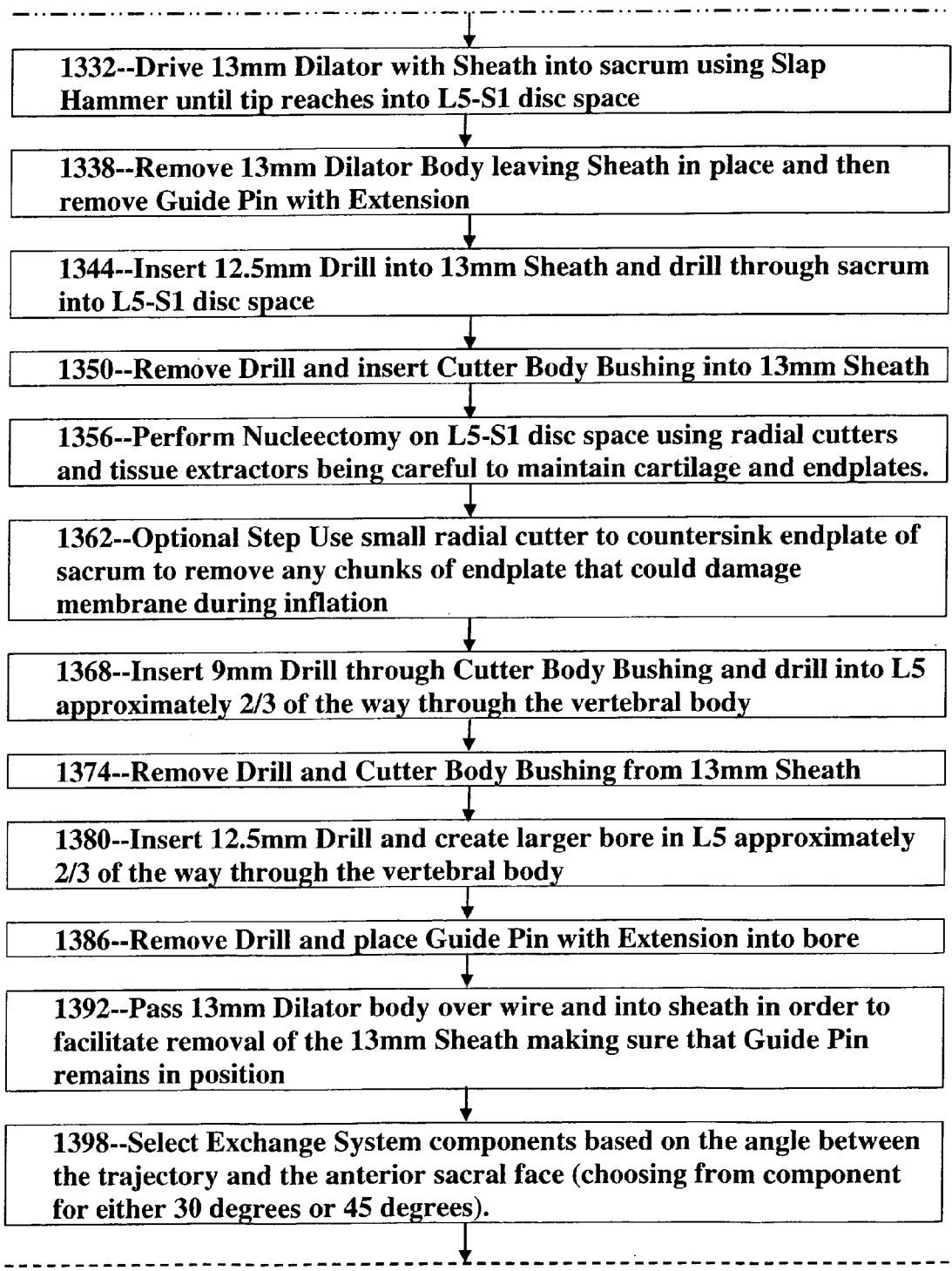
Figure 13D:
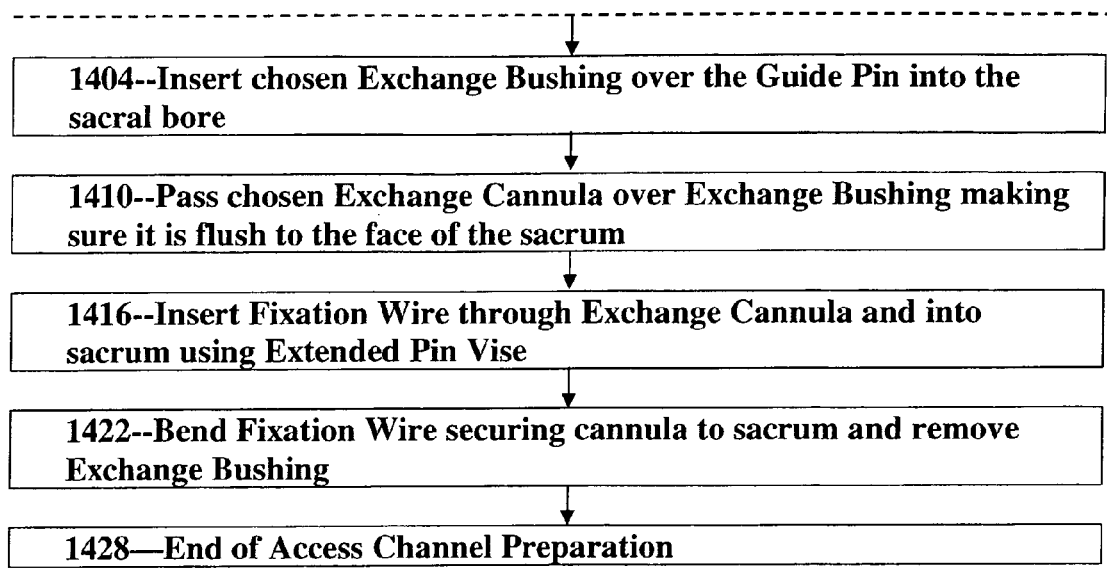
Figure 14C:
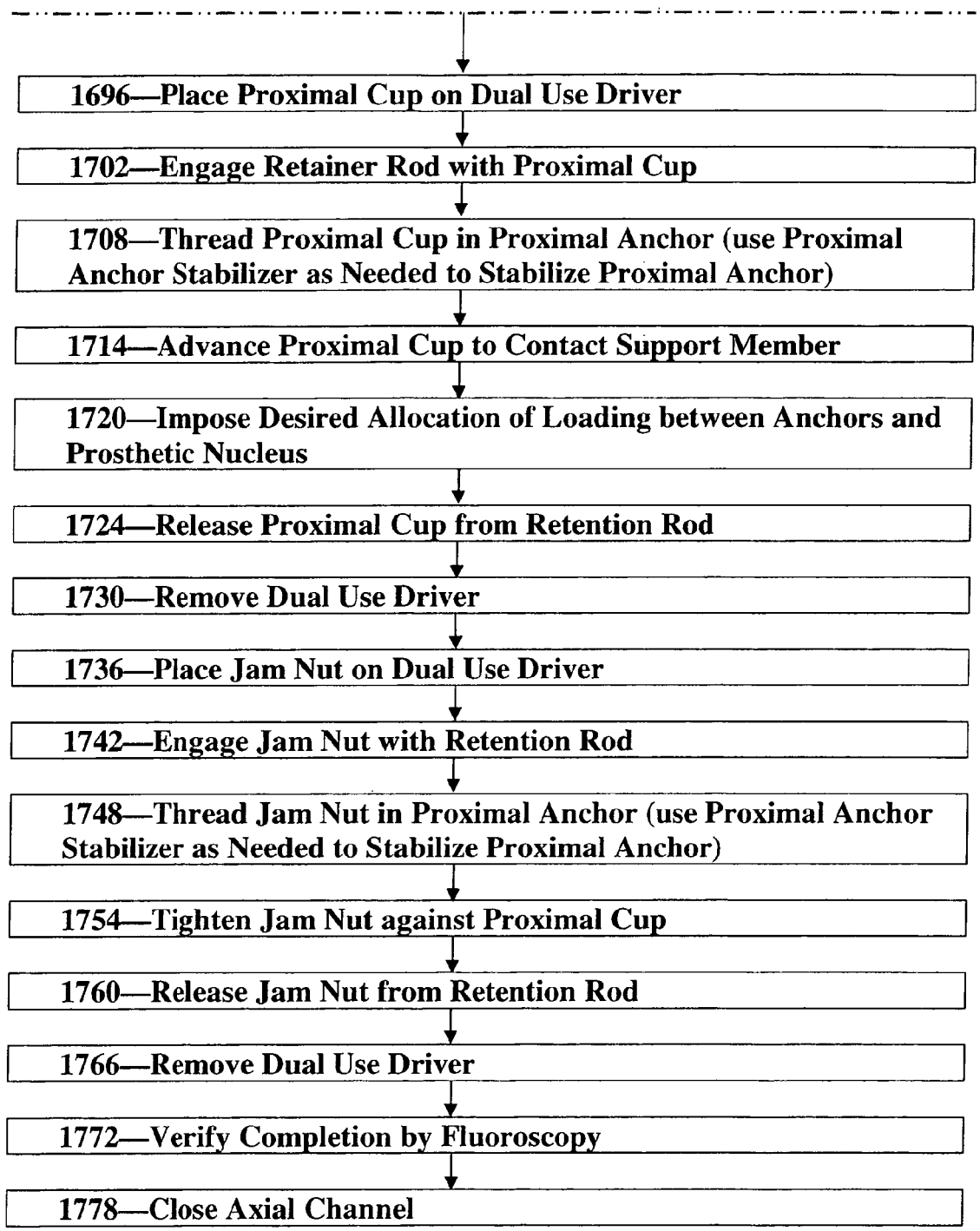
FIG. 14 is a flow chart with one set of steps to deliver a spinal motion preservation assembly of the type illustrated in FIGS. 3-7.

FIG. 12 is a high level flow chart that is useful to introduce the overall sequence of events for delivery of a spinal motion preservation assembly of the type illustrated in FIGS. 3-7. This flow chart and the more detailed flow charts contained in FIGS. 13-14 provide details that are specific to delivery of a specific implementation of the teachings of this disclosure to a specific motion segment via a specific route. Thus, while there are many possible variations of the ways that spinal motion preservation assemblies may be implemented, when describing a specific delivery process for a specific implementation of a spinal motion preservation assembly, it is appropriate to focus and describe a specific process. This specificity is thought to be useful in illustrating the interaction between specific portions of the spinal motion preservation assembly components and the various drivers used in the delivery process so that one of ordinary skill in the art could modify both the components and the drivers as needed to deliver other spinal motion preservation assemblies incorporating one or more teachings of the present disclosure. With that understanding of the purpose of these flow charts, attention is directed to FIG. 12.

1106—Create axial channel 212. This process will be described in more detail in connection with FIG. 13.

1112—Deliver both bone anchors (340 & 344) to the pair of vertebral bodies and adjust the position of the distal bone anchor 340 relative to the distal vertebral body 304. As described below, in this implementation, the two anchors are delivered by timed delivery on a single dual anchor driver. As the position of the distal bone anchor 340 is adjusted, the dual anchor driver is also engaged with the proximal bone anchor 344.

1118—Adjust the position of just the proximal bone anchor 344 after disengaging the dual anchor driver from the distal bone anchor 340.

1124—Distract the intervertebral space 312 between the distal vertebral body 304 and the proximal vertebral body 308 by forcing an increase in distance between the distal bone anchor 340 and the proximal bone anchor 344.

1130—Add prosthetic nucleus material to fill the void in the intervertebral disc space 312 but not in the portion of the intervertebral disc space between the proximal bone anchor 344 and the distal bone anchor 340 as that space is occupied during filling by a portion of the device used to fill the prosthetic nucleus.

1136—Allow the prosthetic nucleus material to cure so that the prosthetic nucleus can substantially maintain the distraction after the distraction tool is removed and share some of the load applied to the motion segment.

1142—Deliver the distal cup 372 into the distal bone anchor 340.

1148—Deliver the support member 352 to place the distal end 384 of the support member in proximity to the distal cup 372.

1154—Deliver the proximal cup 420 to the proximal bone anchor 344.

1160—Adjust load distribution between that as supported by support member (e.g., distributed to bone) and that amount as shared by the prosthetic nucleus (e.g., load transferred to the annulus fibrosus) by moving the proximal cup 420 relative to the proximal bone anchor 344.

1166—Deliver jam nut to proximal bone anchor 344 to secure the position of the proximal cup 420.

1172—lose axial channel.

Details on the Creation of an Axial Channel

After that general introduction to the process, FIG. 13 provides a more detailed description of one set of steps that could be used to prepare an axial channel via an anterior trans-sacral axial approach for use with distal and proximal anchors having the same major diameter. Note that although FIG. 13 describes a process to provide an access channel for the delivery of a spinal motion preserving assembly to the L5/S1 motion segment, the use of spinal motion preservation assemblies is not limited to solely that motion segment. As much of the process for preparing the access channel is the same or similar to processes described in previous applications for this assignee, the steps are assumed to be relatively self-explanatory but are provided here as an outline that would be meaningful to one of ordinary skill in the art. As noted below, spinal motion preservation assemblies could be implemented with anchors of decreasing major diameters or with a single anchor. Those of ordinary skill in the art could modify the details provided in FIG. 13 and the related text to modify the axis channel preparation process accordingly.

1206—Place patient on table in a prone position.

1212—Make longitudinal incision just below and lateral to the coccyx using a scalpel, incision length of approximately 2 cm.

1218—Insert guide pin introducer with stylet under fluoroscopy into the presacral space.

1224—Check lateral and anterior/posterior fluoroscopes to verify location of guide pin introducer tip. Fluoroscopes will be consulted as needed for the remainder of procedure to continually verify instrument position and trajectory when necessary using lateral and anterior/posterior fluoroscope visualization.

1230—Advance guide pin introducer until it reaches desired entry point on sacral face. As noted above, the sacrum in an adult is a fused set of vertebrae given individual names S1 to S5. S1 is the most cephalad of these vertebrae.

1236—Remove stylet and replace with guide pin with handle.

1242—Determine proper trajectory and when aligned, tap guide pin into sacrum with slap hammer until guide pin crosses L5-S1 intervertebral disc space and secures itself in L5 vertebral body.

1248—Remove-guide pin handle and attach guide pin extension to guide pin.

1254—Remove guide pin introducer making sure that the guide pin remains in place.

1260—Pass 6 mm dilator over guide pin and begin driving dilator into the sacrum using the slap hammer over the guide pin.

1266—Continue driving 6 mm dilator into sacrum until the tip reaches the endplate of the sacrum just below the L5-S1 intervertebral disc space.

1272—Remove 6 mm dilator making sure guide pin remains in position and replace with 8 mm dilator.

1278—Drive 8 mm dilator into sacrum using slap hammer until tip reaches the endplate of the sacrum just below the L5-S1 intervertebral disc space.

1284—Remove 8 mm dilator making sure guide pin remains in position and replace with 10 mm dilator with sheath.

1290—Drive 10 mm dilator with sheath into sacrum using slap hammer until tip reaches the endplate of the sacrum just below the L5-S1 intervertebral disc space.

1296—Remove 10mm dilator body leaving sheath in place and verifying that the guide pin remains in position as well.

1302—Insert 9 mm cannulated drill over the guide pin and into the 10 mm dilator sheath.

1308—Twist drill through the sacrum and into L5-S1 disc space and then remove drill leaving guide pin in position.

1314—Insert 10 mm dilator body into its sheath and remove sheath from sacrum leaving guide pin in position.

1320—Pass 12 mm dilator over guide pin and drive into sacrum using the slap hammer until tip is in L5-S1 disc space.

1326—Remove 12 mm dilator making sure guide pin remains in position and replace with 13 mm dilator with sheath.

1332—Drive 13 mm dilator with sheath into sacrum using slap hammer until tip reaches into L5-S1 disc space.

1338—Remove 13 mm dilator body leaving sheath in place and then remove guide pin with extension.

1344—Insert 12.5 mm drill into 13 mm sheath and drill through sacrum into L5-S1 disc space.

1350—Remove drill and insert cutter body bushing into 13 mm sheath. The bushing takes up room in the sheath so that the cutter and the 9 mm drill both travel in a constrained space.

1356—Perform nucleectomy on L5-S1 disc space using radial cutters and tissue extractors being careful to maintain cartilage and endplates.

1362—Optional step: use small radial cutter to countersink endplate of sacrum to remove any chunks of endplate that could damage membrane during inflation. Much in the same way as drilling through plywood can cause a splintered edge around the perimeter of the newly created hole, there is some chance of creating protruding bone splinters when drilling through the endplate of the sacrum. It may reduce the chance of adverse interaction between bone splinters and the membrane if these bone splinters are broken off and removed.

1368—Insert 9 mm drill through cutter body bushing and drill into L5 approximately ⅔rds of the way through the L5 vertebral body.

1374—Remove drill and cutter body bushing from 13 mm sheath.

1380—Insert 12.5 mm drill and create larger bore in L5 approximately ⅔rd of the way through the vertebral body. This may vary based on the patient anatomy and the size of the distal anchor used.

1386—Remove drill and place guide pin with extension into bore.

1392—Pass 13 mm dilator body over wire and into sheath in order to facilitate removal of the 13 mm sheath while making sure that guide pin remains in position.

1398—Select exchange system components based on the angle between the trajectory and the anterior sacral face (choosing from component for either 30 degrees or 45 degrees). As best seen in FIG. 3, the anterior face of the sacrum is sloped. Angle 258 in FIG. 3 is approximately 40 degrees. Not surprisingly, it is helpful to have a system that approximates the slope in the exchange cannula intended to contact the anterior face of the sacrum to establish an exchange cannula that protects components during insertion into the access channel.

Figure 15:
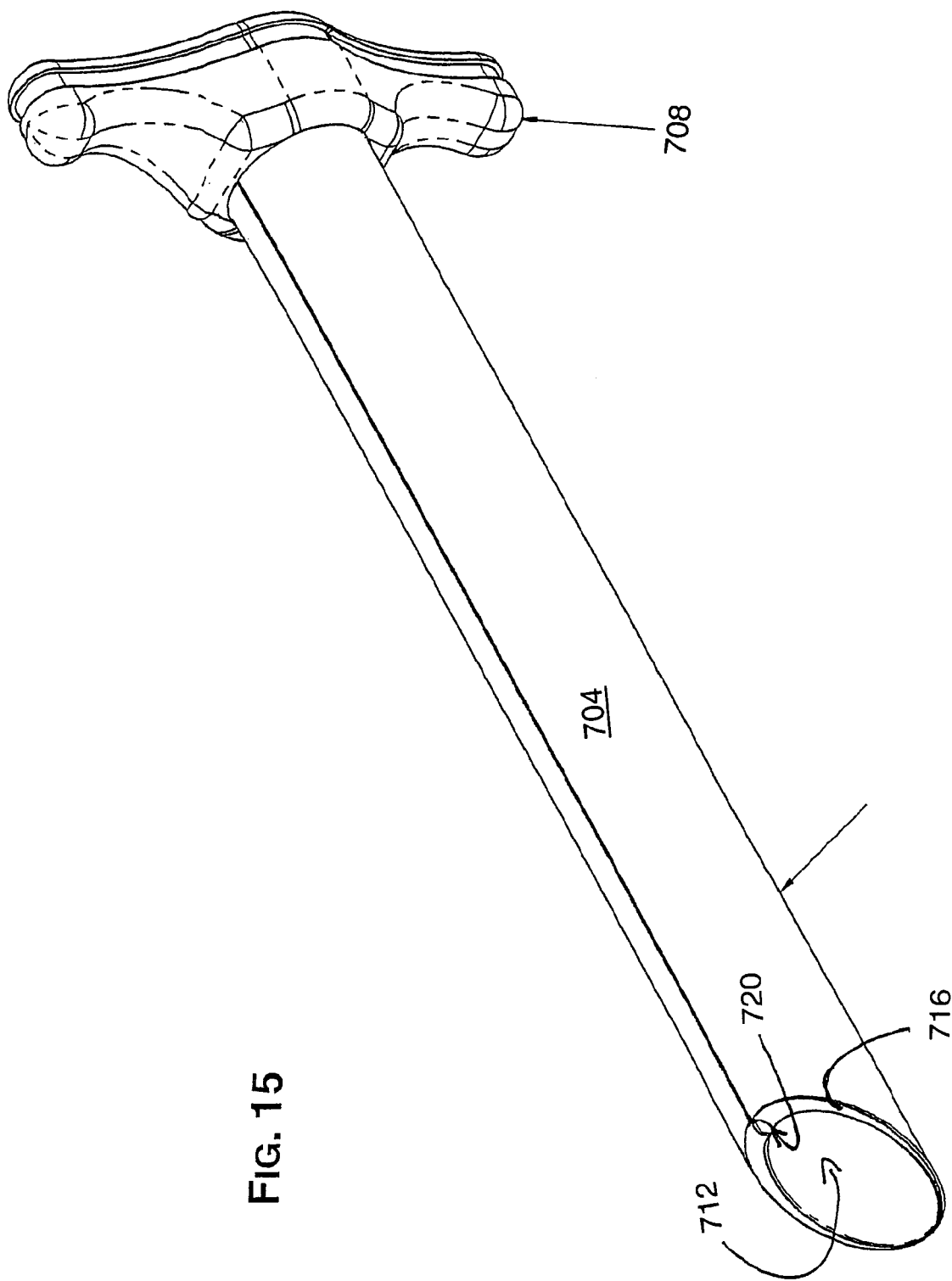
FIG. 15 is a perspective view of exchange cannula 704.

FIG. 15 shows a perspective view of exchange cannula 704. The exchange cannula 704 has a handle 708, a main cannula 712 that runs from the handle to the angled distal face 716. In this case the distal face 716 is sloped at 45 degrees. A wire tube 720 runs along one wall of the exchange cannula 704 and through the handle 708 so that the exchange cannula 708 can be pinned to the sacrum to prevent the exchange cannula from sliding down the anterior wall of the sacrum, as described and disclosed in co-pending and commonly assigned U.S. patent application Ser. No. 11/501,351 filed Aug. 9, 2006, herein incorporated by reference into this disclosure

1404—Insert chosen exchange bushing over the guide pin into the sacral bore.

1410—Pass chosen exchange cannula over exchange bushing making sure that the distal face of the exchange cannula is flush to the anterior face of the sacrum.

1416—Insert fixation wire through wire tube 720 in the exchange cannula 704 and into sacrum using extended pin vise. (Pin vise allows the pin to be fed through the vise and the vise tightened in order to give the gloved surgeon something larger to hold and manipulate than the wire itself). Those of skill in the art will be familiar with a Kirschner pin vise. A pin vise found to be suitable for this use is sold as part number 30008 by IMEX™ Veterinary, Inc. of Longview, Tex. One may want to extend the snout on the front of the pin vise to adjust the pin vise for this particular application.

1422—Bend fixation wire securing exchange cannula 704 to sacrum (FIG. 3, element 116) and remove exchange bushing.

1428—End of access channel preparation.

After the access channel is prepared, the process of delivering a spinal motion preservation assembly as shown in FIGS. 3-7 proceeds as described in FIG. 14.

Components in the Dual Anchor Driver

In order to understand the steps in flow chart shown in FIG. 14, it will be necessary to introduce and describe the components in various drivers used in the process. The first driver is the dual anchor driver 2000. This driver and the components of the driver are FIGS. 16-22.

FIG. 16 is a perspective view of the dual anchor driver with a quarter round removed to better show the components. The operation of the dual anchor driver 2000 will be better appreciated after review of the use of the driver in the various steps in FIG. 15, but FIGS. 16-22 provide an introduction.

A retention rod 2004 runs through the center of the dual anchor driver 2000. Rotation of the retention rod knob 2032 causes the threaded distal tip 2036 of the retention rod 2004 to rotate relative to the dual anchor driver 2000 to selectively engage or disengage the internal threaded section 368 of the distal bone anchor 340. FIG. 17 is a perspective view of retention rod 2004 and shows the retention rod knob 2032 and the threaded distal tip 2036.

The retention rod extends through an insertion tip 2008. Details of the insertion tip may be seen in FIGS. 18 and 19. FIG. 18 is a perspective view with a quarter round removed. FIG. 19 is a cross section. In this case, the insertion tip 2008 has a hexagonal driving section 2040. Those of skill in the art will recognize that other shapes could be used for the insertion tip. Note that distal to the driving section 2040 is a non-driving section 2044 which will be referenced below.

The insertion tip 2008 is engaged with the driver shaft 2012. Through a combination of a corresponding male hexagonal proximal end 2048 of the insertion tip 2008 and a female hexagonal distal end 2052 (shown best in FIG. 20) and a pinned engagement, the insertion tip 2008 may be driven by the driver shaft 2012 when the driver shaft 2012 is rotated by the handle 2028.

Figure 23:
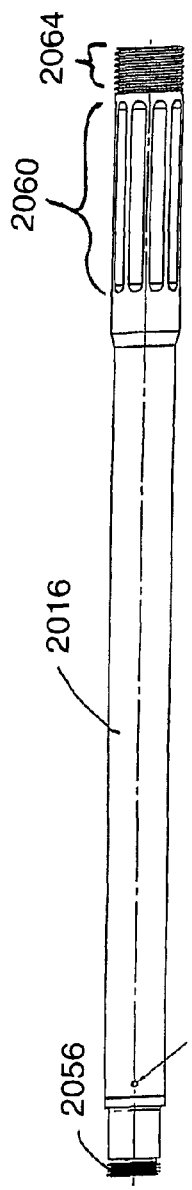
FIG. 23 is a side view of distraction sleeve 2016.
Figure 24:
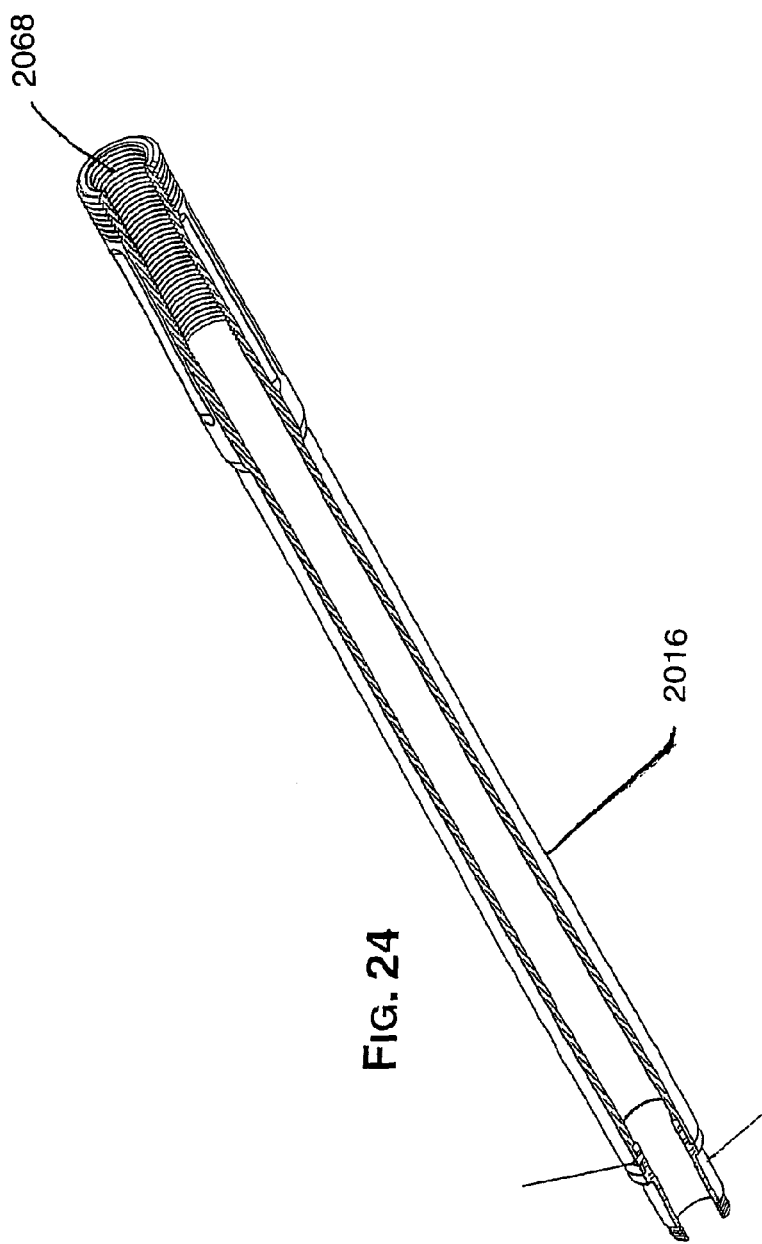
FIG. 24 is a perspective view with a quarter round section removed of a distraction sleeve 2016.

The driver shaft 2012 lies within distraction sleeve 2016. Distraction sleeve 2016 may translate or rotate relative to driver shaft 2012 as referenced below. FIG. 23 shows a side view of the distraction sleeve 2016. FIG. 24 shows a perspective view with a quarter round section removed. The distraction sleeve 2016 had a set of male threads 2056 on the distal end of the distraction sleeve 2016 and another set of male threads 2064 on the proximal end of the distraction sleeve 2016. A textured section 2060 facilitates holding or moving the distraction sleeve 2016 while wearing surgical gloves. A set of female threads 2068 in the proximal end of the distraction sleeve 2016 will be discussed in connection with the distraction steps.

FIG. 21 is a cross section view of retainer lock 2020. Retainer lock 2020 has a threaded section 2072 for engagement with the proximal female threads 2064 on the distraction sleeve 2016 (See FIG. 23). Retainer lock 2020 also has an unthreaded section 2076 to allow the retainer lock 2020 to move a fixed amount relative to the flange 2080 of lock stop 2024 as shown in FIG. 22. Lock stop 2024 is welded to the handle 2028.

Returning now to the flow chart in FIG. 14, the first step in the delivery of a spinal motion preservation assembly of the type depicted in FIGS. 3-7 is step 1504.

1504—Load the proximal bone anchor 344 in the dual anchor driver 2000 and engage the threaded section 2056 of distraction sleeve 2016 (See FIG. 23) into the set of internal threads 416 in the proximal bone anchor 344 to secure the proximal bone anchor 344 to the dual anchor driver 2000. Lock stop 2024 is welded to handle 2028 and thus constrains the movement of retainer lock 2020.

1510—Engage the internal threads 2072 on retainer lock 2020 with external threads 2064 on the distraction sleeve 2016.

1516—Place the distal bone anchor 340 on the dual anchor driver 2000 being careful to align the distal bone anchor 340 with the proximal bone anchor 344 anchors using the alignment marks 472 placed longitudinally on the external threads 356 and 404 of each anchor.

1522—Thread the distal tip 2036 of the retention rod 2004 by rotating the retention rod knob 2032 to cause the retention rod 2004 to rotate relative to the outer layers of the dual anchor driver 2000 and the distal bone anchor 340 and to engage internal threaded section 368 of the distal bone anchor 340.

1528—Place dual anchor driver 2000 with both anchors attached over the guide pin with extension and through the main cannula 712 in the exchange cannula 704 and begin rotating the driver 2000 to axially advance the anchors into the distal and proximal vertebral bodies. Lateral fluoroscopy may be useful for visualization of the insertion steps. Initially, the external threads 356 on the distal bone anchor 340 will create a helical thread path in the proximal vertebral body 308 and at some point the distal bone anchor 340 will be creating a helical thread path in the distal vertebral body 304 while the external threads 404 on the proximal bone anchor 344 engage with the previously created helical thread path in the proximal vertebral body 308 as the two anchors are being delivered by timed delivery based on a combination of the spacing of the anchors on the dual anchor driver 2004 and the use of the alignment marks 472.

1534—Continue rotating dual anchor driver 2000 to advance the distal and proximal bone anchors into distal and proximal vertebral bodies until the proximal face 370 (FIG. 5) of the distal bone anchor 340 is approximately flush with the endplate on the distal end of the intervertebral disc space 312.

1540—Release the distal bone anchor 340 from the dual anchor driver 2000 by rotating the retention rod knob 2032 and removing the retention rod 2004 from the dual anchor driver 2000.

1546—Unscrew the retainer lock 2020 on the dual anchor driver 2000 to release the external threads 2064 on the distraction sleeve 2016.

1552—Partially withdraw the dual anchor driver 2000 from the axial channel 212 so that the driving section 2040 of the insertion tip 2008 is no longer engaged with the hex ridges 374 in the distal bone anchor 340 but remains engaged with driver engagement section 378 in the proximal bone anchor 344 (as shown in FIGS. 4-6). The non-driving section 2044 of the insertion tip 2008 may remain in the cavity 364 (FIG. 5) in the distal bone anchor 340 as that will not impart rotation to the distal bone anchor 340.

1558—Selectively adjust the position of the proximal bone anchor 344. Often this may require advancing the proximal bone anchor 344 further into the proximal vertebral body 308 (in this case the sacrum). It may require retracting the proximal bone anchor 344 in some instances. Selective use of insertion tips of different axial lengths can be employed to cause the timed delivery of the two bone anchors to initially have a particular spacing between anchors. (normally an integer multiple of the distance between adjacent external threads). The distance selected as the initial distance between bone anchors may be clinically indicated by the specific motion segment receiving therapy and the size of the patient's intervertebral disc space. An initial spacing of approximately 10 millimeters may be appropriate for some patients receiving therapy to the L5/S1 motion segment.

After disengaging the distal bone anchor 340 from the dual anchor driver 2000, the proximal bone anchor 344 can be advanced or retracted to be any selected distance from the distal bone anchor. The proximal bone anchor 344 may be positioned to have the distal face 414 (FIG. 4) of the proximal bone anchor 344 positioned approximately flush with the endplate of the proximal vertebral body 308 (in this case the sacrum).

1564—Remove the dual anchor driver 2000 with the exception of the distraction sleeve 2016.

1570—Remove the extended guide pin.

The Distraction Driver and the Membrane Sheath

The next series of steps are performed through use of a distraction driver. As with the discussion of the steps associated with the dual anchor driver 2000, it is useful to start with a description of the driver and then discuss how the driver is used in context with the delivery process that ensures protection of the membrane during (intact) deployment.

Figure 25:
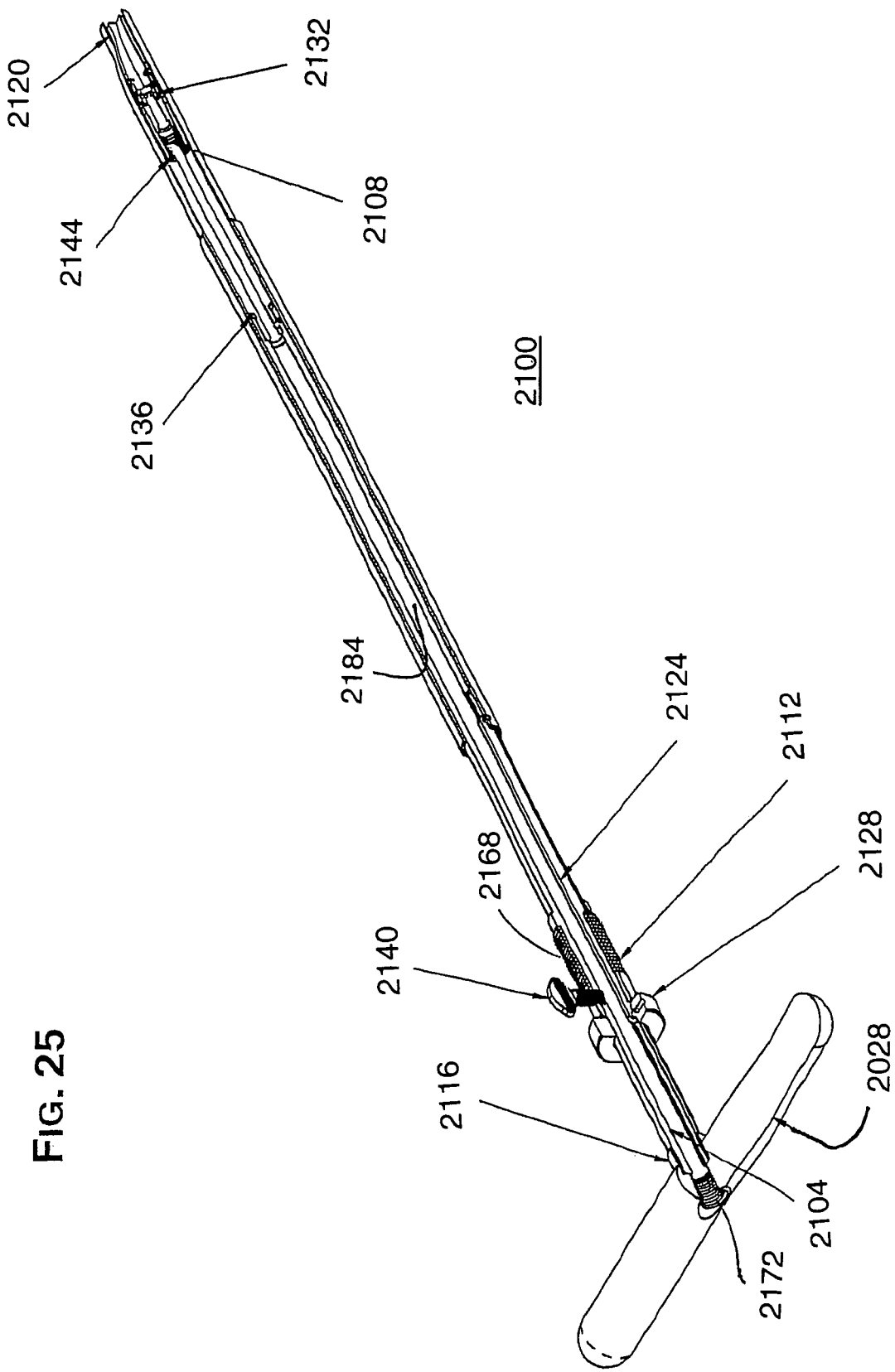
FIG. 25 is a perspective view of distraction driver 2100 with a quarter round removed.
Figure 26:
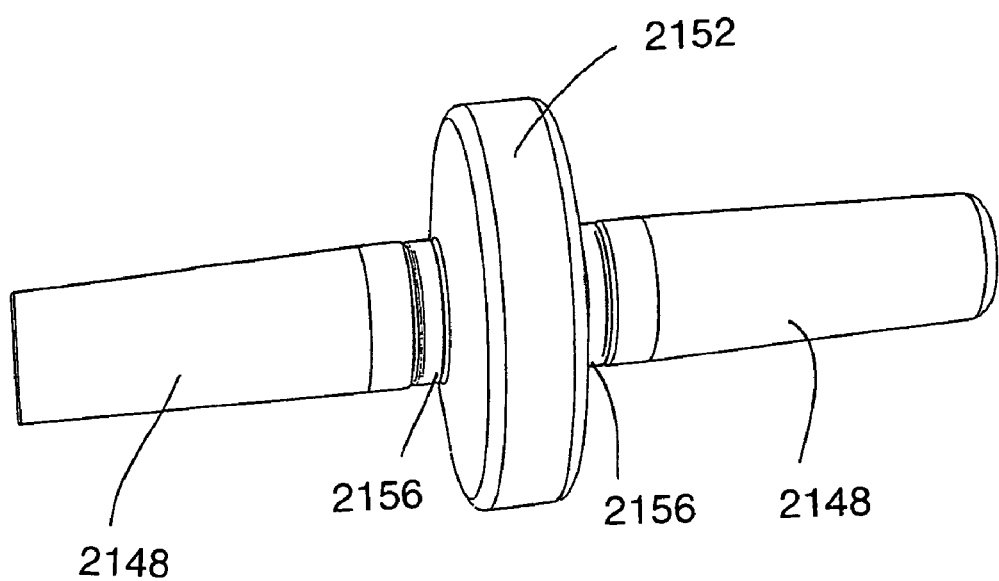
FIG. 26 is a side perspective view of a membrane tip 2148 with a membrane 2152.

FIG. 25 is a perspective view of distraction driver 2100 with a quarter round removed. The distraction driver 2100 has distraction shaft 2104, distraction driver tip 2108, distraction driver sleeve 2112, and sizing sleeve 2116. This driver uses the same type of handle 2028 that was introduced in connection with the dual anchor driver 2000. This handle is used in a number of devices. Distraction driver 2100 has a membrane sheath 2120 that is advanced to cover a membrane 2152 attached to a membrane tip 2148 by two retainer rings 2156 (See FIG. 26). This membrane 2152 is to be delivered to the intervertebral disc space (see 312 in FIG. 3) between the two implanted anchors and then filled. The membrane sheath 2120 is shown in FIG. 25 in the advanced position covering the membrane tip assembly 2132. The membrane sheath 2120 may be retracted by pulling on membrane sheath ring 2128 as the membrane sheath 2120 moves along two membrane sheath keys 2124 (only one visible here). The distraction driver 2100 includes proximal O-ring 2136 and distal O-ring 2144. Thumbscrew 2140 will be discussed in more detail below.

Figure 27:
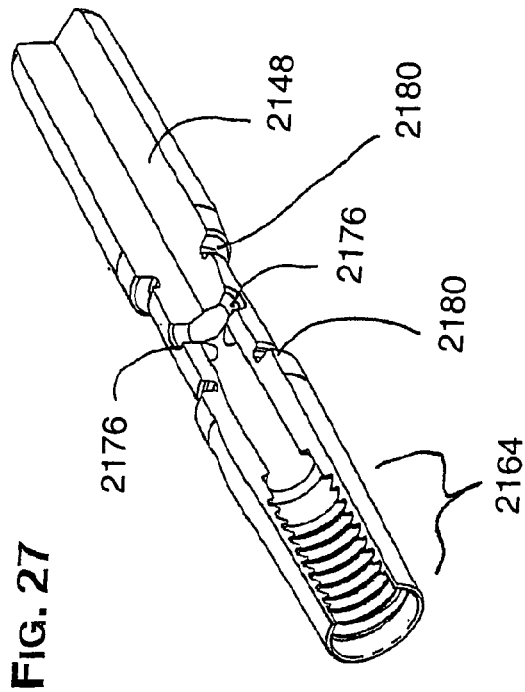
FIG. 27 is a perspective view with a quarter round removed of the membrane tip 2148.
Figure 28:
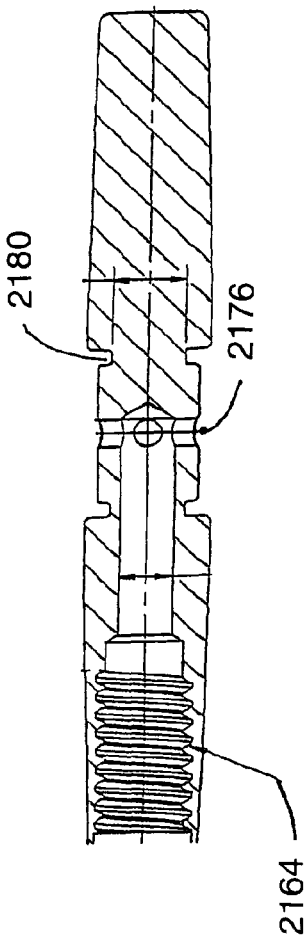
FIG. 28 is a cross section of the membrane tip 2148.
Figure 29:
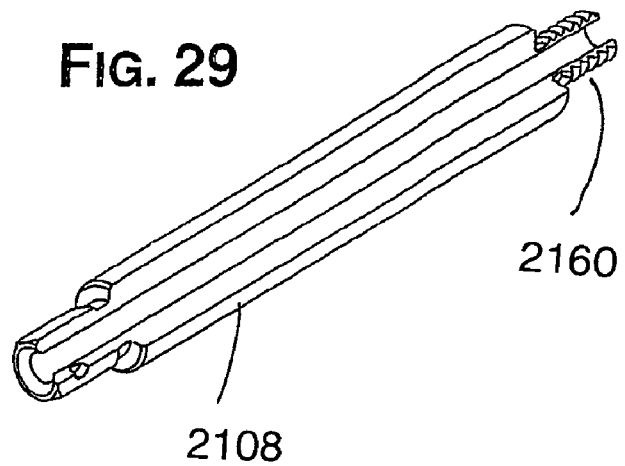
FIG. 29 is a perspective view with quarter round removed of a distraction driver tip 2108.
Figure 30:
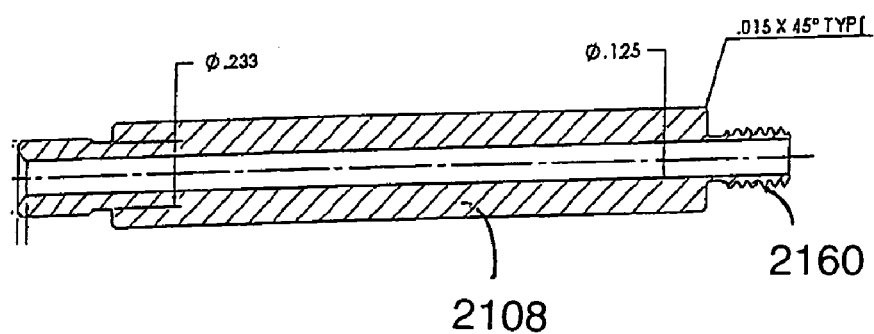
FIG. 30 is a cross section of the distraction driver tip 2108.

1576—Assemble distraction driver 2100. This step includes threading the membrane tip assembly 2132 onto distraction driver tip 2108. As shown in FIG. 27, a perspective view with a quarter round removed of the membrane tip 2148 and FIG. 28 a cross section of the membrane tip 2148 in conjunction with FIGS. 29 and 30 showing a perspective view with a quarter round removed and a cross section of the distraction driver tip 2108. The engagement of the membrane tip assembly 2132 with the distraction driver tip 2108 occurs through engaging the external threads 2160 on the distraction driver tip 2108 with the internal threads 2164.

After the membrane tip assembly 2132 is engaged with the distraction driver tip 2108, the membrane sheath 2120 may be advanced to cover the preformed membrane 2152. This step may be facilitated by an optional step of pulling a vacuum at the proximal end of the handle 2028. While the central cavity 2184 in distraction driver 2100, may not be sufficiently air tight to able to hold a vacuum, this process will tend to remove air from the membrane 2152. A biocompatible lubricant that is also compatible with the membrane 2152 may be used to help the process of extending the membrane sheath 2120 over the membrane 2152.

Step 1576 includes engaging the thumbscrew 2140 to secure distraction driver sleeve 2112 to distraction shaft 2104 by engaging an indentation (visible in FIG. 25) in the distraction shaft 2104.

1582—Insert the distal end of distraction driver 2100 through distraction sleeve 2016 left in the axial channel 212 after delivery and positioning of the two bone anchors (340 & 344). The insertion continues until the distal end of the distraction driver 2100 arrives in the distal bone anchor 340. The external threads 2056 on distraction sleeve 2016 remain engaged with the internal threads 416 in the proximal bone anchor 344.

1588—Pull the membrane sheath ring 2132 to move the membrane sheath 2120 to the retracted position. The membrane sheath ring 2132 is pinned to two membrane sheath keys 2124 which are in turn connected via pins to the proximal end of membrane sheath 2120. The membrane sheath 2120 may be retracted now as it has served its purpose of protecting the membrane 2152 from any possible damage while moving to the intervertebral disc space 312.

1594—While holding the textured section 2060 of the distraction sleeve 2016 stationary with one hand, turn distraction driver 2100 until desired distraction is achieved. The distraction is achieved by the threaded engagement of the internal threads 2068 of the distraction sleeve 2016 (which are held stationary) with the external threads 2168 on the distraction driver 2100. The rotation of the distraction driver 2100 causes axial advancement of the distraction driver 2100 so that the distal end of the membrane tip 2148 pushes on the interior cavity of the implanted distal bone anchor 340 while rotating relative to the distal bone anchor 340. Thus, the distraction driver 2100 moves axially forward relative to the distraction sleeve 2016 which is threadedly engaged with proximal anchor 344 which is in turn threadedly engaged with proximal vertebral body 308. This movement causes the distal vertebral body 304 to move axially and away from the proximal vertebral body 308 and thus increases the size of the intervertebral disc space 312. Note that a distraction driver could be created that engages directly with the set of internal threads 416 in the proximal bone anchor 344. (U.S. patent application Ser. No. 11/259,614 filed Oct. 25, 2005 (published as US 2006/0155297 A1) and referenced above includes a description of such a distraction driver and the relevant disclosure is incorporated herein by reference.) The use of the distraction sleeve 2016 allows a longer set of internal threads 2068 to be used by the distraction driver while the distraction sleeve 2016 is connected to the internal thread 416 in the proximal bone anchor 344. Effectively the distraction sleeve 2016 is a distraction range extender as it increases the maximum possible distraction beyond the length of the internal threads 416 in the proximal bone anchor 344. If additional mechanical advantage is desired, the thread pitch in internal threads 2068 in distraction sleeve 2016 could be made with a greater number of threads per inch than used in internal threads 416 so that it takes a greater number of turns of the distraction driver for a given amount of distraction and a proportionate decrease in the amount of required force.

1600—Assemble and prepare prosthetic nucleus material delivery tools. In this instance the prosthetic nucleus material is silicone. The dual chamber silicone container is attached to an injection dispenser (not shown). A mixing tip (not shown) is threaded to the internal threads 2172 in handle 2028 of distraction driver 2100 (see FIG. 25). The silicone dispenser is attached to the mixing tip.

1606—Inject material through distraction driver 2100 and into the membrane 2152 implant under real-time fluoroscopic imaging. Note that the distraction driver 2100 continues to hold the increased (distracted) spacing of the intervertebral disc space 312. The silicone flows through the mixing tip (not shown) which is threaded to the internal threads 2172 in the back of the handle 2028 and up through the central cavity 2184 of the distraction driver 2100 to the membrane tip 2148 and out through a set of one or more ports 2176. Beyond the ports 2176, the membrane tip 2148 is solid without any path for silicone.

Use pressure to drive silicone to fill membrane 2152 and cavity created during nucleectomy. Depending on the size of the cavity and the size of the selected membrane 2152, the volume of silicone placed in the membrane may not fully extend the membrane 2152 and there will be wrinkles or other irregularities in the surface of the membrane 2152. In some cases the preformed shape of the membrane 2152 may be expanded by the addition of silicone under pressure in order to fill the available space. However, the amount of expansion of the membrane 2152 will be more like the expansion of a bladder in a soccer ball as it is inflated than the massive change in shape of a balloon as the membrane starts out as at least an approximation of the final shape of a filled membrane. The reduction in the amount of expansion of a membrane necessary to fill the void left by the nucleectomy may make the less expanded membrane more resistant to damage from contact with sharp surfaces external to the membrane. (For completeness, it is appropriate to note that the use of a membrane that starts essentially as a flat ring around the membrane tip and expands under the pressure of the silicone application to fill the void in the intervertebral disc space is a viable alternative to the use of a preformed membrane described above.)

1612—Allow ample time for prosthetic nucleus material to cure. When the distraction driver 2100 is removed, the silicone filled membrane 2152 will be needed to maintain the distraction. (Some reduction in distraction may be seen as the distraction driver is removed leading experienced operators to optionally impose more than the desired distraction with the distraction driver to anticipate the distraction reduction.) Do not proceed to the next step until the silicone is cured.

1618—Disengage distraction driver sleeve 2112 from distraction sleeve 2016 by first unscrewing thumbscrew 2140 to release the engagement between the distraction driver sleeve 2112 and the distraction shaft 2104. Once the distraction driver sleeve 2112 is free to rotate relative to the rest of the distraction driver 2100, then rotate the distraction driver sleeve 2112 to disengage the internal threads 2068 of the distraction sleeve 2016.

1624—While holding distraction sleeve 2016 which is still engaged with the proximal bone anchor 344, pull the distraction driver 2100 to pull the membrane tip 2148 out of the distal bone anchor 340 and the proximal bone anchor 344 thus separating the membrane 2152 filled with silicone from the distraction driver 2100. As the membrane 2152 is attached to the membrane tip 2148 and held by the retainer rings 2156, withdrawing the membrane tip 2148 with the rest of the distraction driver 2100 while leaving the membrane 2152 filled with cured prosthetic nucleus material (such as silicone) requires either ripping of the membrane 2152 at the retainer rings 2156 or pulling the membrane 2152 from under the retainer rings 2156 or some combination of ripping and pulling. Thus, removing the distraction driver 2100 may require a fair amount of force.

The silicone will have cured within the membrane tip 2148 as well as out in the membrane 2152 and the silicone is apt to break at the ports 2176. Seal ring 396 (best seen in FIG. 6) helps keep the withdrawal of the membrane tip 2148 from introducing small pieces of silicone into the internal threads 416 in the proximal bone anchor 344.

Turning now to FIGS. 31-36, the next driver is the distal cup driver 2200. This driver is used to drive the distal cup 372 to engage the external threads 376 on the distal cup 372 with the internal threaded section 368 of the distal bone anchor 340. The driver engages the hex ridges 394 (best seen in FIG. 5). If the distal cup 372 is inserted into a distal anchor 340 outside of the body then the driver design could be relatively simple. However, as the distal cup 372 must first be delivered through the axial channel 212 before insertion into the distal bone anchor 340, it is useful to have the distal cup driver 2200 engage the distal cup 372 to retain the distal cup 372 on the end of the driver.

The distal cup driver 2200 is shown in FIG. 31 with expanding mandrel 2204 on the end of the mandrel shaft 2224. FIGS. 32-36 provide additional views of components in a distal cup driver 2200. An expansion plug 2208 is at the distal end of a plug shaft 2228 that runs through the center cavity of the mandrel shaft 2224. The external threads 2232 on the proximal end of the plug shaft 2228 are threadedly engaged with handle 2212. A knob 2216 has an internal cavity 2244 that receives the knob engagement section 2236. A screw 2220 can be inserted in the proximal end of the knob 2216 to engage internal threads 2240 in the knob engagement section 2236 of the plug shaft 2228.

1630—Engage the proximal end of the distal cup 372 with the distal end of the distal cup driver 2200 by aligning the hex ridges 394 in the distal cup 372 with the expanding mandrel 2204. Turn knob 2216 clockwise to cause the external threads 2232 on the proximal end of the plug shaft 2228 to move relative to the handle 2212 to retract the expansion plug 2208 and splay the expanding mandrel 2204 within the distal cup 372 so that the distal cup 372 is retained by the distal end of the distal cup driver 2200. While other designs for distal cups could be made within the teachings of the present disclosure, it is advantageous to have a distal cup driver that makes positive engagement with the distal cup without use of a retention tube that would engage a threaded cavity located in the bearing surface for the pivot as this would tend to lead to wear issues.

1636—Insert the distal cup 372 attached to the end of the distal cup driver 2200 through the distraction sleeve 2016 (which is still threadedly engaged with the proximal bone anchor 344) and into the distal bone anchor 340. Rotate the handle 2212 on the distal cup driver 2200 to engage the external threads 376 on the distal cup 372 with the internal threaded section 368 of the distal bone anchor 340 and advance the distal cup 372 until seated. Once the change in resistance is felt as the distal cup 372 is seated, the rotation of the distal cup driver 2200 should be stopped to avoid inadvertently advancing the distal bone anchor 340 in the distal vertebral body 304.

1642—Release the distal cup 372 from the distal cup driver 2200 by turning the knob 2216 counter-clockwise.

1648—Remove the distal cup driver 2200 from the axial channel 212 and the distraction sleeve 2016.

The next driver is the support member driver 2260 shown in FIGS. 37 and 38. FIG. 37 is a perspective view of a support member driver 2260 and FIG. 38 is a cross section of a support member driver 2260. The components of the support member driver 2260 are a support member driver shaft 2264 with a distal end 2268 of the support member driver shaft 2264. In one implementation of the support member driver 2260, the distal end 2268 of the support member driver shaft 2264 has the same bore diameter as the maximum cross sections of the distal end 384 and proximal end 388 of the support member 352 (in this implementation both ends are the same as best seen in FIG. 5). The distal end 2268 is adapted to receive the entire support member 352 within the support member driver shaft 2264. Because of the close dimensional tolerance, the support member 352 is engaged with the support member driver 2260 and will not fall away from the driver until selectively expelled. The support member driver shaft 2264 includes a textured section 2276 near the proximal end 2272 of the support member driver shaft 2264. A distal end 2288 of push rod 2280 may be inserted into the proximal end 2272 of the support member driver shaft 2264 and extended up to make contact with the proximal end 388 of the support member 352. Pushing on the support member 352 with sufficient force by advancing the textured section 2284 of the push rod 2280 relative to the support member driver shaft 2264 will deliver the support member 352. With this introduction to this driver, the next step in the delivery process can be appreciated.

1654—Load the proximal end 388 of support member 352 into the distal end 2268 of the support member driver shaft 2264 and continue to insert the support member until it is all within the support member driver shaft 2264. The push rod 2280 may then be inserted into the proximal end 2272 of the support member drive shaft 2264 and advanced without exerting force to expel the support member 352.

1660—Insert the loaded support member driver 2260 into the axial channel 212 through the distraction sleeve 2016 (which is still threadedly engaged with the proximal bone anchor 344) and into the proximal bone anchor 344 until the shoulder 2292 on the support member driver shaft 2264 bottoms out against the seal ring 396.

1666—Insert the distal end 392 of the support member 352 into the distal cup 372 by pushing the push rod 2280 towards the distal cup 372 while holding onto the textured section 2276 of the support member driver shaft 2264.

1672—Remove the support member driver 2260 verifying through fluoroscopy that the distal end 392 of the support member 352 remains in position within the distal cup 372.

1678—Place distal end of the dual anchor driver 2000 back through the distraction sleeve 2016 so the driving section 2040 of the insertion tip 2008 becomes engaged with driver engagement section 378 in the proximal bone anchor 344 in order to facilitate removal of the distraction sleeve 2016.

1684—Turn distraction sleeve 2016 counter-clockwise after the insertion tip 2008 is engaged with the driver engagement section 378 and is holding the proximal anchor 344 stationary. After unthreading the distraction sleeve 2016 from the proximal anchor 344, remove the distraction sleeve 2016 with the dual anchor driver 2100 from the exchange cannula 704.

The next driver in the delivery process is a driver used to deliver first the proximal cup 420 and then the jam nut 440. The design of the proximal cup 420 and the jam nut 440 allow the use of a single driver. This is optional and other designs could use different drivers or at least different tips on the driver to deliver these two components.

FIG. 39 is a perspective view of a dual use driver 2300. FIG. 40 is a cross section of the dual use driver 2300. From these two drawings, the major components of the dual use driver 2300 can be introduced as: the insertion tip 2304, the driver shaft 2308, a pair of retaining pins 2312 (only one is visible) to hold the insertion tip 2304 to the driver shaft 2308, a retention rod 2316, and a driver handle 2028. FIG. 41 shows an enlarged perspective view of insertion tip 2304 with the distal end in the foreground. The distal end of the insertion tip 2304 is a polygonal driver section 2324 which in this case is hexagonal and suitable to engage the driver engagement section 428 in proximal cup 420 (best seen in FIG. 7) or the driver engagement section 448 in jam nut 440 (best seen in FIG. 7). FIG. 41 also shows one of the two pin engagement holes 2328 used for engagement with a retaining pin 2312 (see FIG. 39). FIG. 41 also shows that the distal face 2332 of the insertion tip 2304 has a central bore 2336. FIG. 42 shows a perspective view of retention rod 2316 including knob 2340 and threaded tip 2344.

A related component is the proximal anchor stabilizer 2380 shown in a perspective view in FIG. 43 and in a side view in FIG. 44 with an enlarged perspective view of stabilizer tip 2392 in FIG. 45. The proximal anchor stabilizer 2380 has a stabilizer tip 2392 (having the stabilizer fingers 2384) connected by one or more stabilizer pins 2396 (for example two pins) to the stabilizer shaft 2388.

1690—Place proximal anchor stabilizer 2380 over the shaft of the dual use driver 2300 with the engagement fingers 2384 facing towards the distal end of the dual use driver 2300.

1696—Place the proximal cup 420 onto the polygonal driver section 2324 to engage the driver engagement section 428 in the proximal cup 420.

1702—Pass the threaded tip 2344 of the retention rod 2316 through the handle 2028, driver shaft 2308, and the bore 2336 in the insertion tip 2304 to make contact with the threaded cavity 432 in the proximal cup 420. Engage the threaded tip 2344 with the threaded cavity 432 to secure the proximal cup 420 to the dual use driver 2300.

1708—Insert the proximal cup 420 and distal end of the dual use driver 2300 through the exchange cannula 704 and begin threading the set of external threads 424 on the proximal cup 420 (best seen in FIG. 5) into the set of internal threads 416 in the proximal bone anchor 344 (while monitoring the fluoroscopes to ensure that the proximal anchor 344 is not advancing further into the proximal vertebral body 308).

If proximal anchor 344 begins to rotate and thus advance at any point during proximal cup insertion or secondary distraction (discussed below), the proximal anchor stabilizer 2380 may be advanced axially to engage the stabilizer fingers 2384 with the slots 456 in the proximal bone anchor 344.

1714—Continue advancing the proximal cup 420 until it contacts the proximal end 388 of the support member 352.

1720—Selectively advance the proximal cup 420 beyond initial contact with the support member 352 to impose a desired amount of secondary distraction on intervertebral disc space 312 as continued advancement will move the proximal cup 420 axially relative to the proximal bone anchor 344 which is being held in place by the proximal anchor stabilizer 2380 (should the anchor be inclined to move). The proximal bone anchor 344 is engaged with the proximal vertebral body 308. Thus, as the proximal cup 420 continues to advance, the proximal cup 420 pushes the support member 352 axially. The support member 352 in turn pushes on the distal cup 372 in the distal bone anchor 340 in the distal vertebral body 304 to move the distal vertebral body 304 relative to the proximal vertebral body 308 to impose additional distraction.

The selective advancement of the proximal cup 420 alters the compressive forces borne by the support member 352 as opposed to the silicon filled membrane 2152. In an extreme case where the proximal cup is placed so far away from the distal cup so that the support member cannot make contact with both cups, the support member bears no compressive force and all the compressive force must pass through the silicone filled membrane 2152. Under sufficient compressive loading, the elastically deformable silicone filled membrane compresses in the Z axis while bulging radially until the support member 352 makes contact with both the proximal cup 420 and the distal cup 372 so that some of the compressive force passes through the support member 352.

If in contrast that proximal cup 420 is advanced far enough, the increased distraction of the intervertebral disc space may cause the silicone filled membrane 2152 to lose contact with one or both vertebral bodies.

As the surgery is performed with the patient in the prone position (which facilitates distraction), the loading of the motion preservation assembly will change when the patient assumes a non-horizontal position. The surgeon adjusting the distribution of loading during the delivery of a spinal motion preservation assembly may wish to anticipate the loading change when the patient eventually assumes a vertical orientation.

1724—Turn the knob 2340 on the retention rod 2316 counter-clockwise to release the threaded tip 2344 from the proximal cup 420.

1730—Remove the dual use driver 2300 and the proximal anchor stabilizer 2380 from the exchange cannula 704.

1736—Leaving the proximal anchor stabilizer 2380 on the dual use driver 2300, place the jam nut 440 on the polygonal driver section 2324 of the insertion tip 2304.

1742—Pass the threaded tip 2344 of the retention rod 2316 through: the handle 2028, driver shaft 2308, and the bore 2336 in the insertion tip 2304 to make contact with the threaded cavity 452 in the jam nut 440. Engage the threaded tip 2344 with the threaded cavity 452 to secure the jam nut 440 to the dual use driver 2300.

1748—Insert the jam nut 440 and distal end of the dual use driver 2300 through the exchange cannula 704 and begin threading the set of external threads 444 on the jam nut 440 (best seen in FIG. 5) into the set of internal threads 416 in the proximal bone anchor 344 (while monitoring the fluoroscopes to ensure that the proximal anchor 344 is not advancing further into the proximal vertebral body 308).

If proximal anchor 344 begins to rotate and thus advance at any point during insertion of the jam nut 440, the proximal anchor stabilizer 2380 may be advanced axially to engage the stabilizer fingers 2384 with the slots 456 on the proximal bone anchor 344.

1754—Continue advancing the jam nut 440 until it is tight against the proximal cup 420.

1760—Turn the knob 2340 on the retention rod 2316 counter-clockwise to release the threaded tip 2344 from the jam nut 440.

1766—Remove the dual use driver 2300 and the proximal anchor stabilizer 2380 from the exchange cannula 704.

1772—Verify completion of steps with fluoroscopy and remove exchange cannula 704 after first removing the fixation wire connecting the wire tube 720 of the exchange cannula 704 to the sacrum 116.

1778—Close the axial channel between the sacrum and the skin through conventional means.

Alternative Implementations

Introduction of Elastically Deformable Components.

The example shown in FIGS. 3-7 does not include an elastomeric component or another elastically deformable component such as a spring that provides for elastic deformation of the spinal motion preservation assembly during a compressive load asserted in the Z direction. (Seal ring 396 while likely to be elastomeric, is not positioned in the example shown in FIGS. 3-7 in such a way to provide this functionality).

Machined Springs

Figure 46:
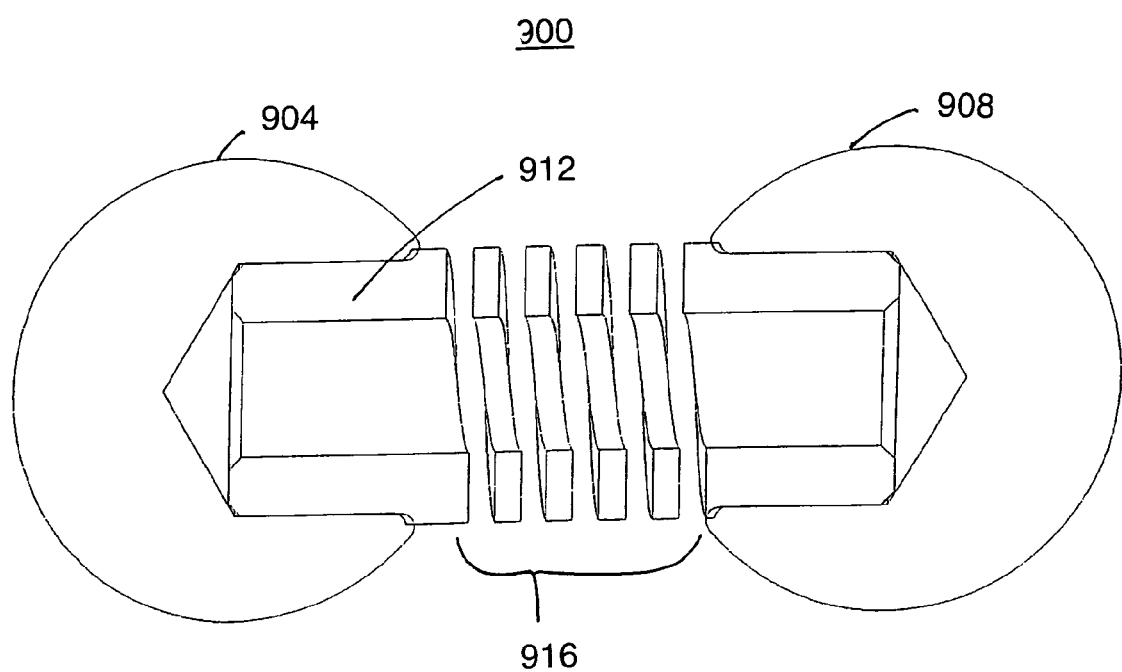
FIG. 46 illustrates a cross section of a support member 900 having a machined spring 916.

FIG. 46 illustrates a cross section of a support member 900 with: a first end 904, a second end 908, and a machined hollow rod 912 connecting the two ends. The machined hollow rod has a section that is a machined spring 916. Springs machined into hollow rods (as opposed to springs created from coil stock) can be made with great precision which decreases the variation between machined springs.

Elastomeric Component is Part of the Distal Cup

Figure 47:
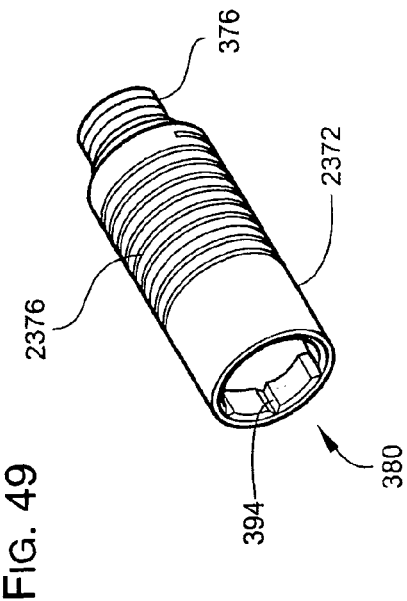
FIG. 47 is a side view of the modified distal cup 2372.
Figure 48:
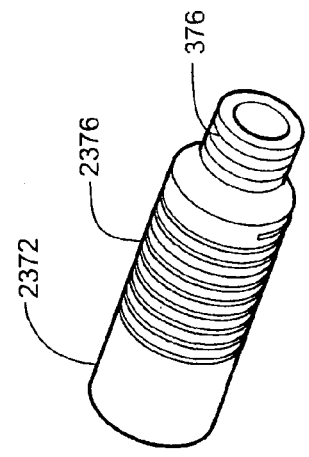
FIG. 48 is a cross section of the modified distal cup 2372.
Figure 49:
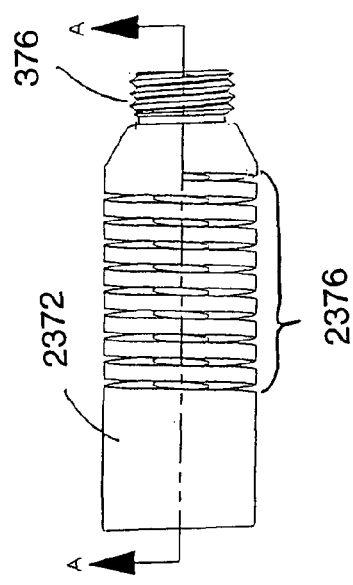
FIG. 49 is a perspective view of the modified distal cup 2372 with the proximal end of the distal cup in the foreground.
Figure 50:
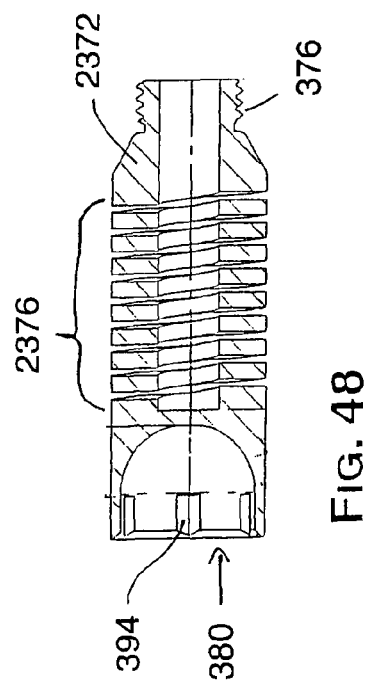
FIG. 50 is a perspective view of the distal cup 2372 with the distal end in the foreground.

FIGS. 47-50 show a modified distal cup 2372 that includes an elastically deformable component in the form of a machined spring 2376. FIG. 47 is a side view of the modified distal cup 2372. FIG. 48 is a cross section of the same distal cup 2372. FIG. 49 is a perspective view with the proximal end of the distal cup 2376 in the foreground. FIG. 50 is a perspective view of the distal cup 2376 with the distal end in the foreground.

Distal cup 2372 may be fabricated to have the same cavity 380 in the distal cup 2372 to receive the distal end 384 of support member 352 and have the same hex ridges 394 to be engaged by the distal cup driver 2200 described above. The distal cup 2372 may be created to have the same external threads 376 on the distal cup 2372 to engage the distal anchor 340 in the same way as distal cup 372 discussed above. The added feature in distal cup 2372 is the ability to undergo elastic compression along the Z-axis as the machined spring 2376 elastically compresses. As the machined spring 2376 may be created to be substantially stiff in resistance to torsion, the presence of the machined spring 2376 may not be noticed during the delivery of the distal cup 2374 to the distal anchor 344.

Figure 51:
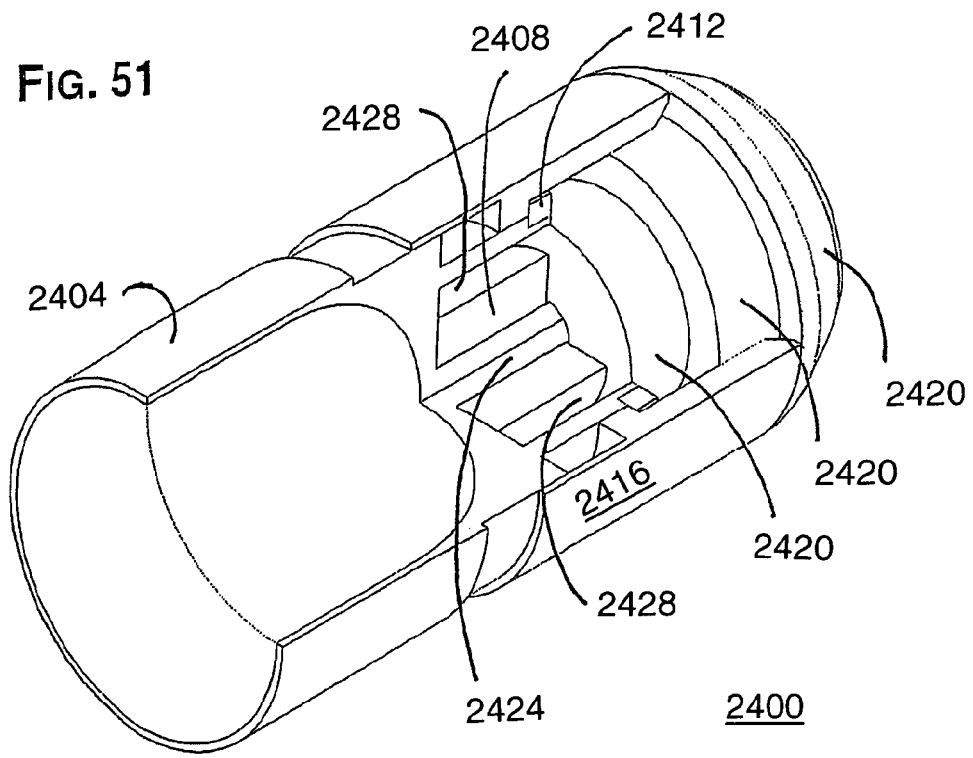
FIG. 51 shows a perspective view of an alternative distal cup 2400 with a partial quarter round removed.

FIG. 51 shows a perspective view with a partial quarter round removed of alternative distal cup 2400. Distal cup 2400 has a cup section 2404 that receives the distal end 384 of the support member 352. The cup section 2404 is capable of a limited range of movement axially relative to an outer sleeve 2416 and a tiered distal segment 2420 that fits up into a distal anchor 344 (excluding the internal threaded section 368 (see FIG. 4)). An O-ring 2412 may be placed around the cup section 2404 adjacent to the outer sleeve 2416.

Figure 52:
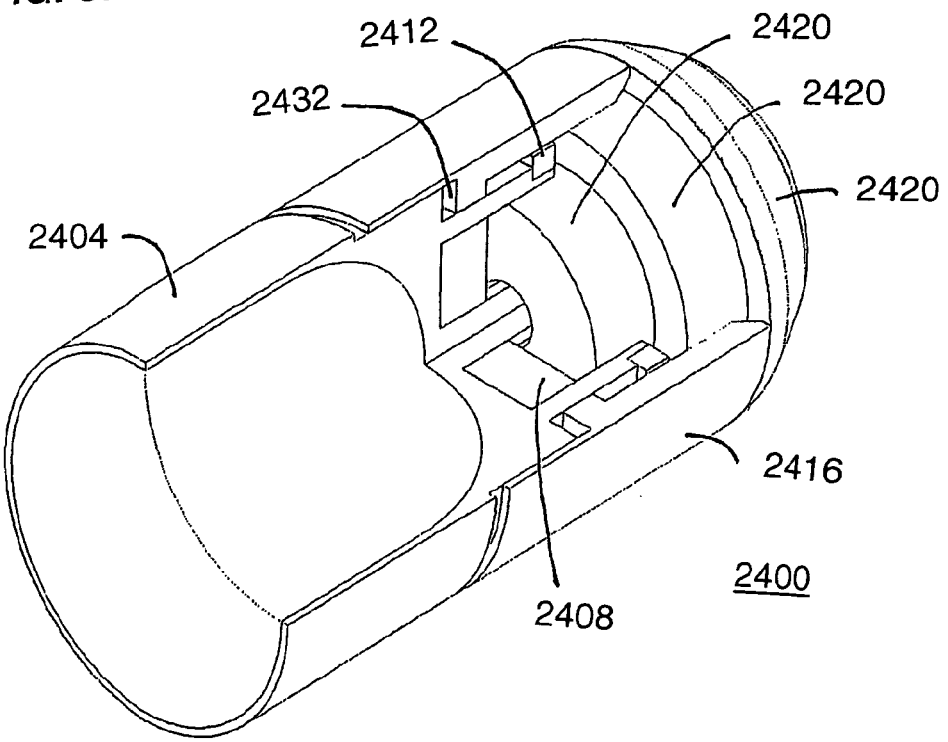
FIG. 52 shows a perspective view of an alternative distal cup 2400 with a partial quarter round removed after compression has caused elastomeric component 2408 to expand to fill the cavity in the alternative distal cup.

As the cup section 2404 moves towards the tiered distal segment 2420, the alignment rod 2424 section of the cup section 2404 moves within a cavity in the tiered distal segment 2420. Comparing FIG. 51 to FIG. 52, elastomeric ring 2408 is elastically deformed as the cup section 2404 moves towards the tiered distal segment 2420. When the elastomeric ring 2408 substantially fills the ring cavity 2428, resistance to axial movement is greatly increased and substantially stops further axial movement. In FIG. 52, the elastomeric ring 2408 is shown as a dark material and fills the ring cavity 2428. Notice that the elastomeric ring 2404 and ring cavity 2428 may be selected relative to the other components so that the ring cavity 2428 is filled before the cup section 2404 bottoms out on the tiered distal segment 2420 as indicated by gap 2432.

The elastomeric ring 2404 may be made from a variety of semi-compliant materials that are appropriate for insertion into a human body such as by way of examples fluoropolymer elastomer (Viton™), polyurethane elastomer, or silicone rubber.

There are a number of options for delivery of the distal cup 2400. Hex ridges such as ridges 394 shown in FIG. 5 could be added so that the distal cup driver 2200 discussed above could be used. Having the same hex ridges so that distal cups with and without elastomeric components could be used with one common driver as deemed expedient with a surgeon's judgment for treating a particular patient would simplify the tool kit.

A set of detent concavities could be placed in the perimeter of the cavity in the cup section which can be selectively engaged by a detent protrusion of a corresponding driver to engage the distal cup to deliver the distal cup to the interior of the distal bone anchor. A description of such detent concavities and a corresponding driver appears in previously filed U.S. patent application Ser. No. 11/256,810 subsequently published as US 2006/0079898 A1 (See for example FIGS. 18 and 19 of the '810 application and the relevant text). The relevant portions of that published application are hereby incorporated by reference.

Yet another delivery option would be a delivery tool analogous to the support member driver 2260 which would receive at least a proximal portion of the distal cup in a shaft and then discharge the distal cup with an appropriate push rod to deliver the distal cup to the distal bone anchor.

Other Possible Locations for Elastic Component

Another option (not shown in the figures) for the use of an elastically deformable component in order to aid the ability for compressive axial translation and load distribution is to place an O-ring, elastomeric washer, or other elastomeric object or spring between the distal end of the distal cup 372 and the distal bone anchor 340. In order to allow for elastic deformation of the spinal motion preservation assembly, the distal cup would need to be able to move relative to the distal anchor so a threaded engagement would not be appropriate. Ideally, the distal cup or the distal bone anchor, or both would be shaped to allow space for the elastomeric material. Such elastomeric components may be configured from semi-compliant materials, for example fluoropolymer elastomer (Viton™), polyurethane elastomer, or silicone rubber.

Another location that could be used for the placement of an elastically deformable component is within the proximal bone anchor between the proximal cup and the jam nut (example not shown). In this configuration the proximal cup would not have external threads so that it would be free to move axially in the cavity of the proximal bone anchor to compress the elastically deformable compound between the proximal end of the proximal cup and the distal face of the jam nut. Yet another location for placement of the elastically deformable component is between the bearing surface and the pivot.

One of skill in the art will recognize that when using two elastically deformable inserts in a single motion preservation assembly, the inserts could have different properties such as being made of different thicknesses or from different materials so that one responded under lower axial loads than the other.

Given an appropriate modification to the shapes of the components within the motion preservation assembly, the elastically deformable components could be springs of any one of various configurations and stiffness that would allow for elastic deformation without reliance on the use of elastomeric components. A coil spring is one option. Another option is one of the various types of spring washer products such as a Belleville disc. Spring washers can be stacked to provide for greater total deflection or simply to change the response curve of deflection to force.

Additional Discussion of Membranes

FIG. 53 shows a perspective view with a quarter round removed of a preformed membrane 2450 with a one inch diameter (as measured inside the preformed membrane before adding silicone material). FIG. 54 shows a cross section of the same one inch preformed membrane 2450. To provide a contrast, FIG. 55 shows a cross section of a ¾ inch preformed membrane 2460 that could be delivered by the same delivery device and membrane tip 2148 but may be preferred by a surgeon working with a disc that has a smaller diameter. FIG. 56 shows a detail applicable to both FIGS. 54 and 55, the membrane channel engagement section 2454 of one side of a membrane. This membrane channel engagement section 2454 is placed within one of the two membrane channels 2180 in a membrane tip 2148 (See FIG. 27) and then held in place by a retainer ring 2156 (See FIG. 26).

FIG. 57 is a perspective view of an alternative membrane 2470. FIG. 58 is a cross section of the same membrane 2470 shown in FIG. 57. Membrane 2470 is a flat membrane and is expanded from flat into a substantially conforming fit within the available space in the intervertebral disc space. When using a flat membrane 2470, there remains some advantage to using a distraction driver with a sheath to protect the flat membrane during delivery to the intervertebral space but this is perhaps less necessary than when using a preformed membrane. Thus, a flat membrane could be delivered with a distraction driver that does not have a sheath to protect the flat membrane during movement to the intervertebral disc space. One of ordinary skill in the art could create a revised distraction driver based upon the disclosed distraction driver 2100 to remove the membrane sheath 2120, membrane sheath key 2124, membrane sheath ring 2128 and relevant connection pins.

Membrane 2470, a highly expandable membrane, may be made of an clastomeric material, e.g., silicone rubber, such as that obtained from Nusil Silicone Technology located in Carpeneria, California, exhibiting a capacity for elongation of between about 500% and about 1500% and most preferably about 1000% and having a wall thickness of 0.220 inches. Membrane 2470 has both a distal membrane channel engagement section 2454 and a proximal membrane channel engagement section 2454 that fit within the two membrane channels 2180 in the relevant membrane tip 2148. After retainer rings 2156 are place-over the two membrane channel engagement sections 2154 to hold the membrane channel engagement sections in the membrane channels 2180 (preferably while compressing the retainer rings 2156 to make the ring smaller), the membrane 2470 is firmly connected to the membrane tip 2148 such that the membrane 2470 will stretch significantly to fill the intervertebral disc space under pressure from inserted prosthetic nucleus material without pulling free of the membrane tip 2148. When the membrane tip 2148 is removed after the inserted prosthetic nucleus material (such as silicone) has cured, the membrane 2470 disengages from the membrane tip 2148 as the membrane channel engagement channels 2454 rip, pull free, or some combination of both.

The flat membrane 2470 will undergo substantial expansion when filled with prosthetic nucleus material. The perimeter of flat membrane 2470 at close to the midline 2474 along the cephalad/caudal axis may increase from about 1.5 inches (diameter of 0.475 nches) to as much as approximately 4 inches or more (diameter of approximately 1.25 inches). This would be an ending midline perimeter of more than 265% of the initial perimeter length. Even if the flat membrane was used in a void with a smaller cross section, the midline perimeter 2474 may increase to more than 2.3 inches (diameter of approximately 0.750 inches), a final midline perimeter 2474 length of more than 150% of the initial midline perimeter length. Such substantial increase in the perimeter length and the increase in surface area makes the expanded flat membrane more susceptible to damage than the unexpanded flat membrane as the expansion thins the wall of the membrane.

The midline perimeter of the membrane as it would be delivered to the disc space substantially aligned with the cephalad/caudal axis is likely to be the portion of the membrane that expands the most when filling the void in the intervertebral disc space. However, one of skill in the art will recognize that the void may not be uniform around the cephalad/caudal axis or the membrane may not be perfectly centered with the void. Thus, the actual perimeter of the membrane that undergoes the maximum growth may be slightly above or slightly below the midline perimeter. The teachings with respect to reducing the increase in size by using a preformed membrane instead of a flat membrane continue to apply.

When using a preformed membrane that approximates the size and shape of the void to be filled, the preformed membrane may not need to expand at all. Even when it does expand, the expansion will be on a much smaller scale. For example, when using a preformed membrane such as preformed membrane 2450 in the same void discussed above that requires expansion to a 1.25 inch outer diameter, the midline perimeter 2458 would change from approximately 3.25 inches (1.040 inch diameter) to approximately 4 inches of midline perimeter (1.25 inch diameter). This would be a final midline perimeter of less than 125% of the initial midline perimeter.

Even if a preformed membrane with a 0.750 inch internal diameter such as preformed membrane 2460 were used in a intervertebral disc space with a void requiring expansion to 1.0 inches of diameter, the increase in midline perimeter 2464 would increase from approximately 2.5 inches (0.790 inches of initial outside diameter) to approximately 3.14 inches (diameter of approximately 1 inch), this would be a final midline perimeter of a little more than 125% of the original midline perimeter.

Membrane Free Alternative

In yet another alternative implementation, the membrane tip analogous to 2148 can be used without any membrane at all. In this alternative implementation, the prosthetic nucleus material 464 (FIG. 4) is introduced directly into the intervertebral disc space, instead of filling a membrane. The injection of prosthetic nucleus material 464 directly into the intervertebral disc space 312 may be performed either with or without a preceding sealant step to seal the surfaces of the intervertebral disc space by means of materials and methods such as described in co-pending and commonly assigned U.S. patent application Ser. No. 11/199,541 filed Aug. 8, 2005, and subsequently published as US 2006-0206209 A1, the relevant material on sealants incorporated by reference.

In summary, in prosthetic nucleus motion preservation assembly embodiments configured without expandable membranes, generally a two-step deployment process is used wherein a barrier-sealant membrane (BSM) is preferably first introduced through conformal contact with the interior surfaces of the intervertebral disc space to seal physiologic structures, e.g., fissures in the annulus, to preclude leakage of the subsequently introduced bulk prosthetic nucleus material. For prosthetic nucleus devices used as part of a motion preservation assembly, the viscoelastic properties, e.g., bulk and compressive moduli, are designed to substantially match those of the native disc nucleus, to functionally enable conformal contact of maximum device surface area within the intervertebral disc space; to mimic physiologic load distribution and dissipation; prevent bone erosion or implant subsidence; and exhibit sufficient resistance to fatigue and shear forces to preclude material fragmentation and migration out of the disc. In embodiments where the motion preservation assemblies are configured for use in conjunction with a barrier-sealant membrane, the barrier-sealant may include aqueous solutions of synthetic or purified (non-antigenic) biopolymers or proteins, such as collagen or collagen-albumin mixtures or slurries; or fibrinogen, thrombin, and the like, or combinations thereof, of suitably highly fibrous; highly cross-linked; high density of solids (e.g., >65mg/ml). In one embodiment, it is preferred that the biopolymer protein system be modified to be insoluble, and that proteins be of Type 1 when possible and appropriate. In another embodiment, the sealant additionally may include a cross-linking agent, e.g., gluteraldehyde/aldehyde, or other suitable functional groups modified to minimize toxicity and/or necroses (e.g., citric-acid derivative).

In a preferred aspect of barrier-sealant membranes, the cross-linking agent(s) may include functionalities which reduce residuals or which are materials that are naturally metabolized. In one embodiment, the cross-linking agent may include at least one citric acid derivative and synthetic or highly purified biopolymer or protein, such as systems as just described, (e.g., collagen; collagen-albumen; collagen; elastin, etc.). In a preferred aspect, the cross-linker is a relatively low weight macromolecule which may include polar functional groups, such as carboxyl groups or hydroxyl groups, that are modified by means of electron attracting groups, e.g., succinimidyl groups.

In yet another embodiment, the barrier-sealant and/or barriers (e.g., thicker layers) may include hydrocolloids. More specifically, the barrier-sealant membrane may be configured to include water soluble hydrophilic colloidal components, e.g., carboxymethylcellulose, in combination with elastomers or biopolymers as sealants or tissue repair matrices, respectively, and wherein the barrier membrane includes non-degradable, semi-permeable film. In other embodiments, barriers may be pectin-based or foam.

Suitable Materials

The design choices for suitable materials for the bone anchors allow the use of titanium, cobalt chromium alloys, or possibly stainless steel. Those of ordinary skill in the art will recognize that other materials could be used for the bone anchors.

With respect to the pivot that comes in contact with the bearing surfaces and the bearing surfaces themselves, it may be useful to select a material with superior wear resistance such as a cobalt-chromium alloy, selected ceramics, stainless steel, MP35N, and possibly even ultra high molecular weight polyethylene (UHMWPE) for the cup but probably not the pivot itself. Many would not consider titanium a good choice for these components. The support body between the pivot ends could be made from titanium, cobalt-chromium alloys, MP35N or other materials.

Moreover, the ends of the support member may be treated (e.g., surface or heat treatments as appropriate) to enhance wear resistance. Thus, while the chemical composition may be the same, the ends of the support member are now a different material from the middle as in this context "material" is a combination of the composition and treatments to produce properties. In yet another implementation, the support member body 392 may be made of another compatible material (e.g., one that will not react so as to cause electrochemical corrosion) so that while the support member ends are made more wear resistant, the material used for the support member body and/or the treatment applied to the support member may be treated to enhance fatigue resistance relative to the material used for the support member ends. Having the support member made from two ends and a body rather than machined from a single piece of metal is not an unreasonable manufacturing strategy even if the ends and body are made from the same material, as highly polished, highly round, spheres are available commercially.

The retainer rings may be made from a shape memory material such as Nitinol. The retainer rings may also be made from a material such as titanium. Such titanium rings can be crimped onto the membrane tip 2148 to hold the membrane in place and then the ends laser welded.

While one viable combination is to use membranes and prosthetic nucleus materials that are the same material so that the injected material becomes one solid nucleus with the membrane (such as occurs when silicone is injected into a silicone membrane), this is not a requirement. Dissimilar materials may be used. When using preformed membranes that are not expected to undergo significant expansion, a wider range of materials may be used including membranes made of semi-complaint specialty fabric. A woven fabric may have the advantageous property of allowing air to quickly-bleed through the fabric during the filling process while retaining the prosthetic nucleus material. (Normally the connection of the membrane to the membrane tip, though strong, is not air tight and air can bleed out the membrane channels.) The prosthetic nucleus material may fill voids in the fabric and such that the fabric becomes captured in the edge of the prosthetic nucleus material before the material cures.

The membrane may be fabricated to have more than one layer. For example, an outer layer that serves to protect the inner layer from sharp edges on bone fragments and an inner layer intended to retain the prosthetic nucleus material. Thus a membrane with an external layer of a woven fabric may contain an inner layer of a material such as silicone.

Additional Details on Retainer Rings

One retainer ring that may be used to retain the membrane is a Nitinol ring, a nickel titanium alloy. As a shape memory alloy, Nitinol resumes a trained shape when it reaches a specific temperature. Cooling Nitinol in a bath of isopropyl alcohol (which may be cooled with dry ice) will allow the Nitinol ring to be expanded so that through a series of cooling and pressing cycles, the Nitinol ring can be expanded and placed over the membrane.

Subsequent heating of the Nitinol rings will cause them to resume their original shape and retain the membrane. Application of an appropriate adhesive to the underside of the membrane channel engagement section 2454 of a membrane before applying a retaining ring helps keep the membrane in position during the efforts to place the retaining ring over the membrane.

Alternatives and Variations

Delivery to Motion Segment other than L5/S1

In order to provide concreteness to the disclosure provided above, a specific motion segment was discussed. In this instance it was the L5/S1 motion segment. While the dimensions of components may be slightly different when implanted in a different motion segment, nothing in the above disclosure should be interpreted as limiting the disclosure to therapeutic treatment of the L5/S1 motion segment. Other motion segments including by way of example and not limitation the L5/L4 motion segment and the L3/L4 motion segment may benefit from delivery of a spinal motion preservation assembly that uses one or more teachings from the present disclosure.

Adaptation of Sheathed Delivery to Deliver a Prosthetic Nucleus

Figure 59:
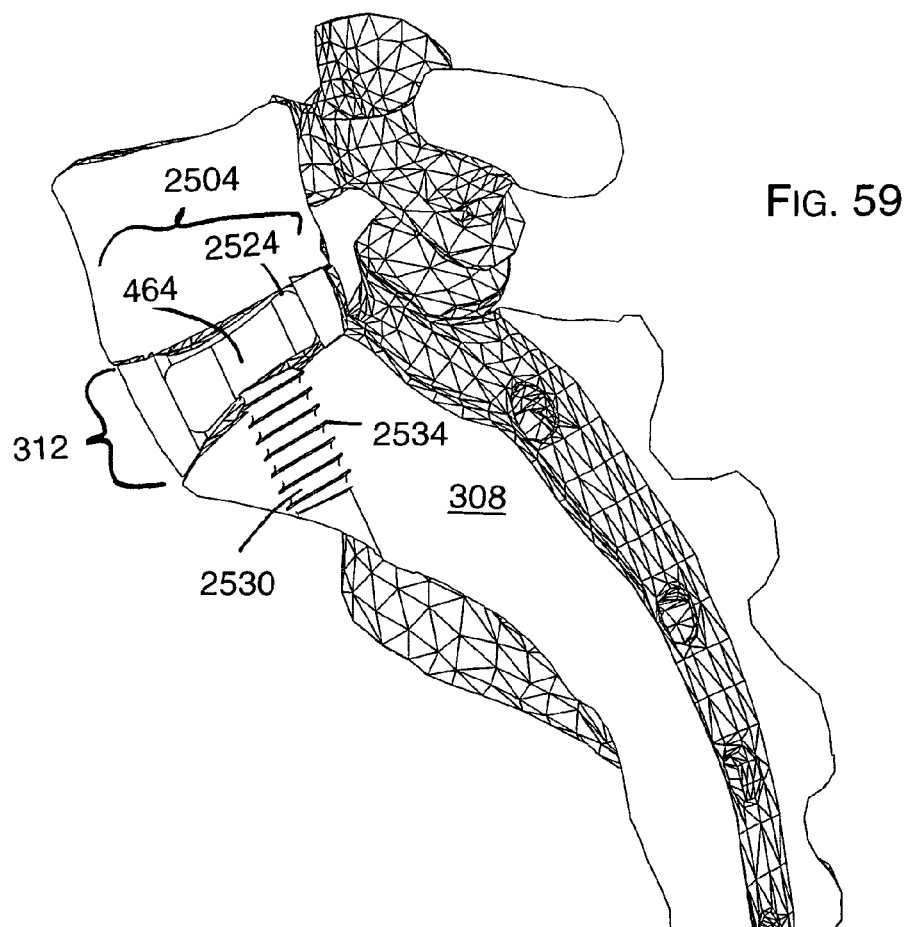
FIG. 59 shows a cross section of a spine with an implanted prosthetic nucleus 2504.
Figure 60:
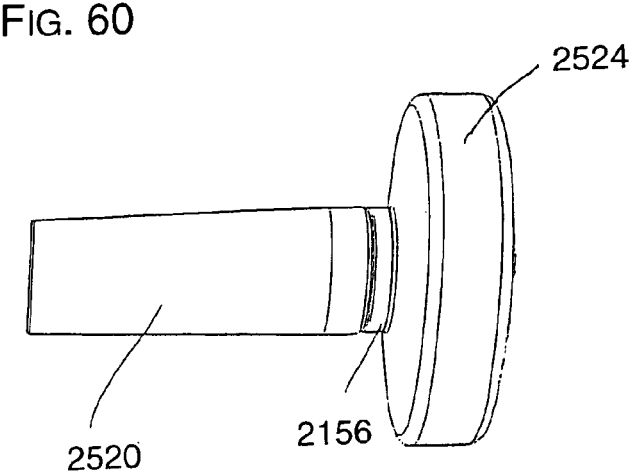
FIG. 60 shows a membrane tip 2520 with a preformed membrane 2524.

A subset of the teachings in the present disclosure could be adapted to deliver an intact and undamaged prosthetic nucleus membrane to an intervertebral disc space. FIGS. 59 and 60 help depict this process. FIG. 59 shows a cross section of a spine with an implanted prosthetic nucleus 2504 and FIG. 60 shows a membrane tip 2520 with a preformed membrane 2524.

As shown in FIG. 59, an axial bore would be prepared through the proximal vertebral body 308 (such as the sacrum) and the intervertebral disc space 312 would be prepared in keeping with this disclosure and surgical needs of the specific patient. The distraction driver of the present disclosure could be fitted with a shorter single ring membrane tip 2520 that uses a preformed membrane 2524 with a single opening and single membrane channel engagement section (not visible here but compare FIG. 56) engaged with a single retainer ring 2156. After the preformed membrane 2524 is moved through the axial channel to the intervertebral disc space 312, the sheath would be withdrawn to uncover the preformed membrane 2524. The membrane tip 2520 could be positioned to be close to the edge between the proximal vertebral body 308 and the intervertebral disc space 312. Prosthetic nucleus material 464, such as silicone, could be delivered as described above with the difference that rather than a series of lateral ports, a single distal port (not shown) would be used to fill the preformed membrane 2524 to substantially conform to the void in the intervertebral disc space 312. Using a preformed membrane 2524 of approximately the required size would reduce or eliminate the need to expand the preformed membrane 2524 when filling the preformed membrane 2524 thus making the membrane less susceptible to damage.

Subsequent to curing of the prosthetic nucleus material 464 and the removal of the membrane tip 2520 from the axial channel, the withdrawal causing the membrane attached to the cured prosthetic nucleus to rip and/or pull free from the retainer ring 2156, a stop flow means (for example a bone plug 2530) could be delivered to plug the bore in the proximal vertebral body 308. In one implementation, the bone plug 2530 may include external threads 2534 to engage the bone peripheral to the axial bore in the proximal vertebral body. One could use an axial bore and bone plug 2530 of a smaller cross section than shown in FIG. 59. For example, an axial bore of 400 mils (0.400 inches) or less may be sufficient to allow passage of a sheathed membrane and a membrane tip. The bone plug for an axial bore of 400 mils would tend to have a minor diameter for the threaded section of 400 mils or slightly more than 400 mils. The bone plug 2530 could be made from an allograft, a biocompatible metal, a biocompatible polymer, or another appropriate substance.

One of skill in the art could make a delivery tool that delivers membranes of this type without the capacity to perform distraction rather than use the distraction driver 2100 of this present disclosure with a modified membrane tip. The discussion of this alternative implementation of some of the teachings of the present disclosure has intentionally been held brief given the lengthy disclosure overall. One of ordinary skill in the art will recognize that the preformed membrane could be made of a woven fabric, a multilayer membrane, a material different from the injected prosthetic nucleus material and all of the other variations discussed in connection with the other prosthetic nucleus membranes.

Preformed Prosthetic Nucleus

The disclosure has discussed the creation of a prosthetic nucleus through the delivery of flowable prosthetic nucleus material (with or without an external membrane) and the subsequent curing of the prosthetic nucleus material to form a prosthetic nucleus. Many teachings of the present disclosure may be applied while using a set of one or more previously formed prosthetic nucleus discs. The discs would be delivered to the intervertebral disc space either in many thin layers or in thicker discs with a radial slit so that the split disc could be delivered to the intervertebral disc space before reassuming a disc shape. As long as the discs had an open center, the support member could be inserted as described above after insertion of the discs.

A disc could be inserted from a supplemental access route substantially orthogonal to the axis of the spine. (substantially orthogonal being within 45 degrees of orthogonal) If done during distraction of the motion segment, a split disc could be inserted into the intervertebral disc space to substantially encircle the distraction tool. After the distraction tool was removed, the inserted disc material would substantially maintain the distraction and the process of delivering the components could continue in keeping with the teachings set forth above.

Multilevel Spinal Motion Preservation Assemblies

While the implementations described in detail above are directed to a spinal motion preservation assembly providing therapy to a single motion segment, this is not an inherent limitation for the teachings of the present disclosure.

For example, a spinal motion assembly could be implemented in accordance with the teachings of the present disclosure wherein the spinal implant assembly includes: a means for anchoring the spinal implant assembly to a third vertebra located immediately adjacent to and more cephalad than the more cephalad of the first and second vertebrae, an additional pivot-like means so that after the spinal implant assembly is anchored to both of the first and second adjacent vertebrae and to the third vertebra that the third vertebra can move relative to the more cephalad of the first and second adjacent vertebra in addition to the more cephalad of the first and second adjacent vertebra being able to move relative to the more caudal of the first and second adjacent vertebra.

Turning to FIG. 61, a two level spinal motion preservation assembly 3500 is shown in a perspective view (with the membranes hidden to allow a better view of the components). FIG. 62 shows the various components beyond the three bone anchors and two membranes (membranes not shown). Visible in FIG. 62 are distal bone anchor 3504, medial bone anchor 3508, and proximal bone anchor 3512. In this particular implementation, the major diameters of the distal bone anchor 3504, medial bone anchor 3508, and proximal bone anchor 3512 are the same and the three bone anchors may be delivered by a single delivery tool using timed delivery so that the thread path cut by the distal bone anchor 3504 is used by the medial bone anchor 3508 and the proximal bone anchor 3512. In a manner analogous to that described above in connection with the delivery of two anchors, the three anchors would be loaded onto the driver, perhaps using alignment marks (not shown here but compare element 472 in FIG. 6) and delivered such that the distal bone anchor 3504 is placed in proper position. The driver would be removed from engagement with the distal bone anchor 3504 and then the position of the medial bone anchor 3508 would be adjusted. The driver would be removed from engagement with the medial bone anchor 3508 and the placement of the proximal bone anchor 3512 would be adjusted.

Turning now to FIG. 62, the components internal to the two-level spinal motion preservation assembly 3500 are shown. The dual pivot for the distal motion segment has a distal cup 3604, support member 3608, and proximal cup 3612. Seal ring 3616 which is placed in the medial anchor 3508 is also shown. In addition to the seal ring 3616 and the proximal cup 3612, the medial anchor includes the distal cup 3620 for the proximal motion segment. The dual pivot for the proximal motion segment includes the distal cup 3620, the support member 3624, and the proximal cup 3628. The proximal anchor 3512 also includes seal ring 3632 and jam nut 3636.

When working with a two-level spinal motion preservation assembly, it may be useful to carefully calculate the dimensions of the two motion segments after the desired distractions so that components can be carefully selected from a range of components of different sizes that the assembly is sized appropriately to minimize the amount of adjustment required.

The delivery of a two-level spinal motion preservation assembly differs from the discussion of FIGS. 3-7 in that in addition to what is done in connection with FIGS. 3-7, the two-level spinal motion preservation assembly also anchors the spinal motion assembly to a third vertebral body immediately adjacent to and more cephalad than the original distal vertebral body which is the most cephalad of the two original vertebral bodies. The two-level spinal motion preservation assembly includes an additional pivot means so this third vertebral body is able to move relative to the original distal vertebral body (which now becomes the medial vertebral body).

Alternatives to the Stabilizer/Slot Pair

The delivery sequence set forth above made use of a proximal anchor stabilizer 2380 with stabilizer fingers 2384 (See FIGS. 43-45) to engage with slots 456 (FIG. 5). The teachings of the present disclosure should not be limited to this specific finger and slot arrangement. Other irregular surfaces on the proximal face 408 of the proximal anchor could be used as a point of engagement with a stabilizer tool. One of ordinary skill in the art will appreciate that in this context an irregular surface feature is not just a texture but a protrusion or cavity within one or more surfaces accessible during process steps that might inadvertently rotate the proximal anchor.

In order to provide concrete examples, specific handedness of screw threads are shown in the figures and implied in the description of the process steps. One of ordinary skill in the art may alter all or some of the handedness of threads without departing from the teachings of the present disclosure.

Use of a Single Pivot

While the range of motion for a motion segment with an installed spinal motion preservation assembly having a bearing surface in each of the two bone anchors (as shown in FIGS. 9(c) and 9(d) may allow for a greater range of motion for the motion segment than a single pivot (compare FIGS. 9(a) and (b)), nothing should be interpreted as limiting the disclosure to a double pivot or a specific form of a double pivot unless the limitation is explicit in the claims as spinal motion preservation assemblies may be fabricated using a range of pivot options within the spirit of the present disclosure.

Figure 63:
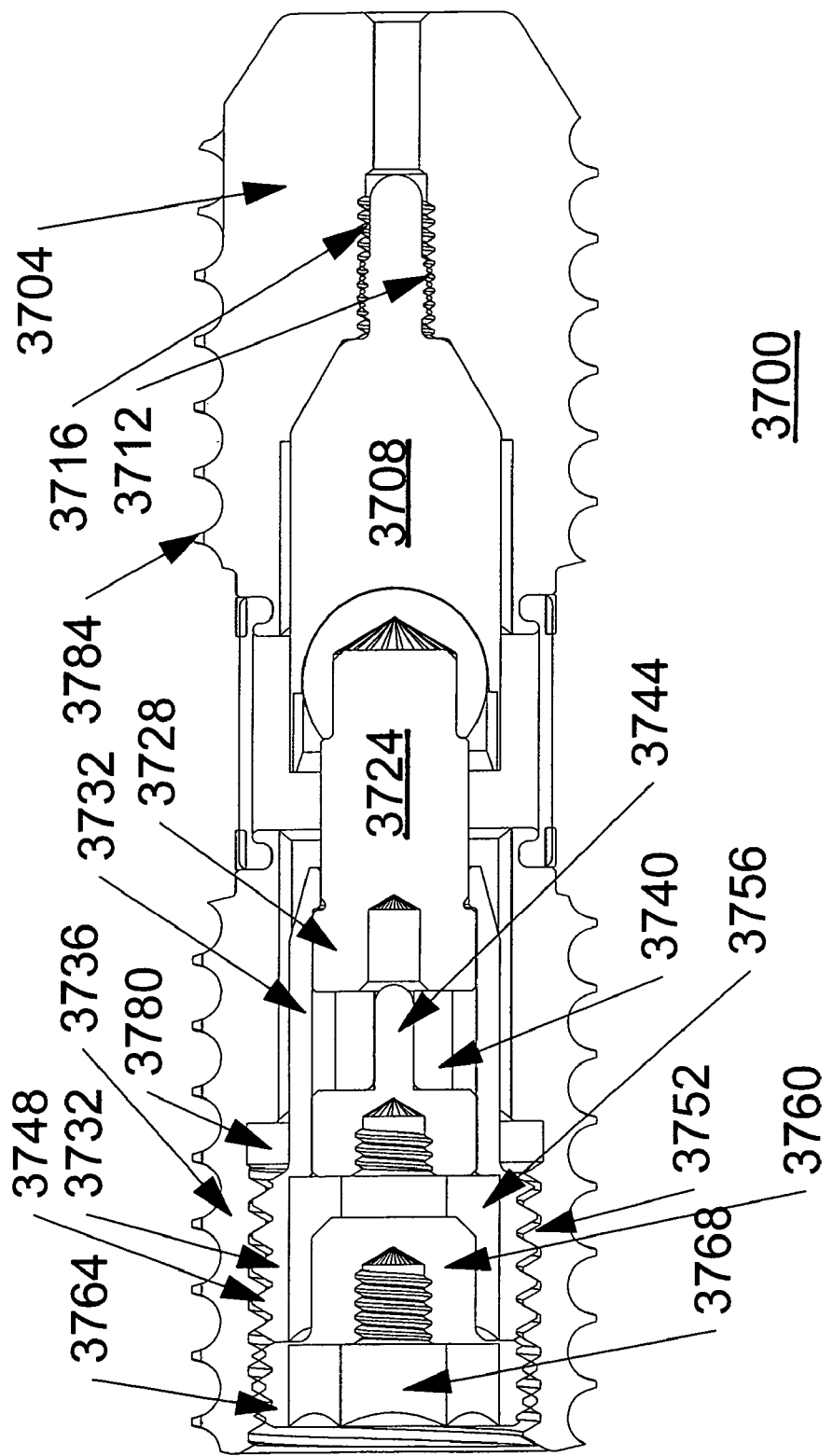
FIG. 63 is a cross section of a spinal motion preservation assembly 3700 that uses a single pivot.

FIG. 63 provides an example of a spinal motion preservation assembly 3700 with a single pivot design. The spinal motion preservation assembly 3700 is shown here without a prosthetic nucleus so that the components of the spinal motion preservation assembly can be clearly shown and discussed. Distal bone anchor 3704 has a distal cup 3708 that is threadedly engaged via external threads 3712 on the distal cup 3708 and internal threads 3716 on the distal anchor 3704. The distal cup 3708 has a bearing surface for the spherical end 3720 of the single pivot 3724. The proximal end 3728 of the single pivot 3724 is free to move axially for a range of motion within the sleeve 3732 inside proximal bone anchor 3736. The movement of the proximal end 3728 is limited by elastomeric ring 3740 which encircles post 3744.

Sleeve 3732 has external threads 3748 engaged with internal threads 3752 in proximal anchor 3736. Sleeve 3732 has a driver engagement section 3756 for applying torque from an appropriate driver (not shown). A jam nut 3760 with external threads 3764 and driver engagement section 3768 abuts the proximal end of the sleeve 3732 and extends into the driver engagement section 3756 of the sleeve 3732.

Also visible are seal ring 3780 and alignment marks 3784 which are used to align the two anchors on the driver for timed delivery.

As discussed in connection with FIG. 9, a spinal motion preservation assembly using a single pivot will not have the same range of motion as a similar spinal motion preservation assembly using a dual pivot. Spinal motion preservation assembly 3700 will have the ability for compression along the cephalad/caudal axis based on the design using an elastomeric component 3740.

Multiple Bearing Surfaces

Figure 64:
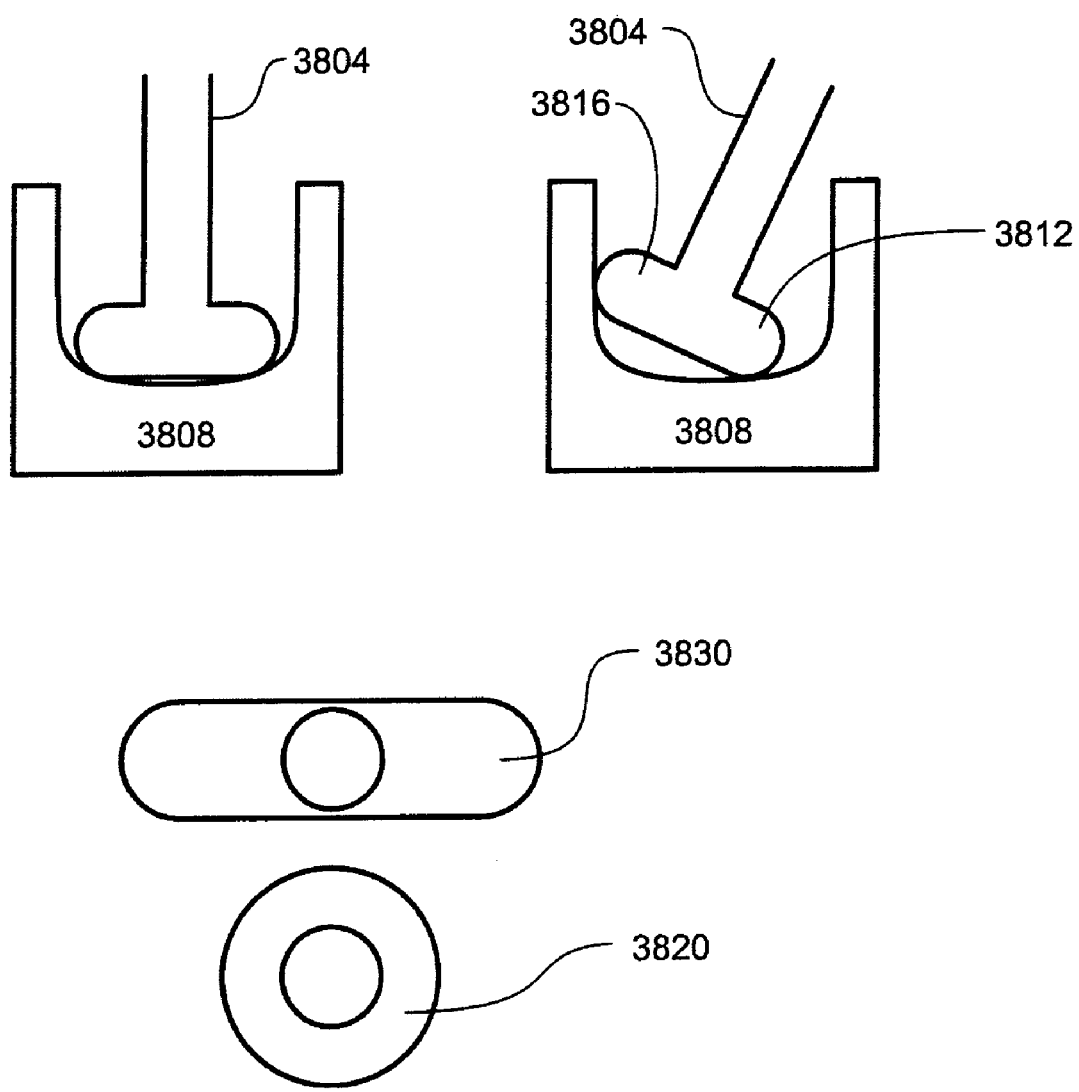
FIG. 64 introduced concepts relevant to having multiple bearing surfaces.

FIG. 64 illustrates that a pivot 3804 could engage with a pivot cup 3808 such that it effectively has more than one pivot/bearing surface pair as at points of the range of motion of the pivot 3804, different portions of the pivot 3804 are serving as the point of pivot contact (see portion 3812 is engaged while portion 3816 is not in contact with the bearing surface). The pivot may be axially symmetric as shown from above looking at pivot 3820 or asymmetric as shown in the cross sectional view from above pivot 3830. The selective use of a pivot body/cup surface to form multiple bearing surfaces allows additional control of the motion characteristics of the spinal motion preservation assembly.

Selected teachings of the present disclosure could be implemented with delivery paths that while caudal to cephalad, do not cross the sacrum. Alternatively, a delivery path which can establish a suitable axial channel could be used to deliver a spinal motion preservation assembly in keeping with one or more teachings of this disclosure even if the axial path was cephalad towards caudal so that caudal became distal for that delivery process.

One of skill in the art will recognize that some of the alternative implementations set forth above are not universally mutually exclusive and that in some cases additional implementations can be created that employ aspects of two or more of the variations described above. Likewise, the present disclosure is not limited to the specific examples or particular embodiments provided to promote understanding of the various teachings of the present disclosure. Moreover, the scope of the claims which follow covers the range of variations, modifications, and substitutes for the components described herein as would be known to those of skill in the art.

The legal limitations of the scope of the claimed invention are set forth in the claims that follow and extend to cover their legal equivalents. Those unfamiliar with the legal tests for equivalency should consult a person registered to practice before the United States Patent and Trademark Office.

What is claimed is:

1. A driver for delivering an insert to a bone anchor, the bone anchor having an internal cavity with a set of internal threads, the driver adapted to rotate with respect to a bone anchor that is anchored in a vertebral body in order to engage external threads on the insert with the set of internal threads in the bone anchor and axially advance the threadedly engaged insert within the bone anchor while simultaneously preventing the bone anchor from rotating with respect to the vertebral body the driver having:
   a threaded retention rod for engaging a bore in the insert;
   a driver head distinct from the threaded retention rod, the driver head to engage with the insert to apply torque to the insert and rotate the insert; and
   an anchor stabilizer distinct from the threaded retention rod and distinct from the driver head, the anchor stabilizer to engage with a proximal face of the bone anchor to prevent the bone anchor from rotating with respect to the vertebral body
   wherein the threaded retention rod may be rotated relative to the driver head and the anchor stabilizer to allow the threaded retention rod to engage the insert; and
   wherein the driver head may be rotated relative to the anchor stabilizer to rotate the insert relative to the bone anchor engaged with the anchor stabilizer.

2. The driver of claim 1 wherein the anchor stabilizer engages with an engagable surface accessible from an end of the bone anchor that receives the insert.

3. The driver of claim 1 wherein the driver is adapted to axially advance fingers on the anchor stabilizer to engage with slots in the bone anchor along a perimeter of an end of the bone anchor that receives the insert.

4. The driver of claim 1 wherein the threaded retention rod is adapted to engage the insert with a threaded element connected to the driver so that the insert is threadedly engaged with the driver until threadedly engaged with the bone anchor and released from threaded engagement with the driver.

* * * * *